(12) United States Patent
Kruse

(10) Patent No.: US 11,520,043 B2
(45) Date of Patent: Dec. 6, 2022

(54) SYSTEMS AND METHODS FOR SYNTHETIC APERTURE ULTRASOUND IMAGING OF AN OBJECT

(71) Applicant: Decision Sciences Medical Company, LLC, Poway, CA (US)

(72) Inventor: Dustin E. Kruse, Grand Island, NY (US)

(73) Assignee: Decision Sciences Medical Company, LLC, Poway, CA (US)

(*) Notice: Subject to any disclaimer, the term of this patent is extended or adjusted under 35 U.S.C. 154(b) by 0 days.

(21) Appl. No.: 17/581,495

(22) Filed: Jan. 21, 2022

(65) Prior Publication Data

US 2022/0155440 A1 May 19, 2022

Related U.S. Application Data

(63) Continuation of application No. PCT/US2021/059424, filed on Nov. 15, 2021.
(Continued)

(51) Int. Cl.
*G01S 15/89* (2006.01)
*A61B 8/08* (2006.01)
(Continued)

(52) U.S. Cl.
CPC ......... *G01S 15/8997* (2013.01); *A61B 8/145* (2013.01); *A61B 8/4477* (2013.01);
(Continued)

(58) Field of Classification Search
CPC ............ G01S 15/8997; G01S 7/52028; G01S 15/8915; G01S 15/8929; G01S 15/8977;
(Continued)

(56) References Cited

U.S. PATENT DOCUMENTS 4,105,018 A 8/1978 Greenleaf et al.
4,110,755 A 8/1978 Zottl
(Continued)

FOREIGN PATENT DOCUMENTS

CA 2427186 5/2001
CA 2852801 5/2013
(Continued)

OTHER PUBLICATIONS

Australian Exam Report dated Oct. 18, 2019 for Australian Application No. 2016222637, filed on Feb. 25, 2016 (3 pages).
(Continued)

*Primary Examiner* — Oommen Jacob
(74) *Attorney, Agent, or Firm* — Perkins Coie LLP

(57) ABSTRACT

Techniques, systems, and devices are disclosed for synthetic aperture ultrasound imaging using a beamformer that incorporates a model of the object. In some aspects, a system includes an array of transducers to transmit and/or receive acoustic signals at an object that forms a synthetic aperture of the system with the object, an object beamformer unit to (i) beamform the object coherently as a function of position, orientation, and/or geometry of the transducers with respect to a model of the object, and (ii) produce a beamformed output signal including spatial information about the object derived from beamforming the acoustic echoes; a data processing unit to process data and produce an image of the object based on a rendition of the position, the orientation, the geometry, and/or the surface properties of the object, relative to the coordinate system of the array, as determined by the data processing unit.

30 Claims, 25 Drawing Sheets

Related U.S. Application Data

(60) Provisional application No. 63/113,536, filed on Nov. 13, 2020.

(51) Int. Cl.
    *A61B 8/00* (2006.01)
    *A61B 8/14* (2006.01)
    *G01S 7/52* (2006.01)

(52) U.S. Cl.
    CPC .......... *A61B 8/4488* (2013.01); *A61B 8/5207* (2013.01); *G01S 7/52028* (2013.01); *G01S 15/8915* (2013.01); *G01S 15/8929* (2013.01); *G01S 15/8977* (2013.01); *G01S 15/8936* (2013.01); *G01S 15/8993* (2013.01)

(58) Field of Classification Search
    CPC . G01S 15/8936; G01S 15/8993; A61B 8/145; A61B 8/4477; A61B 8/4488; A61B 8/5207
    See application file for complete search history.

(56) References Cited

U.S. PATENT DOCUMENTS

| | | | |
|---|---|---|---|
| 4,159,462 A | 6/1979 | Rocha et al. |
| 4,277,367 A | 7/1981 | Madsen et al. |
| 4,437,468 A | 3/1984 | Sorenson |
| 4,463,608 A | 8/1984 | Takeuchi et al. |
| 4,620,546 A | 11/1986 | Aida et al. |
| 4,821,206 A | 4/1989 | Arora |
| 4,830,015 A | 5/1989 | Okazaki |
| 4,888,746 A | 12/1989 | Wurster et al. |
| 5,039,774 A | 8/1991 | Shikinamie et al. |
| 5,181,513 A | 1/1993 | Touboul et al. |
| 5,241,964 A | 9/1993 | McQuilkin |
| 5,269,309 A | 12/1993 | Fort et al. |
| 5,284,143 A | 2/1994 | Rattner |
| 5,329,944 A | 7/1994 | Fabian et al. |
| 5,394,877 A | 3/1995 | Orr et al. |
| 5,417,218 A | 5/1995 | Spivey et al. |
| 5,445,144 A | 8/1995 | Wodicka et al. |
| 5,465,722 A | 11/1995 | Fort et al. |
| 5,522,878 A | 6/1996 | Montecalvo |
| 5,533,510 A | 7/1996 | Koch, III et al. |
| 5,608,690 A | 3/1997 | Hossack et al. |
| 5,623,928 A | 4/1997 | Wright et al. |
| 5,793,701 A | 8/1998 | Wright et al. |
| 5,800,356 A | 9/1998 | Criton et al. |
| 5,803,089 A | 9/1998 | Ferre et al. |
| 5,806,518 A | 9/1998 | Mittelstadt |
| 5,829,444 A | 11/1998 | Ferre et al. |
| 5,868,676 A | 2/1999 | McCabe et al. |
| 5,873,830 A | 2/1999 | Hossack et al. |
| 5,882,557 A | 3/1999 | Hayakawa et al. |
| 5,902,244 A | 5/1999 | Kobayashi et al. |
| 5,913,823 A | 6/1999 | Hedberg et al. |
| 5,967,980 A | 10/1999 | Ferre et al. |
| 6,016,285 A | 1/2000 | Wright et al. |
| 6,039,694 A | 3/2000 | Larson |
| 6,045,507 A | 4/2000 | Muzilla et al. |
| 6,050,945 A | 4/2000 | Peterson et al. |
| 6,083,164 A | 7/2000 | Oppelt et al. |
| 6,106,464 A | 8/2000 | Bass et al. |
| 6,110,114 A | 8/2000 | Nock et al. |
| 6,113,544 A | 9/2000 | Mo |
| 6,123,669 A | 9/2000 | Kanda |
| 6,132,375 A | 10/2000 | Napolitano |
| 6,157,592 A | 12/2000 | Kriz et al. |
| 6,205,411 B1 | 3/2001 | DiGioia, III et al. |
| 6,231,834 B1 | 5/2001 | Unger et al. |
| 6,241,676 B1 | 6/2001 | Savord |
| 6,322,567 B1 | 11/2001 | Mittelstadt et al. |
| 6,338,765 B1 | 1/2002 | Statnikov |
| 6,340,363 B1 | 1/2002 | Bolger et al. |
| 6,341,231 B1 | 1/2002 | Ferre et al. |
| 6,402,707 B1 | 6/2002 | Ernst |
| 6,436,045 B1 | 8/2002 | Rafter et al. |
| 6,445,943 B1 | 9/2002 | Ferre et al. |
| 6,508,766 B2 | 1/2003 | Sato et al. |
| 6,537,216 B1 | 3/2003 | Shifrin |
| 6,583,392 B2 | 6/2003 | Hershey et al. |
| 6,585,648 B1 | 7/2003 | Robinson |
| 6,620,101 B2 | 9/2003 | Azzam et al. |
| 6,626,916 B1 | 9/2003 | Yeung et al. |
| 6,652,461 B1 | 11/2003 | Levkovitz et al. |
| 6,687,531 B1 | 2/2004 | Ferre et al. |
| 6,725,082 B2 | 4/2004 | Sati et al. |
| 6,736,780 B2 | 5/2004 | Song et al. |
| 6,757,582 B2 | 6/2004 | Brisson et al. |
| 6,785,571 B2 | 8/2004 | Glossop |
| 6,786,097 B2 | 9/2004 | Song et al. |
| 6,796,988 B2 | 9/2004 | Melkent et al. |
| 6,808,494 B2 | 10/2004 | Shifrin |
| 6,843,957 B2 | 1/2005 | Statnikov |
| 6,918,877 B2 | 7/2005 | Hossack et al. |
| 6,934,575 B2 | 8/2005 | Ferre et al. |
| 6,939,300 B2 | 9/2005 | Petersen et al. |
| 6,960,173 B2 | 11/2005 | Babaev |
| 7,004,906 B1 | 2/2006 | Guracar et al. |
| 7,066,886 B2 | 6/2006 | Song et al. |
| 7,070,565 B2 | 7/2006 | Vaezy |
| 7,207,939 B2 | 4/2007 | Husher |
| 7,226,456 B2 | 6/2007 | O'Neil et al. |
| 7,291,119 B1 | 11/2007 | de Guise et al. |
| 7,344,609 B2 | 3/2008 | Statnikov |
| 7,395,181 B2 | 7/2008 | Foxlin |
| 7,473,250 B2 | 1/2009 | Makin et al. |
| 7,532,201 B2 | 5/2009 | Quistgaard et al. |
| 7,542,790 B2 | 6/2009 | Jensen et al. |
| 7,566,304 B2 | 7/2009 | Nakamura et al. |
| 7,678,049 B2 | 3/2010 | Tsoref et al. |
| 7,719,515 B2 | 5/2010 | Fujiwara et al. |
| 7,719,689 B2 | 5/2010 | Lee et al. |
| 7,728,487 B2 | 6/2010 | Adachi et al. |
| 7,763,035 B2 | 7/2010 | Melkent et al. |
| 7,798,585 B2 | 9/2010 | Oguri |
| 7,806,823 B2 | 10/2010 | Sakai et al. |
| 7,826,889 B2 | 11/2010 | David et al. |
| 7,835,778 B2 | 11/2010 | Foley et al. |
| 7,835,784 B2 | 11/2010 | Mire et al. |
| 7,837,625 B2 | 11/2010 | Abe |
| RE42,194 E | 3/2011 | Foley et al. |
| 7,905,836 B2 | 3/2011 | Dan |
| 7,917,317 B2 | 3/2011 | McKeon |
| 7,938,777 B2 | 5/2011 | Amiot et al. |
| 7,938,778 B2 | 5/2011 | Sakai |
| 7,982,362 B2 | 7/2011 | Adachi et al. |
| 8,002,705 B1 | 8/2011 | Napolitano et al. |
| 8,038,616 B2 | 10/2011 | Angelsen et al. |
| 8,043,220 B2 | 10/2011 | Okada et al. |
| 8,103,461 B2 | 1/2012 | Glaser et al. |
| 8,105,339 B2 | 1/2012 | Melkent et al. |
| 8,126,533 B2 | 2/2012 | Lavallee |
| 8,137,272 B2 * | 3/2012 | Cooley ............... G01S 7/52028 600/463 |
| 8,147,409 B2 | 4/2012 | Shifrin |
| 8,152,726 B2 | 4/2012 | Amiot et al. |
| 8,165,658 B2 | 4/2012 | Waynik et al. |
| 8,241,217 B2 | 8/2012 | Chiang et al. |
| 8,251,908 B2 | 8/2012 | Vortman et al. |
| 8,253,578 B2 | 8/2012 | Watabe et al. |
| 8,311,611 B2 | 11/2012 | Csavoy et al. |
| 8,323,200 B2 | 12/2012 | Kunita |
| 8,372,070 B2 | 2/2013 | Tanaka et al. |
| 8,374,674 B2 | 2/2013 | Gertner |
| 8,409,099 B2 | 4/2013 | Vitek et al. |
| 8,409,103 B2 | 4/2013 | Grunwald et al. |
| 8,444,564 B2 | 5/2013 | Mahfouz et al. |
| 8,447,388 B2 | 5/2013 | Igarashi |
| 8,491,476 B2 | 7/2013 | Iwama et al. |
| 8,556,834 B2 | 10/2013 | Gertner |
| 8,565,860 B2 | 10/2013 | Kimchy et al. |
| 8,626,267 B2 | 1/2014 | Lavallee |

(56) References Cited

U.S. PATENT DOCUMENTS

| | | | |
|---|---|---|---|
| 8,675,939 B2 | 3/2014 | Moctezuma de la Barrera |
| 8,771,188 B2 | 7/2014 | Schers et al. |
| 8,774,900 B2 | 7/2014 | Buly et al. |
| 8,814,810 B2 | 8/2014 | Roche et al. |
| 8,864,686 B2 | 10/2014 | Roche et al. |
| 8,880,152 B2 | 11/2014 | Lavallee |
| 8,909,325 B2 | 12/2014 | Kimchy et al. |
| 8,939,909 B2 | 1/2015 | Wegner |
| 9,060,794 B2 | 6/2015 | Kang et al. |
| 9,101,394 B2 | 8/2015 | Arata et al. |
| 9,127,998 B1 | 9/2015 | Guldiken et al. |
| 9,174,065 B2 | 11/2015 | Gertner |
| 9,196,046 B2 | 11/2015 | Meyer |
| 9,220,571 B2 | 12/2015 | Lavallee |
| 9,244,169 B2 | 1/2016 | Fan et al. |
| 9,248,001 B2 | 2/2016 | Colombet et al. |
| 9,352,171 B2 | 5/2016 | Gertner |
| 9,387,276 B2 | 7/2016 | Sun et al. |
| 9,420,999 B2 | 8/2016 | Wegner |
| 9,572,548 B2 | 2/2017 | Moctezuma de la Barrera |
| 9,597,058 B2 | 3/2017 | Kanayama et al. |
| 9,844,359 B2 | 12/2017 | Gerbaulet et al. |
| 9,872,667 B2 | 1/2018 | Wegner |
| 9,878,506 B2 | 1/2018 | Zhao et al. |
| 10,085,722 B2 | 10/2018 | Wegner |
| 10,321,889 B2 | 6/2019 | Wegner |
| 10,426,429 B2 | 10/2019 | Kruse et al. |
| 10,743,838 B2 | 8/2020 | Freiburg |
| 10,993,699 B2 | 5/2021 | Wegner |
| 11,096,661 B2 | 8/2021 | Wegner |
| 11,191,521 B2 | 12/2021 | Freiburg et al. |
| 2002/0068871 A1 | 6/2002 | Mendlein et al. |
| 2002/0099290 A1 | 7/2002 | Haddad |
| 2002/0122536 A1 | 9/2002 | Kerrien et al. |
| 2002/0188229 A1 | 12/2002 | Ryaby et al. |
| 2003/0036702 A1 | 2/2003 | Davidsen |
| 2003/0125628 A1 | 7/2003 | Song et al. |
| 2004/0066708 A1 | 4/2004 | Ogawa |
| 2004/0236223 A1 | 11/2004 | Barnes et al. |
| 2005/0101861 A1 | 5/2005 | Satoh |
| 2005/0101867 A1 | 5/2005 | Johnson et al. |
| 2006/0004290 A1 | 1/2006 | Smith et al. |
| 2006/0009693 A1* | 1/2006 | Hanover ............... A61B 90/11 600/407 |
| 2006/0119223 A1 | 6/2006 | Ossman |
| 2006/0173305 A1 | 8/2006 | Asafusa et al. |
| 2006/0173313 A1* | 8/2006 | Liu ................. G01S 15/8993 600/437 |
| 2007/0066897 A1 | 3/2007 | Sekins et al. |
| 2007/0156050 A1 | 7/2007 | Barnes et al. |
| 2007/0226976 A1 | 10/2007 | Zipparo et al. |
| 2007/0239001 A1 | 10/2007 | Mehi et al. |
| 2007/0239002 A1 | 10/2007 | Alam |
| 2007/0265690 A1 | 11/2007 | Lichtenstein et al. |
| 2007/0276238 A1 | 11/2007 | Sudol |
| 2008/0110263 A1 | 5/2008 | Klessel et al. |
| 2008/0119737 A1 | 5/2008 | Urbano et al. |
| 2008/0200810 A1 | 8/2008 | Buchalter |
| 2008/0208055 A1 | 8/2008 | Bertram et al. |
| 2008/0281202 A1 | 11/2008 | Fraser et al. |
| 2008/0281237 A1 | 11/2008 | Slayton et al. |
| 2008/0319318 A1* | 12/2008 | Johnson ............ G01S 7/52036 600/445 |
| 2009/0043206 A1 | 2/2009 | Towfiq et al. |
| 2009/0066727 A1* | 3/2009 | Lu ................... G01S 7/52085 345/643 |
| 2009/0093737 A1 | 4/2009 | Gerbaulet et al. |
| 2009/0124871 A1 | 5/2009 | Arshak et al. |
| 2009/0306497 A1 | 12/2009 | Manzke et al. |
| 2010/0179425 A1 | 7/2010 | Zadicario |
| 2010/0204577 A1 | 8/2010 | Sekins et al. |
| 2010/0268072 A1 | 10/2010 | Hall et al. |
| 2010/0274139 A1 | 10/2010 | Fukukita et al. |
| 2010/0280379 A1 | 11/2010 | Satoh |
| 2010/0286518 A1 | 11/2010 | Lee et al. |
| 2011/0092862 A1 | 4/2011 | Chivers |
| 2011/0264012 A1 | 10/2011 | Lautzenhiser et al. |
| 2012/0029345 A1 | 2/2012 | Mahfouz et al. |
| 2012/0238875 A1 | 9/2012 | Savitsky et al. |
| 2012/0281507 A1 | 11/2012 | Rikoski |
| 2013/0060121 A1 | 3/2013 | Patwardhan et al. |
| 2013/0144135 A1 | 6/2013 | Mahfouz et al. |
| 2013/0144166 A1 | 6/2013 | Specht et al. |
| 2013/0150863 A1 | 6/2013 | Baumgartner |
| 2013/0165005 A1 | 6/2013 | Berard-Anderson et al. |
| 2013/0218013 A1 | 8/2013 | Barthe et al. |
| 2014/0163377 A1 | 6/2014 | Kang et al. |
| 2014/0180116 A1 | 6/2014 | Lindekugel et al. |
| 2015/0018682 A1 | 1/2015 | Schers et al. |
| 2015/0038613 A1 | 2/2015 | Sun et al. |
| 2015/0088040 A1 | 3/2015 | Barthe et al. |
| 2015/0133788 A1 | 5/2015 | Mauldin, Jr. et al. |
| 2015/0164467 A1 | 6/2015 | Suetoshi et al. |
| 2015/0182191 A1 | 7/2015 | Caluser et al. |
| 2015/0297173 A1* | 10/2015 | Klock ................ A61B 8/0825 600/442 |
| 2015/0313572 A1 | 11/2015 | Gerbaulet et al. |
| 2015/0359512 A1 | 12/2015 | Boctor et al. |
| 2015/0374334 A1* | 12/2015 | Klock ..................... A61B 8/14 600/447 |
| 2016/0000409 A1 | 1/2016 | Bruder et al. |
| 2016/0100821 A1 | 4/2016 | Eggers et al. |
| 2016/0104267 A1* | 4/2016 | Hancock ............ G01S 7/52077 382/131 |
| 2016/0157828 A1* | 6/2016 | Sumi ..................... G01N 29/46 702/189 |
| 2016/0270763 A1 | 9/2016 | Hayes et al. |
| 2018/0126677 A1 | 5/2018 | Zhao et al. |
| 2019/0307427 A1* | 10/2019 | Levy .................... A61B 6/5217 |
| 2020/0284902 A1* | 9/2020 | Kruse ................ G01S 15/8927 |
| 2022/0155440 A1* | 5/2022 | Kruse ................ G01S 7/52028 |

FOREIGN PATENT DOCUMENTS

| | | |
|---|---|---|
| CN | 100354651 | 12/2007 |
| CN | 101325913 | 12/2008 |
| CN | 102258399 | 11/2012 |
| CN | 104169739 | 11/2014 |
| EP | 952461 | 10/1999 |
| EP | 1707124 | 4/2006 |
| EP | 1795917 | 6/2007 |
| EP | 1854406 | 11/2007 |
| EP | 1955668 | 8/2008 |
| EP | 2033579 | 3/2009 |
| GB | 2379392 | 3/2003 |
| GB | 2472066 | 1/2011 |
| IL | 232148 | 7/2019 |
| JP | 55051351 | 4/1980 |
| JP | 58195550 | 11/1983 |
| JP | 60048736 | 3/1985 |
| JP | 62117535 | 5/1987 |
| JP | 8038473 | 2/1996 |
| JP | 2000041980 | 2/2000 |
| JP | 2000166922 A | 6/2000 |
| JP | 2000287988 A | 10/2000 |
| JP | 2003190157 A | 7/2003 |
| JP | 2004147852 A | 5/2004 |
| JP | 2005152608 A | 6/2005 |
| JP | 2010082425 A | 4/2010 |
| JP | 2011062531 A | 3/2011 |
| JP | 2011177461 | 9/2011 |
| JP | 2012002586 A | 1/2012 |
| JP | 2013056156 | 3/2013 |
| JP | 2013520235 | 6/2013 |
| WO | 2002024094 | 3/2002 |
| WO | 2007023477 | 3/2007 |
| WO | 2007069156 | 6/2007 |
| WO | 2009009064 | 1/2009 |
| WO | 2009020617 | 2/2009 |
| WO | 2009063421 | 5/2009 |
| WO | 2013066821 | 5/2013 |
| WO | 2013103956 | 7/2013 |
| WO | 2014128593 | 8/2014 |

(56) References Cited

FOREIGN PATENT DOCUMENTS

| WO | 2014150780 | 9/2014 | |
|---|---|---|---|
| WO | 2014150961 | 9/2014 | |
| WO | 2014186904 | 11/2014 | |
| WO | 2015038554 | 3/2015 | |
| WO | 2016044830 | 3/2016 | |
| WO | 2016138257 | 9/2016 | |
| WO | 2016149427 | 9/2016 | |
| WO | WO-2019084526 A1 * | 5/2019 | ............ A61B 8/4488 |

OTHER PUBLICATIONS

Callow, H.J., "Signal Processing for Synthetic Aperture Sonar Image Enhancement," Thesis for Ph.D. in Electrical and Electronic Engineering at the University of Canterbury, Christchurch, New Zealand, 273 pages, Apr. 2003.

Cao, Z. et al., "Fabrication and properties of thermosensitive organic/inorganic hybrid hydrogel thin films," Langmuir, American Chemical Society, vol. 24, No. 10, May 20, 2008, pp. 5543-5551.

Chiao, R., "Coded Excitation for Diagnostic Ultrasound: A System Developer's Perspective," *IEEE Transactions on Ultrasonics, Ferroelectrics, and Frequency Control*, 52(2):160-170, Feb. 2005.

Choe, J.W., et al., "Volumetric real-time imaging using a CMUT ring array," IEEE Transactions on Ultrasonics, Ferroelectrics, and Frequency Control, 59(6):1201-1211, Jun. 2012.

Demi, L., et al., "In Vitro and In Vivo Tissue Harmonic Images Obtained With Parallel Transmit Beamforming by Means of Orthogonal Frequency Division Multiplexing," IEEE Transactions on Ultrasonics, Ferroelectrics, and Frequency Control, 62(1):230-235, Jan. 2015.

European Search Report dated Apr. 19, 2017 for European Application No. 14844538.0, filed on Sep. 9, 2014 (10 pages).

European Search Report dated Feb. 1, 2019 for European Application No. 16756353.5, filed on Feb. 25, 2016 (14 pages).

European Search Report dated Jun. 29, 2015 for European Application No. 12845256.2, filed on Oct. 29, 2012 (8 pages).

Exam Report dated Oct. 18, 2019 for Australian Application No. 2016222637, filed on Feb. 25, 2016 (3 pages).

Examination Report dated Dec. 20, 2019 for Europe Patent Application No. 14844538.0, filed on Sep. 9, 2014 (7 pages).

Examination Report dated Jul. 19, 2021 for European Application No. 12845256.2, filed on Oct. 29, 2012 (8 pages).

Examination Report dated Jul. 26, 2018 for Canada Patent Application No. 2,852,801, filed on Oct. 29, 2012, 4 pages.

Examination Report dated Mar. 16, 2018 for European Application No. 12845256.2, filed on Oct. 29, 2012 (8 pages).

Extended European Search Report dated Jul. 2, 2019 for European Application No. 16756353.5, filed on Feb. 25, 2016(14 pages).

First Examination Report dated Apr. 12, 2016 for Australian Patent Application No. 2012332817, filed on Oct. 29, 2012, 3 pages.

First Examination Report dated Nov. 21, 2018 for Australian Patent Application No. 2018203785, filed on Oct. 29, 2012, 2 pages.

Hunter, A.J., et al., "A Comparison of Fast Factorised Back-Projection and Wavenumber Algorithms for SAS Image Reconstruction," Proceedings of the World Congress on Ultrasonics, 4 pages, (2003).

International Search Report and Written Opinion dated Jul. 6, 2016 for International Application No. PCT/US2016/019554, filed on Feb. 25, 2016 (12 pages).

International Search Report and Written Opinion dated Mar. 3, 2015 for International Application No. PCT/US2014/054855, filed on Sep. 9, 2014 (11 pages).

International Search Report and Written Opinion dated May 15, 2013 for International Application No. PCT/US2012/062435, filed on Oct. 29, 2012 (9 pages).

Ito, T., et al., "Evaluation of Acoustic Imaging System Using Correlation Division in Synthetic Transmit Aperture with Multicarrier Signals," IEICE Transactions on Fundamentals of Electronics, Communications and Computer Sciences, E94-A(10):1907-1919, Oct. 2011.

Jensen, J.A., et al., "Synthetic Aperture Ultrasound Imaging," Ultrasonics, 44(Suppl 1):e5-e15, Dec. 2006.

Koch, A., et al., "An Ultrasound Tomography System With Polyvinyl Alcohol (PVA) Moldings for Coupling: In Vivo Results for 3-D Pulse-Echo Imaging of the Female Breast," IEEE Transactions on Ultrasonics, Ferroelectrics, and Frequency Control, 62(2):266-279, Feb. 2015.

Kundur, D., et al., "A Novel Blind Deconvolution Scheme for Image Restoration Using Recursive Filtering," IEEE Transactions on Signal Processing, 46(2):375-390, Feb. 1998.

Misaridis, T., "Use of Modulated Excitation Signals in Medical Ultrasound. Part I: Basic Concepts and Expected Benefits," *IEEE Transactions on Ultrasonics, Ferroelectrics, and Frequency Control*, 52(2):177-191, Feb. 2005.

Misaridis, T., "Use of Modulated Excitation Signals in Medical Ultrasound. Part II: Design and Performance for Medical Imaging Applications," IEEE Transactions on Ultrasonics, Ferroelectrics, and Frequency Control, 52(2):192-207, Feb. 2005.

Misaridis, T., "Use of Modulated Excitation Signals in Medical Ultrasound. Part III: High Frame Rate Imaging," *IEEE Transactions on Ultrasonics, Ferroelectrics, and Frequency Control*, 52(2):208-219, Feb. 2005.

Murphy, R.J. et al.,"Pose Estimation of Known Objects During Transmission Tomographic Image Reconstruction." IEEE Transactions on Medical Imaging, vol. 25, No. 10, Oct. 2006, 13 pages.

Notification of Defects dated Nov. 22, 2017 for Israel Patent Application No. 232148, filed on Oct. 29, 2012, 4 pages.

O'Donnell, M., "Coded Excitation for Synthetic Aperture Ultrasound Imaging," IEEE Transactions on Ultrasonics, Ferroelectrics, and Frequency Control, 52(2):171-176, Feb. 2005.

Office Action dated Aug. 30, 2020 for Israel Application No. 264906, filed on Oct. 29, 2012, with English translation, 10 pages.

Office Action dated Jan. 14, 2020 for Japanese Application No. 2017-563504, filed on Feb. 25, 2016 (14 pages).

Office Action dated Jun. 4, 2019 for Japanese Application No. 2017-187288, filed on Oct. 29, 2012 (3 pages).

Office Action dated Mar. 17, 2020 for Japanese Application No. 2018-145683, filed on Sep. 9, 2014 (4 pages).

Office Action dated Mar. 25, 2020 for Japanese Application No. 2016-542050, filed on Sep. 9, 2014 (4 pages).

Office Action dated Oct. 20, 2020 for Canadian Application No. 2,923,861, 4 pages.

Office Action dated Oct. 29, 2019 for Japanese Application No. 2018-145683, filed on Sep. 9, 2014 (3 pages).

Office Action dated Oct. 7, 2021 in Israel Patent Application No. 254158, 6 pages, with English translation.

Office Action dated Dec. 4, 2019 for Chinese Application No. 201680023999.9, filed on Feb. 25, 2016 (23 pages).

Office Action dated Jul. 3, 2018 for Japanese Application No. 2017-187288, filed on Oct. 29, 2012 (6 pages).

Office Action dated Jun. 11, 2019 for Japanese Application No. 2016-542050, filed on Sep. 9, 2014 (15 pages).

Office Action dated Jun. 18, 2019 for Japanese Patent Application No. 2018-145683, filed on Sep. 9, 2014, 12 pages.

Office Action dated Jun. 5, 2018 for Chinese Patent Application No. 201480062224.3, filed on Sep. 9, 2014, 13 pages.

Office Action dated Sep. 13, 2016 for Japanese Application No. 2014-539114, filed on Oct. 29, 2012 (4 pages).

Office Action dated Sep. 19, 2017 for Japanese Application No. 2016-542050, filed on Sep. 9, 2014 (15 pages).

Office Action dated Sep. 2, 2015 for Chinese Application No. 201280065031.4, filed on Oct. 29, 2012 (26 pages).

Office Action dated Sep. 23, 2020 in Israel Patent Application No. 254158, 3 pages.

Principles of Computer Tomography. Textbook, Introduction, Chapter 1, and Chapter 8. Retrieved 1999, 39 pages.

Prokop A F et al., "Polyacrylamide gel as an acoustic coupling medium for focused ultrasound therapy." Ultrasound in Medicine and Biol, New York, NY, US, vol. 29, No. 9, Sep. 1, 2003, pp. 1351-1358.

Rui Silva, S., et al., "2 Synthetic Aperture Techniques for Sonar Systems," Advances in Sonar Technology, edited by Sergio Rui

(56) References Cited

OTHER PUBLICATIONS

Silva, publisher I-Tech Education and Publishing, ISBN 978-3-902613-48-6, pp. 15-42, Feb. 2009.
Second Office Action dated Jul. 14, 2020 for Chinese Patent Application No. 201680023999.9 (41 pages).
Second Office Action dated Jul. 20, 2016 for Chinese Patent Application No. 201280065031.4, filed on Oct. 29, 2012 (26 pages).
Singapore Exam Report dated Feb. 26, 2019 for Singapore Application No. 11201706953Y, filed on Feb. 25, 2016 (6 pages).
Singapore Search Report dated Sep. 24, 2018 for Singapore Application No. 11201706953Y, filed on Feb. 25, 2016 (13 pages).
Singapore Written Opinion dated Jul. 10, 2017 for Singapore Application No. 11201601906P, filed on Sep. 9, 2014 (8 pages).
Stayman, J.W. et al., "Model-Based Tomographic Reconstruction of Objects Containing Known Components." IEEE Transactions on Medical Imaging, vol. 31, No. 10, Oct. 2012, 12 pages.
Trots, I. et al., "Synthetic Aperture Method in Ultrasound Imaging," Chapter 3 of "Ultrasound Imaging," edited by Masayuki Tanabe (2011) (pp. 37-56).
Wikipedia. Rotation matrix. Retrieved from the internet on Sep. 17, 2020 from <https://en.wikipedia.org/wiki?Rotation_matrix>, 26 pages.
Zhu, S., et al., "SAS Autofocus Based on Phase Gradient Autofocus," IEEE 2011 Fourth International Workshop on Chaos-Fractals Theories and Applications (IWCFTA), pp. 298-301, Oct. 19-22, 2011.
International Search Report and Written Opinion dated Feb. 4, 2022 in International Patent Application No. PCT/US21/59424, 19 pages.
Principles of Computer Tomography, Textbook, Chapter, 1, Computerized Tomographic Imaging, retrieved in 2020, 4 pages.
Principles of Computer Tomography, Textbook, Chapter, 8, Reflection Tomography, retrieved in 2020, 26 pages.
Principles of Computer Tomography, Textbook, Intro, retrieved in 2020, 9 pages.
Wikipedia: Rotation matrix. Retrieved on Sep. 17, 2020 from <https://en.wikipedia.org/wiki/Rotation_matrix>, 26 pages.

* cited by examiner

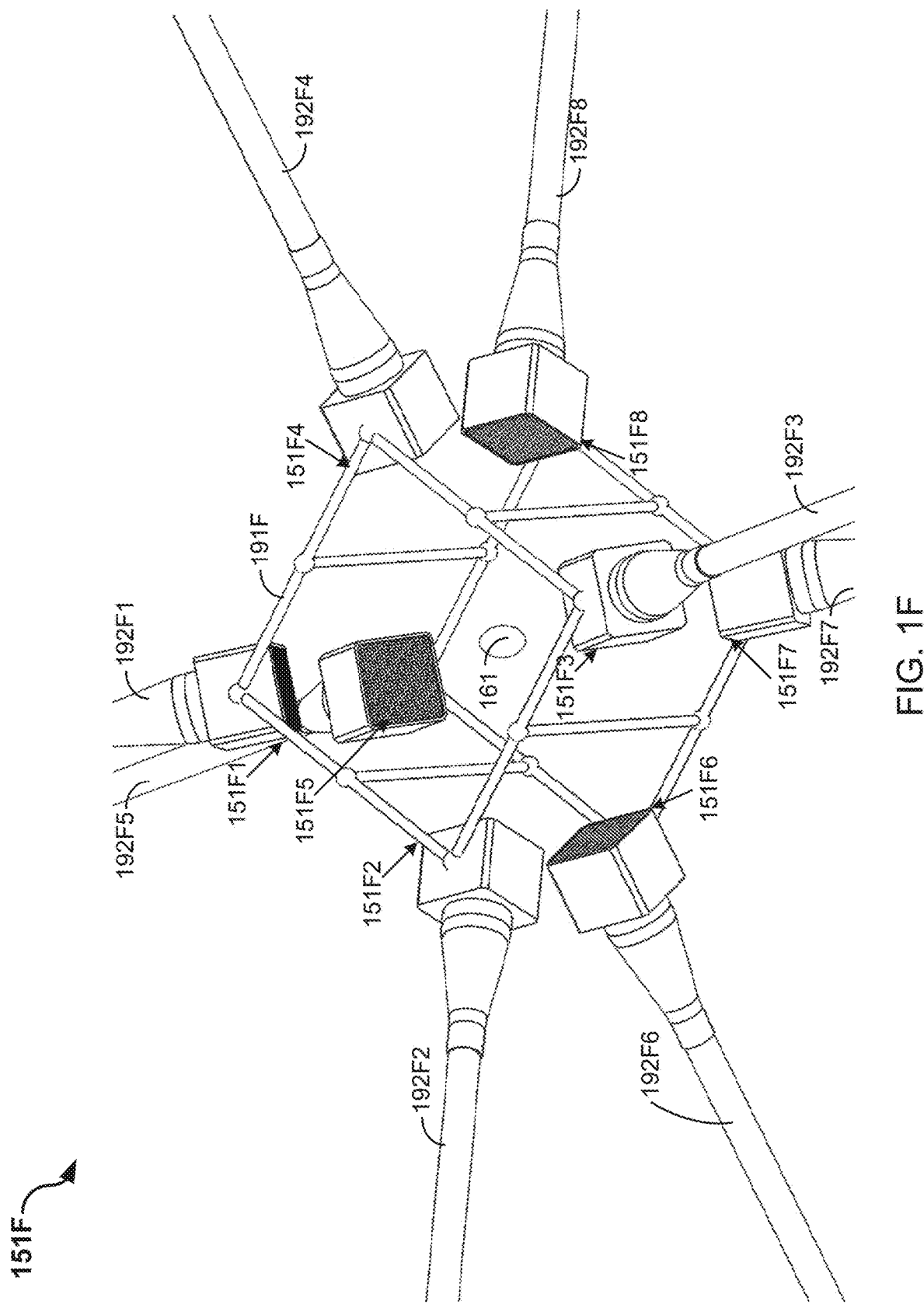

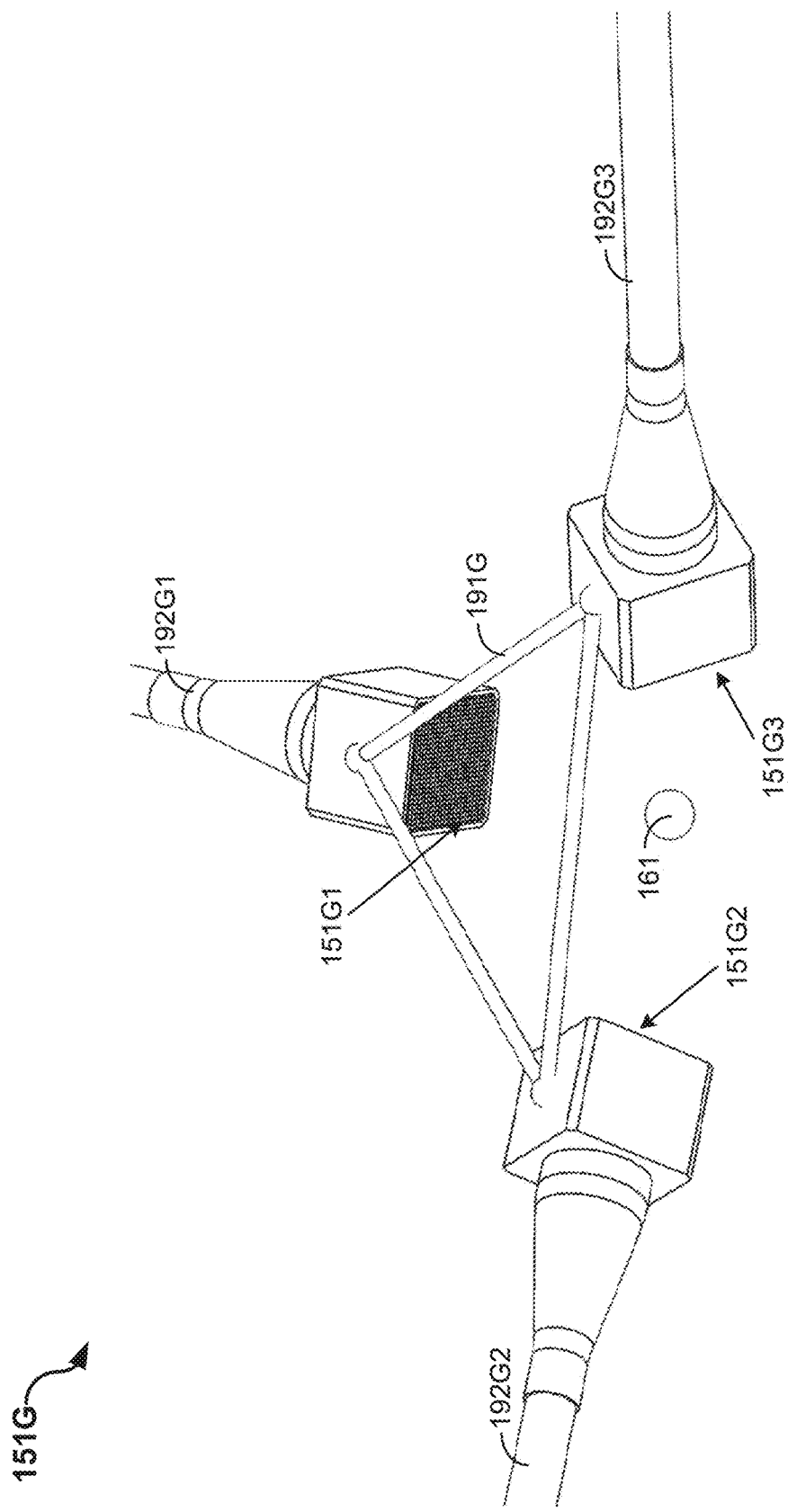

800

810
Transmit and receive acoustic signals, by transducer elements of a transducer array, at and from an object by forming a synthetic aperture based on transmitting of transduced acoustic waveforms at the object and receiving returned acoustic echoes from the object

815
Beamform the object using echo samples of the returned acoustic echoes from one or more regions of the object to produce one or more beamformed output signals

820

821
Generate one or more scalar outputs that are based on one or more beamformed output signals, which are functions of one or more inputs to the beamforming process

825
Optimize the one or more scalar outputs as a function of at least some of a position, an orientation, a geometry, and/or a physical property of the object and/or at least some of a position, an orientation, or a geometry of the transducer array

830
Detect the object by determining a degree of optimization of one or more objective functions based on values of or changes in inputs and outputs of an optimization compared to detection criteria

840
Produce an image of the object based on a rendition of the position, orientation, the geometric property, and/or the surface properties of the object

FIG. 8A

SYSTEMS AND METHODS FOR SYNTHETIC APERTURE ULTRASOUND IMAGING OF AN OBJECT

CROSS-REFERENCE TO RELATED APPLICATIONS

This patent document is a continuation of International Patent Application No. PCT/US21/59424 titled "SYSTEMS AND METHODS FOR TOMOGRAPHIC SYNTHETIC APERTURE ULTRASOUND IMAGING OF AN OBJECT PRODUCING SURFACE REFLECTIONS" filed on Nov. 15, 2021, which claims priorities to and benefits of U.S. Provisional Patent Application No. 63/113,536 titled "SYSTEMS AND METHODS FOR TOMOGRAPHIC SYNTHETIC APERTURE ULTRASOUND IMAGING OF AN OBJECT PRODUCING SURFACE REFLECTIONS" filed on Nov. 13, 2020. The entire content of the aforementioned patent applications is incorporated by reference as part of the disclosure of this patent document.

TECHNICAL FIELD

This patent document relates to multi-dimensional acoustic image formation.

BACKGROUND

Acoustic imaging is an imaging modality that employs the properties of sound waves traveling through a medium and interactions between the sound energy and the medium to obtain an image of the medium or a region of the medium in various applications including medical imaging.

SUMMARY

Disclosed are devices, systems and methods for generating an image of an object as a whole, as compared to traditional imaging of point scatterers, using an aperture comprised of a plurality of spatially separated transmitters, receivers, and/or transmitters and receivers (i.e., transceivers), such that acoustic scattering from the object effectively creates a synthetic aperture with the object, combined with an object beamformer and optimization method that localizes the object. In some implementations, the disclosed systems, devices and methods provide a precision object-feature detector and locator that can identify specific points or regions on the object's surface, enabling measurement of distances and angles between specific points or regions on the object with respect to each other and/or to the transducer array. In some implementations, the disclosed systems, devices and methods provide the position and orientation of the entire object with respect to the frame of reference of the system.

In some embodiments, the imaging aperture forms a tomographic aperture that partially or fully surrounds an object to be imaged in such a way that the object is insonified from many directions and returned echoes are received from many directions in accordance with standard practices of synthetic aperture imaging and reflection tomography. However, instead of tomographically forming a 3D image of the object, e.g., the object is reconstructed from two or more 2D cross-sectional beamformed images of the object generated in the conventional way, the disclosed systems, devices and methods form an image of the object using transmission and reception methods in accordance with synthetic aperture reflection tomography combined with an object beamformer and optimization method that localizes the object in three dimensions.

In some embodiments, a tomographic synthetic aperture acoustic imaging system includes (i) an array of transducer elements operable to transmit, receive, and/or transmit and receive acoustic signals in such a way so as to form a synthetic aperture with the object; (ii) an object beamformer unit to generate a beamformer that (a) coherently localizes on one or more regions of an object as a function of the array of transducer elements' geometry, position, and orientation, and a model of the object, and (b) produces one or more beamformed output signals that are a function of all inputs; and (iii) a display unit to display the localized object, e.g., such that a rendition of the object may be visualized and made useful in the frame of reference of an array or any external frame(s) of reference and operable to update and visualize relative movement between the object and the array. In some embodiments, for example, the tomographic synthetic aperture acoustic imaging system can be configured to localize one or more regions on the surface of one or more objects and provide means to measure distance and angle between two or more regions.

In some aspects, a tomographic synthetic aperture acoustic imaging system includes: an array of transducer elements operable to transmit, receive, and/or transmit and receive acoustic signals at an object that forms a synthetic aperture of the acoustic imaging system with the object, wherein the acoustic signals include transmitted acoustic signals and received acoustic echoes returned from the object; an object beamformer unit comprising one or more processors and one or more memories and configured to (i) beamform the object for one or more regions of the object as a function of position, orientation, and/or geometry of the array of transducer elements with respect to a model of the object, the model of the object comprising information representative of the object, and (ii) produce one or more beamformed output signals in digital format that includes spatial information about the one or more regions of object derived from beamforming the acoustic echoes; a data processing unit, comprising a processor and a memory, in communication with the object beamformer unit and the array of transducer elements, and configured to optimize one or more beamformed output signals to determine one or more of a position, an orientation, a geometry, or a set of physical properties; and a display unit operable to produce an image of the object based on a rendition of one or more of the position, the orientation, the geometry, or the set of physical properties, relative to the coordinate system of the array of transducer elements, as determined by the data processing unit.

In some embodiments in accordance with the present technology (example B36), a method for tomographic synthetic aperture acoustic imaging includes: transmitting and receiving acoustic signals, by transducer elements of an array of transducer elements, at and from an object by forming a synthetic aperture based on transmitting of transduced acoustic waveforms at the object and receiving returned acoustic echoes from the object; beamforming the object using echo samples of the received returned acoustic echoes that returned from one or more regions of the object to produce one or more beamformed output signals, wherein the one or more beamformed output signals are functions of one or more inputs for the beamforming, wherein the one or more inputs for the beamforming includes information representative of the object; optimizing the one or more beamformed output signals to determine one or more of a position, an orientation, a geometry, or a set of physical properties of the object; and producing an image of the object based on a rendition of the one or more of the position, the orientation, the geometry, or the set of physical properties of the object.

BRIEF DESCRIPTION OF THE DRAWINGS

FIGS. 1F-1H show diagrams illustrating example embodiments of an array of transducer elements of an example tomographic synthetic aperture ultrasound system, in accordance with the present technology.

FIG. 8A shows a diagram illustrating an example embodiment of a method for tomographic synthetic aperture imaging of an object by beamforming the object as a whole in accordance with the present technology.

DETAILED DESCRIPTION

Figure 1A:
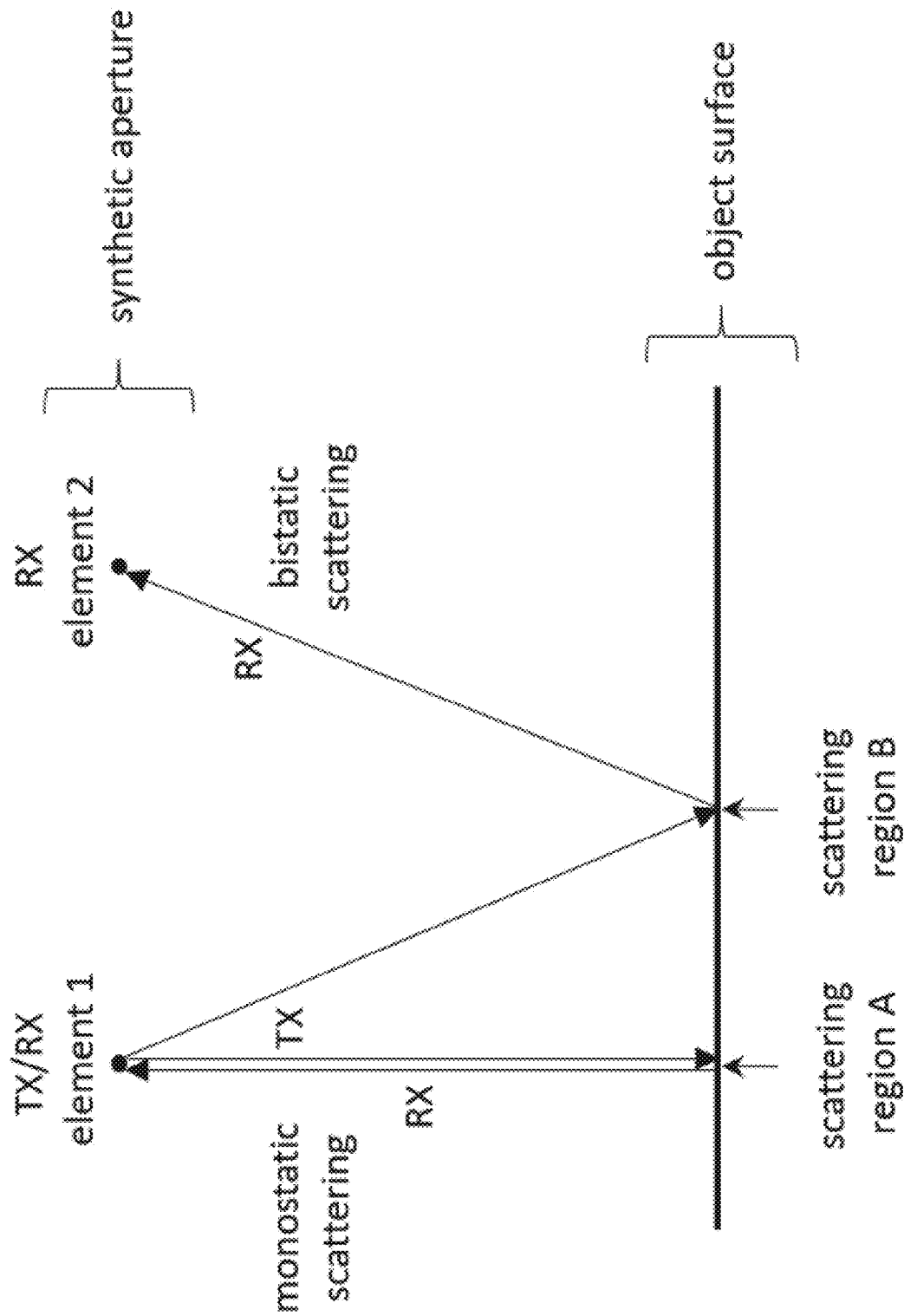
FIG. 1A illustrates a simple example of a synthetic aperture comprising a transmitter element also operating as a receiver and a separate receiving element.

The acoustic imaging techniques disclosed in this patent document can be used for various imaging applications including acoustic imaging for medical diagnostic uses and for imaging guided surgical systems where acoustic imaging information is used to provide guidance to a surgical system to locate a target surgical area and to perform the surgery. The disclosed acoustic imaging techniques may be used for high frequency acoustic imaging including viewing and imaging internal structures and functions of animals and humans. High frequency acoustic waves may be in different frequencies, e.g., between 1 and 20 MHz, or even higher frequencies, and are often termed ultrasound waves. Some factors, including inadequate spatial resolution, contrast resolution, and image signal-to-noise ratio, can lead to less than desirable image quality in ultrasound imaging, which can limit its use for many clinical indications or applications. The disclosed acoustic imaging techniques can be implemented to use tomographic and/or synthetic aperture imaging techniques to improve ultrasound image quality.

In imaging various objects, image formation may be achieved by interrogating a plurality of voxels by some means, e.g., acoustically, electro-magnetically, etc., resulting in acquisition of information from one or more measured quantities within each voxel. The information can be presented as a spatial distribution with one or higher dimensionality, which results in an image within which an object may be visualized and detected by an intelligent means. In this way, conventional medical ultrasound imaging systems, for example, utilize amplitude and phase information contained within a voxel as a result of interrogating scatterers within the voxel with a plurality of acoustic waves and processing a plurality of received echoes to summarize the information about the interrogated scatterers, typically in the form of a 2D or 3D image of an object. The systems and methods presented are applied to imaging objects in a different way compared to conventional imaging techniques.

For the purpose of image formation of an object as a whole, spatial and temporal information about the object is constructed as a problem that may be formulated differently. For example, from a set of interrogations, the imaging system can determine if and where an object is present within space using knowledge about the object and the method of interrogation. In acoustical imaging, for example, the problem may be formulated to image an object in space using a synthetic aperture imaging approach that utilizes the following: (i) a known transducer array geometry of transmitter and receiver elements in observation of an object, (ii) a known model of the object to be imaged, (iii) the waveforms transmitted and received by some combination of transmitters and receivers within the array, (iv) the processing of the received echo waveforms to simultaneously detect the object and localize the position (e.g., Cartesian coordinates) and orientation (e.g., Euler angles) of the object using a model of the object itself, and (v) a display of a representative model of the object in the form of an image.

In contemporary approaches to acoustically imaging an object in space, the processing of received echoes happens in a beamformer, which summarizes coherent information about a voxel in space centered at a point, and the object is visualized relative to the array within the image comprised of many voxels. One of the shortcomings with imaging an object in this fashion is that the object may not scatter acoustic waves with a high degree of coherence needed to visualize the object, as each voxel localizes coherent information for a point in space, which is typically not concomitant with the sum total of coherent information scattered by an object.

The challenge is that scattering from the surface or volume of an object may not be in a direction that is observable. For example, in conventional real-beam imaging using focused beams, the incident waveform arrives at the object (e.g., object's surface) from a specific direction because it is steered and focused, and the scattered waveform is returned to a specific direction or directions according to specular or other scattering from the object (e.g., surface), but there may not be a receiver or receivers in the direction or directions of the scattered waveform. In this way, imaging of the object relies solely on monostatic scattering or scattering of a component of the transmitted waveform straight back to a co-located receiver. In a synthetic transmit aperture mode of operation, the sources are unfocused or weakly focused; thus, there is a much higher chance that the scattered waveforms will arrive at a receiver because the scattered waveforms are incident at many points on the object from a range of incident directions (e.g., created by divergent wavefronts), thereby creating scattered waveforms from many points in many directions. As such, imaging of the object relies on both monostatic scattering and bistatic scattering, where bistatic scattering is scattering of the transmitted waveform towards one or more receivers that are not co-located with the transmitter. An additional challenge is that the object (e.g., surface) may exhibit complex scattering characteristics, for example, due to roughness, texture, porosity, attenuation, absorption, layers, inhomogeneities, heterogeneities, etc., that disperse and/or phase shift the scattered waveforms. Therefore, a new approach is needed to produce high-resolution surface images regardless of the position, orientation, or scattering characteristics of the surface.

In the described way of imaging an object, i.e., employing both monostatic and bistatic scattering from spatially separated and unfocused sources and receivers, the disclosed method may be viewed as a form of reflection tomography (also known as reflectivity imaging, reflectivity tomography, synthetic focusing, and diffraction tomography). In conventional reflection tomography, the region to be imaged is commonly surrounded by a circular aperture with transmitters and receivers directed inwards, i.e., approximately towards the center of the circle. For an object within the aperture, a cross-section of the object is imaged. In the case of a spatially limited set of transmitters and receivers, a small aperture is often mechanically scanned (e.g., along a circle) to synthetically create a much larger aperture. In the case of a physically large aperture (e.g., a circular aperture), but with a limited number of electrical transmitters and receivers, subapertures within the large aperture may operate with the same principle except with mechanical scanning replaced by electronic scanning, e.g., by multiplexing limited numbers of transmitters and receivers to operate a plurality of subapertures spanning the entire aperture. The resulting tomographically-generated received echoes may be processed in a number of ways, but the two primary conventional methods are (i) delay-and-sum beamforming points in space confined to the plane, and (ii) solving the inverse problem of determining the structure and/or shape of the object based on the received echoes, e.g., using methods such as filtered back-projection or radon transform inversion. A significant challenge with image formation using this method is caused by diffraction in the elevation direction of the aperture, i.e., normal to the imaging plane. Lobe energy outside the imaging plane returned by scatterers can produce artifacts within the image plane that degrade image quality. For the purpose of image formation in the plane, the scattered energy from outside of the plane is not desirable; however, knowledge of the object creating the scattered energy is useful for suppressing that energy. Going a step further, knowledge of an object is useful for imaging that object when considering the superposition (e.g., summation) of all coherent energy reflected and scattered from the object. New techniques are needed for tomographic imaging of an object, particularly for acoustic imaging.

Disclosed are systems, devices and methods for a third method of reconstructing an object using a tomographic synthetic aperture formed with the object, wherein the received echoes are coherently beamformed and processed in order to detect and localize the object with respect to the imaging aperture based on matching a known or parametrically-defined model of the object to the received echoes. In some embodiments, the disclosed systems, devices, and methods for synthetic aperture imaging of an object include techniques for beamforming echoes acquired in a synthetic aperture transmit and receive pattern in a way that employs: (i) bistatic scattering (e.g., as opposed to typical monostatic scattering) or combined bistatic and monostatic scatterings based on a model of the physical object (object model), which can be a pre-existing model stored in memory of the system or a model (e.g., parametric object model) generated in real-time and/or updated in real-time, and (ii) a model of the array (array model), which can be a pre-existing model stored in memory of the system or a model (e.g. parametric array model) generated in real-time and/or updated in real-time.

Herein, a model of a physical object (object model) refers to any possible mathematical and/or numerical definitions of scattering from a surface (surface scattering) or volume (volumetric scattering) of an arbitrary three-dimensional object in Euclidean space. While disclosed embodiments and example implementations thereof that are described herein primarily refer to surface scattering for an object model, it is understood that this is to facilitate the understanding of the underlying concepts of the present technology and that the disclosed embodiments in accordance with the present technology can also include using volumetric scattering or other scattering (e.g., internal reflections, resonances) for an object model. The object may be defined as a whole object, i.e., one object, e.g., without loss of generality, a sphere. The object may be defined as a partial whole object, i.e., a section of an object, e.g., without loss of generality, a hemisphere of a sphere. The object may also be defined as a plurality of subregions of a whole or partial object, i.e., one object comprised of multiple scattering regions, e.g., without loss of generality, a cube comprised of six sides. An object model comprised of a plurality of scattering regions may approximate a mathematical definition of the object model or it may approximate measurements of an object.

A scattering region may be a surface that is a generalization of a plane that need not be flat, i.e., its curvature need not be zero. For example, the scattering surface may be infinite, e.g., without loss of generality, an infinite plane. The scattering surface may be arbitrarily constrained in space, e.g., without loss of generality, a triangle. To facilitate calculations, a scattering surface may be summarized, e.g., without loss of generality, where a triangle may be represented as a point, unit normal vector, and an area. In this way, an object model comprised of a plurality of scattering surfaces may be summarized as a list of points, unit normal vectors, and areas.

In some example implementations, the object model may be defined parametrically, e.g., without loss of generality, where a spherical object is defined parametrically according to a radius and a 3D position coordinate. In this way, the object model may be variable, but constrained to a specific type of shape, e.g., without loss of generality, a sphere.

Herein, a model of the aperture (aperture model, array model) refers to any possible mathematical and/or numerical definitions that exactly, approximately, parametrically, and/or functionally represent the physical aperture that is operable to transmit acoustic waves and receive acoustic waves. In some implementations, for example, the aperture may be comprised of a plurality of discrete transducer elements arranged geometrically within a larger array (e.g., an array of transducers). In some implementations, for example, the elements themselves may be parametrically defined (e.g., square elements with variable area), and/or the array geometry may be parametrically defined (e.g., a circular array with variable radius).

The disclosed systems, devices and methods beamform synthetic aperture echoes received from a physical object using a model of the object to generate an image of the object, e.g., in contrast to traditional imaging (e.g., beamforming) of points in space. In some examples of the disclosed synthetic aperture object beamforming technique, bistatic scattering or a combination of bistatic and monostatic scattering from a region or regions (e.g., the surface) of the object combined with information about the synthetic aperture system is processed by the system to create an effective aperture of the imaging system with the object, e.g., by using knowledge of the object's geometry and knowledge of parameters of the system's transducer elements to produce a new kind of synthetic aperture for imaging the object.

For example, to conceptually illustrate the disclosed techniques of creating an effective aperture of an acoustic imaging system's array with the object to be imaged, consider what an optically reflective object looks like from the perspective of a finite aperture (e.g., like the aperture of a camera). From the viewpoint of the aperture, the object reflects a laterally inverted image of the aperture (e.g., a mirror reflection of a camera). For example, the reflected image may be a (laterally inverted) distorted copy of the aperture (e.g., akin to a funhouse mirror) or it may be an exact (laterally inverted) copy of the aperture (e.g., as in a flat mirror). In any case, the aperture is now inseparably linked to the object because the reflections observed by the aperture are a function of the object, the aperture, and their relative orientation. A practical example is the classic blind spot sideview mirror problem when driving a car. If the main driver cannot see the other driver's eyes in their own sideview mirror, then the other driver is in the main driver's blind spot. If one were to think about it as though the other driver's two eyeballs (i.e., an imaging aperture, e.g., of two cameras) form a synthetic aperture with their mirror (i.e., object) and the main driver's two eyeballs (i.e., a second imaging aperture, e.g., of two different cameras), then in this example, the mirror is inseparably linked to each imaging aperture through the propagation of light, and the position, orientation, shape, size, curvature, surface properties, etc. of the mirror influences the response (i.e., the image) viewed by either aperture. Continuing with this conceptual example, the driver/sideview mirror/driver problem is an example of a bistatic synthetic aperture where a mirror creates an effectively larger aperture by becoming a part of the aperture, i.e., the physical aperture, of two pairs of eyeballs, becomes a synthetic aperture with the object, that is, a sideview mirror.

The disclosed synthetic aperture object beamforming technique is different from certain implementations of real aperture imaging or other modalities of synthetic aperture imaging of an object based on imaging a plurality of points in space, where knowledge of the point locations beyond positional information contains no information about the object and no a priori information about the object (that could influence monostatic or bistatic scattering from the points). The disclosed systems, devices and methods in this patent document are designed to use the knowledge of the object and aperture in the image formation to effectuate an synthetic aperture that may be effectively larger and contain effectively more elements than the physical extent and physical number of elements in the aperture.

In some implementations, the disclosed imaging techniques beamform the object using the object model as an integral part of the beamformer, e.g., as opposed to beamforming points to form an image on a Cartesian grid or other spatial sampling, and then matching spatial information of the image to a model of the object to detect and spatially register the object within the image using registration algorithms that include, but are not limited to, correlation-based alignment, point-cloud registration, and machine learning algorithms. Importantly, the disclosed techniques can directly detect and register the object, whereas past techniques indirectly detect and register the object within an image using registration algorithms.

In the disclosed approach to image formation of an object in space, the object itself is beamformed. That is, when the received echoes from the object achieve coherence with a model of the object within the beamformer, and when the object is simultaneously localized in position and orientation, a representation of the object in the position and orientation relative to the array of transducer elements can be displayed as an image for visualization of the beamformed object. The model of the object includes any information representative of the physical object being insonified, e.g., including but not limited to physical properties (e.g., density, bulk modulus, acoustic impedance, etc.), point surfaces (e.g., topology, geometry), and/or volumetric features (e.g., material distribution, internal layers, hollow, etc.). This approach addresses a problem related to a class of problems called inverse problems, e.g., from a set of observations, calculate the causal factors that produced them. For example, from a set of waveforms measured (i.e., observed) from the reflection of a transmitted waveform, calculate the object (i.e., causal factor) that reflected the waveforms. However, the present problem is not precisely an inverse problem because the object model is an a priori quantity, i.e., the causal factor is known; whereas, in inverse problems, the solution is to determine the object that caused a set of observations. More precisely, the solution to the proposed problem is a fitting optimization problem in a high dimensional space of time domain echoes constrained by a model of the array, a model of the object, a spatial transformation relating the array model and object model, and the propagation and diffraction of sound waves.

The proposed problem of object imaging and localization may also be viewed in the context of a spatial filtering problem. The function of a beamformer is to spatially filter echoes in order to localize information corresponding to a particular location or point in space relative to a transducer array. Instead of spatial filtering for localizing information at a point in space (i.e., a point spatial filter), spatial filtering may be applied to localize information about an object in space (e.g., an object spatial filter). Here, the spatial filter is a function of the object model, its position, its orientation, the array model, the position of the array model, the orientation of array model, and/or transmission and/or scattering parameters derived from (i) the object model, (ii) the physics of diffraction, (iii) the physics of scattering, (iv) the physics of acoustic wave propagation, and/or (v) the physics of electromechanical transduction. To differentiate an object spatial filter from a point spatial filter throughout this disclosure, the object spatial filter is referred to henceforth as an object beamformer.

The object spatial filter (object beamformer) may also be viewed as a type of matched filter whereby, when the trial relative position and orientation of a model of the array of transducer elements (i.e., array model) and the model of the physical object (i.e., the object model), both contained in the object beamformer, match the true relative position and orientation of the physical array and the physical object, the output of the object beamformer is maximized, and the physical object is matched and detected.

In some embodiments, an acoustic imaging system configured to beamform echoes from an object and produce an image thereof, where the acoustic imaging system is comprised of a transducer array, transmitter and receiver circuitry, a data processing device that includes an object beamformer module incorporating a model of the object and a model of the transducer array, a processing module to find the optimal solution to the object fitting problem, and a control module for sequencing synthetic aperture transmissions and receptions. In some embodiments, the acoustic imaging system may optionally include a display device for visualizing an image of the object with respect to a known or reference coordinate system (e.g., the coordinate system of the array model).

In some embodiments, a method for beamforming echoes from a physical object and producing an image of the object, using an acoustic imaging system, involves manipulating a model of the array through optimization of position and orientation applied to transmitter and receiver coordinates using a homogenous transformation matrix, or any equivalent series of spatial transformations, where the manipulations, e.g., rotations and/or translations, applied in the object model frame-of-reference optimize the output of an object beamformer utilizing said array model and object model. Similar, functionally equivalent embodiments involve manipulating a model of the object (instead of the model of the array) through optimization of position and orientation applied to the object model coordinates using a homogeneous transformation matrix, or any equivalent series of spatial transformations, where the manipulations, e.g., rotations and/or translations, applied in the array model frame of reference optimize the output of an object beamformer utilizing said array model and object model. For example, a common set of parameters include the relative position and orientation of the array model and the object model, which may be viewed from either the array model frame of-reference or the object model frame of reference.

FIGS. 1A-1D show diagrams illustrating an example implementation of tomographic synthetic aperture imaging and object beamforming technique in accordance with the present technology.

FIG. 1A illustrates the concept of an example synthetic aperture implementable by the disclosed systems and methods for two spatially separated transducer elements in one dimension, without loss of generality to more than one dimension. In the example, element 1 is both a transmitter and a receiver, and element 2 is operating only as a receiver. Both elements are assumed to be point sources/receivers such that they emit spherical wave fronts, and thus, raytracing shown as arrows suffices to illustrate representative scattering paths. For the one-dimensional object surface shown, transmission on element 1 results in a received echo from scattering region A on element 1 and a received echo from scattering region B on element 2. The echo received on element 1 is the result of monostatic scattering and the echo received on element 2 is the result of bistatic scattering. It is shown that the aperture created by reception on element 2 is much larger compared to the aperture created by transmission and reception only on element 1. In this way, a synthetic aperture is created. More transmitter and/or receiver elements may be added to further extend the synthetic aperture, for example, to enclose or partially enclose the object to be imaged. Here, for example, an advantage of the synthetic aperture is that a relatively large aperture may be formed from relatively few transducer elements.

Figure 1B:
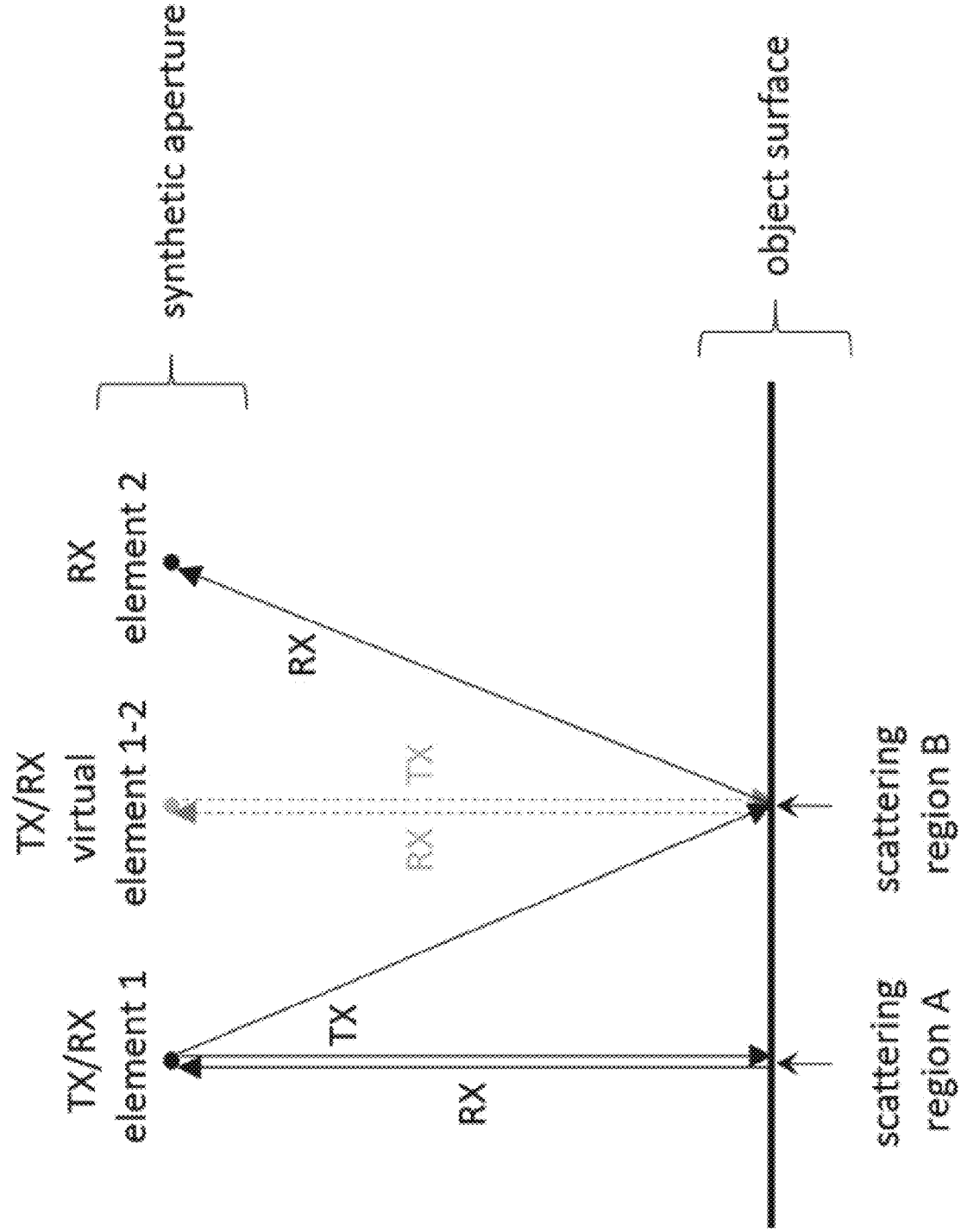
FIG. 1B illustrates the concept of a virtual element created with a synthetic aperture.

FIG. 1B illustrates a synthetic aperture sensing operation using the same hardware shown in FIG. 1A, by adding a processing using the creation of a virtual element between elements 1 and 2, which monostatically samples scattering region B with a normal incidence as compared to the bistatic sampling created by elements 1 and 2. Assuming that the scattering is independent of incidence angle, for example, information from scattering region B would be largely the same for monostatic and bistatic sampling. In this way, the synthetic aperture comprised of transmitting on element 1 and receiving on elements 1 and 2 is effectively the same size as if transmitting and receiving on element 1, followed by transmitting and receiving on an element in the location of virtual element 1-2. Stated differently, the aperture created by receiving on element 2 is physically extended by some fraction of the distance from the transmitting element to the receiving element, in this case, by exactly half.

Figure 1C:
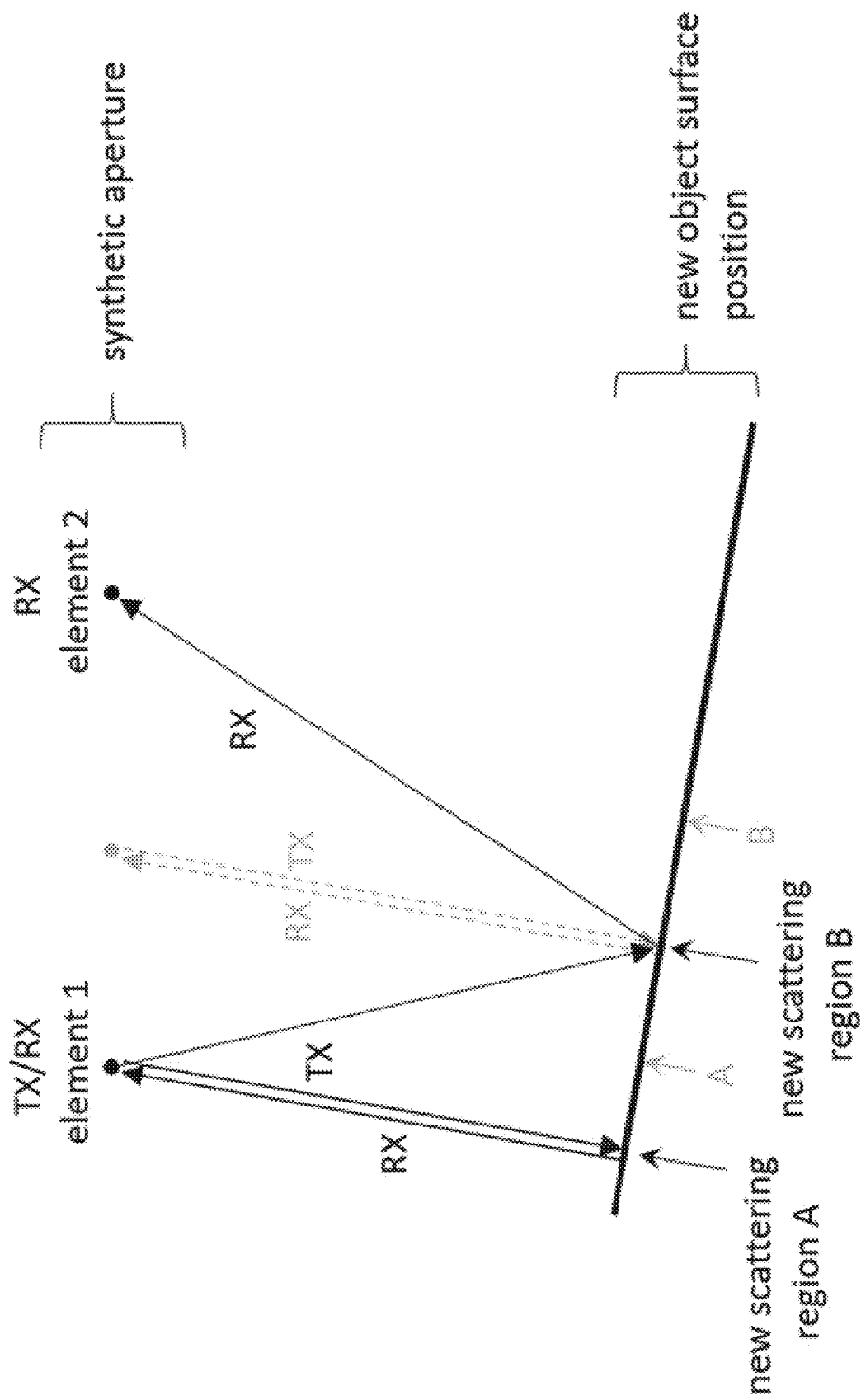
FIG. 1C illustrates the concept of spatial sampling on the surface of an object as a function of a change in position of the object as compared to FIG. 1A.

FIG. 1C illustrates a simple rotation of the object surface by 10 degrees as compared to the geometry shown in FIG. 1B to show the change in position of the scattering regions A and B on the object surface and the resulting change in the virtual element position, which is no longer half the distance between elements 1 and 2 as shown in FIG. 1B. In this way, the effective synthetic aperture created by transmitting on element 1 and receiving on elements 1 and 2 is inseparably tied to the object shape, position, and orientation, and the resulting synthetic aperture is said to be formed with the object. While some definitions of a synthetic aperture are generally considered to be independent of the target, e.g., a synthetic aperture as combined with a beamformer, in accordance with the present technology, is operable to localize coherent energy at points in space that may or may not be coincident with the surface of an object. In accordance with the disclosed technology, the synthetic aperture combined with a beamformer is operable to detect and localize an object according to coherent energy scattered from the surface of an object.

Figure 1D:
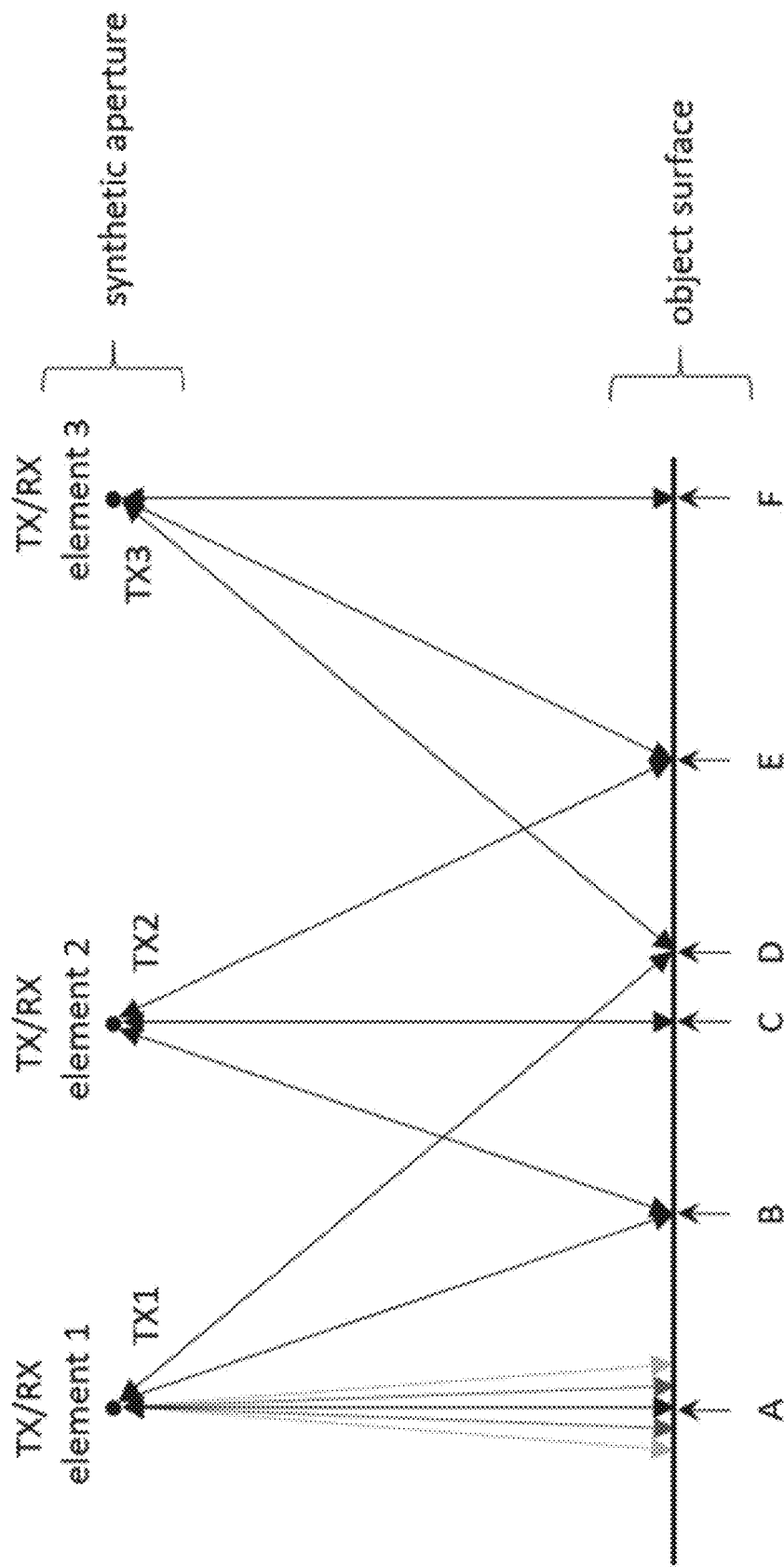
FIG. 1D illustrates the concept of a synthetic aperture, including three elements operating as both transmitters and receivers, that samples six spatially separated scattering regions labelled "A"-"F" on the surface of an object.

FIG. 1D illustrates an example of a full transmit synthetic aperture for three spatially separated transceiver elements operable for both transmission and reception. In full synthetic transmit aperture, for example, a transmission event occurs on transceiver element 1, followed by reception on all three transceiver elements, followed by transmission on transceiver element 2 followed by reception on all three transceiver elements, and lastly, transmission on transceiver element 3 followed by reception on all three transceiver elements. In this way, three monostatic scattering regions on the object surface labeled A, C, and F are sampled, and three bistatic scattering regions on the object surface labeled B, D, and E are sampled. Likewise, the number of unique samples of the object surface may be increased by increasing the number of transmitters and/or receivers.

Furthermore, as illustrated in the example of FIG. 1D, regions A-F are comprised of an infinite number of infinitesimal scattering points, each contributing, through acoustic diffraction, a component to echoes received by each of the three transceiver elements for each transmission. In this fashion, there is a dramatic multiplication of the scattering paths when all such paths are considered, which is illustrated for five locations comprising scattering region A. For each illustrated scattering path for region A, there is a diminishing gradation of the grayscale of the path indicating diminishing echo strength as the incident angle deviates from 0 degrees. Thus, it is the monostatic and/or bistatic scattering created by a synthetic aperture comprised of separated transmitters, receivers, and/or transmitters and receivers combined with scattering paths described by the geometry of the object model that are considered in the disclosed method for imaging an object. In this example, given five samples of the object surface per scattering region, the number of scattering paths increases from 6 to 30 for this simple one-dimensional object surface. An equivalent two-dimensional object surface could be represented with 25 samples per scattering region, resulting in 150 scattering paths for a synthetic aperture comprised of three spatially separated physical elements. As such, the disclosed synthetic aperture technology is integrated with the object beamformer technology as discussed and illustrated in example embodiments, below.

In the examples disclosed in this patent document, the use of "synthetic aperture" and "synthetic aperture array" and "synthetic aperture technology" and the like refers to (i) the physical aperture and/or physical array operable in accordance with synthetic aperture techniques (e.g., including, but not limited to, synthetic transmit aperture imaging, unfocused transmission, unfocused reception), and/or (ii) any virtual apertures and/or virtual arrays derivable from physical apertures and/or physical arrays and created in accordance with synthetic aperture techniques, and/or (iii) any virtual apertures and/or virtual arrays created with the object in accordance with synthetic aperture techniques applied to physical apertures and/or physical arrays, and (iv) any spatial sampling on an object created by physical and/or virtual apertures and arrays in accordance with synthetic aperture techniques.

In some embodiments, an object beamformer may be embodied as a hardware and/or software module of a computing device, which comprises instructions executable by a computer processor and memory to compute echo delays and weights according to surface scattering based on the array model coordinates and a model of the object, where some combination of linear and nonlinear operations applied to delayed and weighted echoes produce one or more beamformed echoes as outputs to the object beamformer.

The output of the object beamformer can be processed by the computing device to integrate the power of the beamformer echo(es) within a time window; the duration of which is proportional to the time duration of the two-way impulse response of the acoustic imaging system. A data processing unit (e.g., including a computer processor and memory), which can be embodied on the computing device, can be configured to determine the position and orientation of the array coordinates utilized within the object beamformer by varying parameters to maximize the beamformed echo power using an optimization algorithm, e.g., stored in the memory of the data processing unit.

The optimized position and orientation of the array can be used to generate a display of the object in the frame of reference of the array such that the object may be visualized, for example, on a display unit in communication with the computing device or a display component of a user interface of the computing device. Additionally, the position and orientation of the object together with a model of the object may also be displayed or output for use. For example, in some implementations of the disclosed systems and methods for synthetic aperture beamformed object imaging (also referred to as synthetic aperture object imaging (SAOI)), the position and/or orientation data associated with particular points or regions of the object's surface can be precisely identified, e.g., with respect to the frame of reference of a transducer array operable as a synthetic or real aperture. The identified position and/or orientation of one or more points or regions of the object's surface can be implemented with periodic position and/or orientation updates within the frame of reference.

In various implementations, the disclosed systems and methods are primarily intended for imaging objects that have a significant impedance difference such that specular reflections from the surface of the object are achieved. For example, the system and method may be applied to imaging any kind of tissue and/or imaging implantable objects with reflective and/or scattering features that aid detection and discrimination from surrounding hard or soft matter. For example, an array and an object may be co-designed such that the array takes full advantage of specularly reflective surfaces of a particular object designed to scatter in specific directions in the frame of reference of the object.

In addition to specular reflections, also known as unscattered reflections and specular scattering, there are also scattered reflections also known as diffuse reflections (e.g., Lambertian reflections) and non-specular scattering. Varying degrees of scattered and unscattered acoustic reflections are possible for an object, primarily dependent on (a) the size of the object relative to a wavelength, and (b) the size of features on the surface of the object relative to a wavelength. Objects much smaller than a wavelength exhibit Rayleigh scattering, where the scattered waves from a collection of such objects arrive at a point in space with a random collection of phases. Objects on the order of a wavelength produce Mie scattering, which cause interference effects in the scattered waves due to phase variations over the surface of the object. The disclosed technology has a primary application to objects equal to or larger than a wavelength and such objects with surface features equal to or larger than a wavelength; however, without loss of generality, the disclosed systems, devices, and methods may be applied to objects that produce both unscattered and scattered acoustic reflections. The general term for both types of scattered wave, specular and diffuse, is referred to henceforth and interchangeably as reflection and scattering unless one or the other component is referred to specifically, e.g., specular reflection.

Figure 1E:
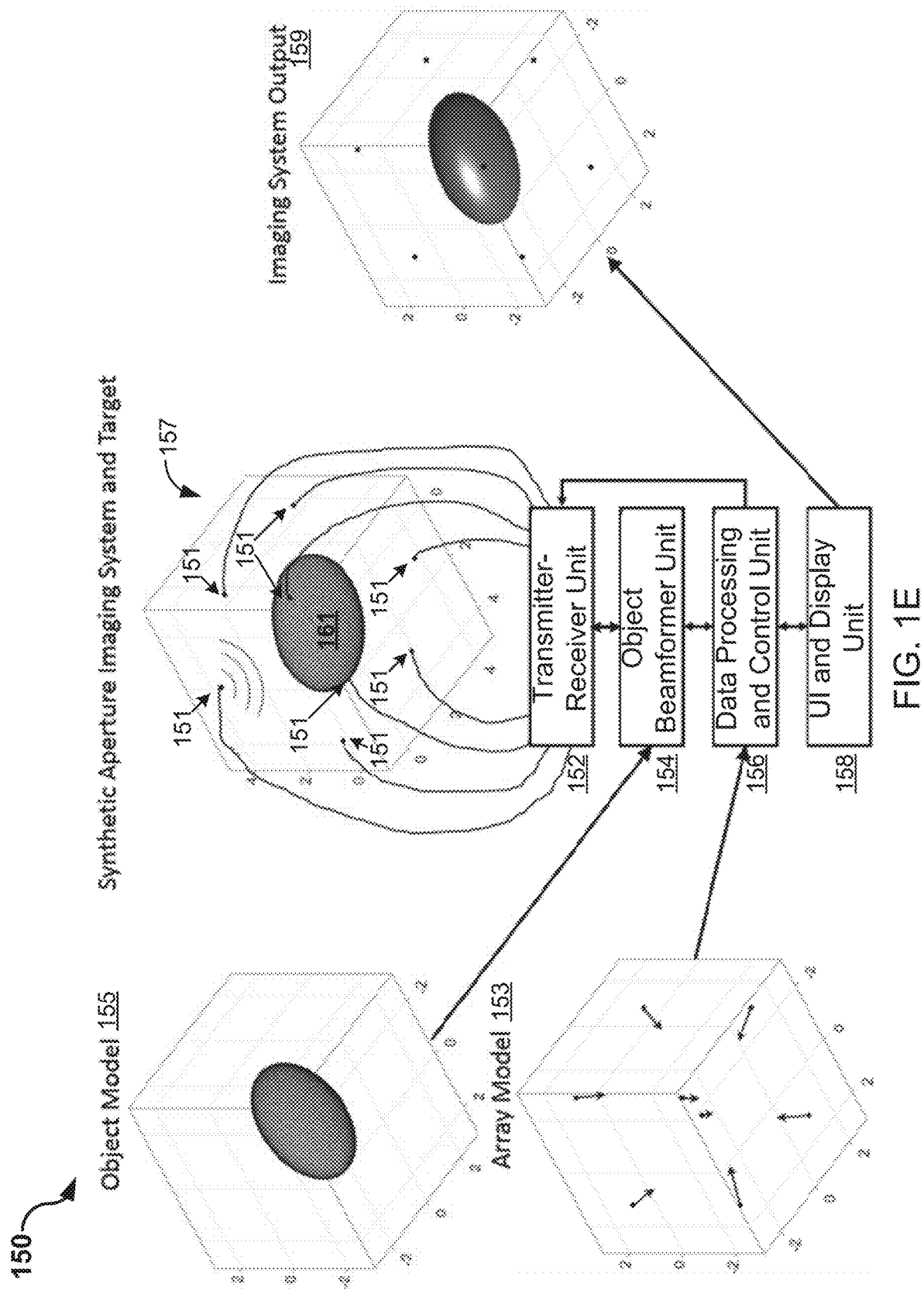
FIG. 1E shows a diagram illustrating an example embodiment of a tomographic synthetic aperture ultrasound system in accordance with the present technology.

FIG. 1E illustrates an example embodiment of a synthetic aperture ultrasound system 150 in accordance with the present technology. The system 150 includes a synthetic aperture array that is comprised of a plurality of acoustic transducer devices 151 (e.g., positions shown as eight points in plot 157 of FIG. 1E arranged in three-dimensional space with respect to an object 161), which can be configured as transmitting transducers, receiving transducers, and/or transmitting-receiving transducers or acoustic transceivers (configured to transmit and receive acoustic signals). Each acoustic transducer device of the plurality of acoustic transducer devices 151 may include an array matrix of different transmitting or receiving acoustic transducer elements, and the collection of the acoustic transducer devices 151 can be implemented to form a transmitter-receiver unit as a synthetic aperture array for improving the imaging of the object 161. The system 150 includes a transmitter-receiver unit 152 interfaced to the synthetic aperture array, which the transmitter-receiver unit 152 is configured to generate and drive transmitted waveforms on specific array elements and to receive echoes on specific elements and convert the signals to the digital domain. The acoustic transducer devices 151 are placed at known positions in space relative to the target object and certain relative positions with respect to one another within the synthetic aperture array for directing acoustic waves to the target object and to receive acoustic signals from the target object for imaging. Depending on applications, the acoustic transducer devices 151 may be in fixed positions in some imaging system designs and, in other imaging system designs, they may be placed on one or more actuated arms or frames to allow their positions and relative positions within the synthetic aperture array to be adjusted. Various motion actuators and rotating devices may be used.

Figure 1H:
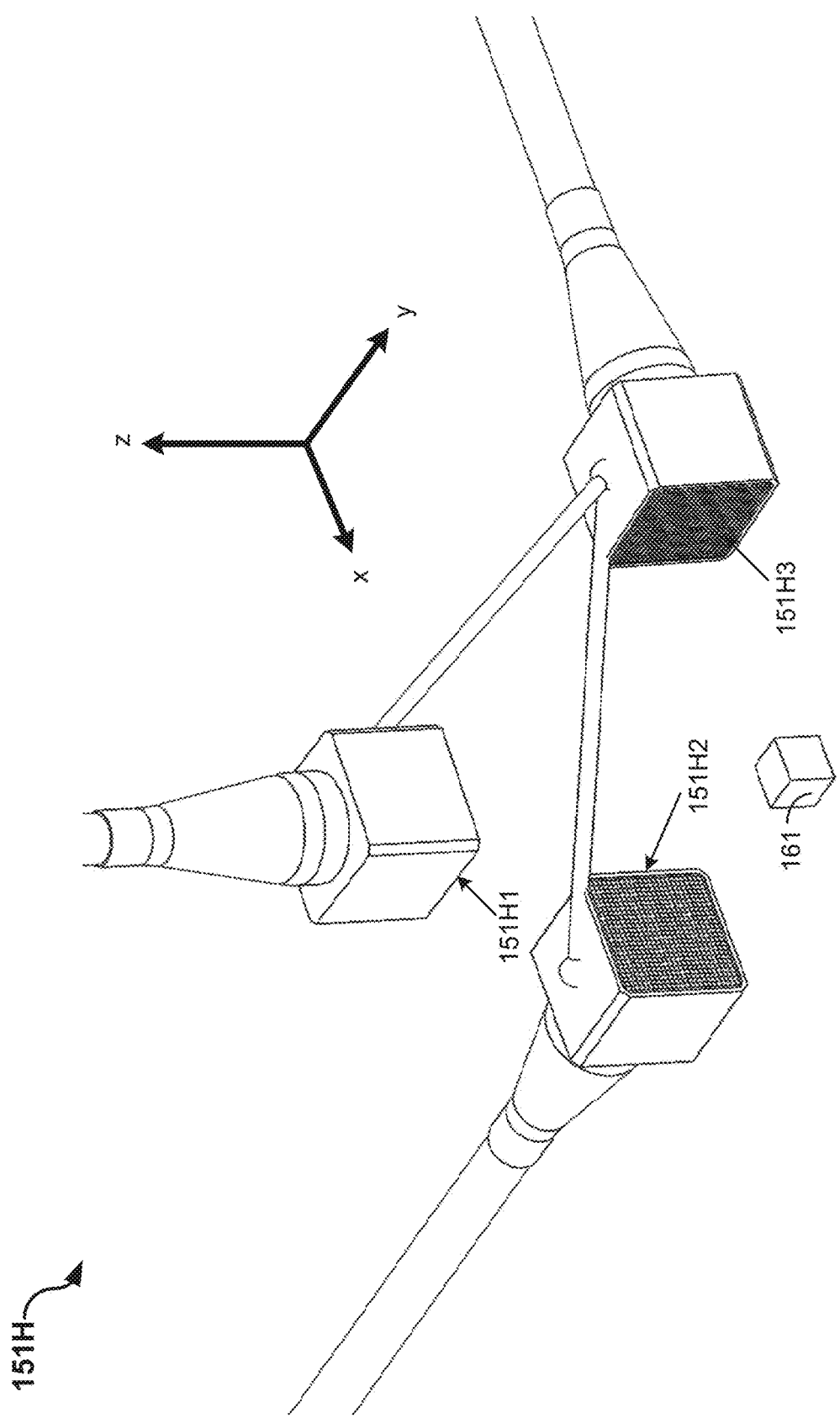

FIGS. 1F-1H show diagrams illustrating example embodiments of arrays of acoustic transducer devices 151 of the example synthetic aperture ultrasound system 150, which can be include transducer array segments, for imaging the target object 161. In these examples, each acoustic transducer device 151 includes a two-dimensional array of acoustic transmitting or receiving or transmitting-receiving acoustic transducer elements. The object 161 can be any object with at least three determinable degrees-of-freedom.

FIG. 1F shows an example embodiment of an array of acoustic transducer devices 151F that includes eight rigidly connected transducer array segments 151F1, 151F2, . . . 151F8, arranged along the eight points of a cube surrounding the object 161, where each transducer array segment is directed at the object 161. The array of acoustic transducer devices 151F includes connection structures 192F1, 192F2, . . . 192F8 that electrically connects the transducer array segments 151F1, 151F2, . . . 151F8, respectively, to the transmitter-receiver unit 152. In some embodiments, for example, the connection structures 192F1, 192F2, . . . 192F8 include a rigid frame, housing, or casing, such that the respective transducer array segments 151F1, 151F2, . . . 151F8 may not move with respect to the 192F1, 192F2, . . . 192F8. The array of acoustic transducer devices 151F can optionally include a rigid structure 191F, which rigidly couples at least some of the transducer array segments 151F1, 151F2, . . . 151F8. In some embodiments, for example, the array of acoustic transducer devices 151F can include positioning systems (e.g., motorized stepper, etc.) that can move the three-dimensional position of some or all of the transducer array segments 151F1, 151F2, 151F8 with respect to another transducer array segment and/or with respect to the object 161. In example implementations, for example, depending on the object and orientation relative to the array of acoustic transducer devices 151F and the repositioning of the transducer array segments 151F1, 151F2, . . . 151F8, the array of acoustic transducer devices 151F is able to be used by the system 150 to determine six degrees-of-freedom for an ellipsoid (e.g., as shown in the diagram of FIG. 1F). During such implementations of the system 150, the number of individual transducer elements selected for transmit and/or receive, the geometry, the orientation, etc. of the transducer array segments 151F1, 151F2, . . . 151F8 are known to the system 150 with respect to a frame of reference. In some implementations of the example array of transducer devices 151F, for example, functionally, one single array element from each of the segments 151F1, 151F2, . . . 151F3 could be represented by the point sources and receivers.

FIG. 1G shows an example embodiment of an array of acoustic transducer devices 151G that includes three rigidly connected transducer array segments 151G1, 151G2, 151G3, arranged along the three points surrounding the object 161, where each transducer array segment is directed at the object 161 so that three rigidly connected transducer array segments 151G1, 151G2, 151G3 face the object 161 at three different directions. In example implementations, for example, depending on the object and orientation relative to the array of acoustic transducer devices 151G and the repositioning of the transducer array segments 151G1, 151G2, 151G3, the array of acoustic transducer devices 151G is able to be used by the system 150 to determine at least three degrees-of-freedom for a spherical object (e.g., as shown in the diagram of FIG. 1G) and as many as six degrees-of-freedom for other types of objects (e.g., cube, ellipsoid, etc.).

FIG. 1H shows an example embodiment of an array of acoustic transducer devices 151H that includes three rigidly connected transducer array segments 151H1, 151H2, 151H3, arranged along the three perpendicular planes xy, xz, and yz, respectively, that surround the object 161 (e.g., in this example, a cube object), where each transducer array segment is directed at the object 161. In example implementations, for example, depending on the object and orientation relative to the array of acoustic transducer devices 151H and the repositioning of the transducer array segments 151H1, 151H2, 151H3, the array of acoustic transducer devices 151H is able to be used by the system 150 to determine six degrees-of-freedom, e.g., for a cube with an array segment pointing at three orthogonal faces.

In some embodiments, for example, one or more rigid rods or frames for connecting and holding different acoustic transducer devices 151 in the examples in FIGS. 1F, 1G and 1H may be replaced by one or more adjustable rods or frames or combinations of rigid rods or frames with actuators to allow their positions and relative positions to be adjusted for accommodating different target objects in different shapes. In such designs, the positions in space relative to the target object and certain relative positions of the acoustic transducer devices 151 are known once their positions and orientations are adjusted to desired positions and are fixed.

In example implementations, for example, the example array of transducer devices 151F, 151G, and 151H include various array segments comprising various combinations of transducer elements across one or more sub-arrays, which can be utilized to generate a variety of acoustic waveforms to be transmitted at the object 161, e.g., including coded acoustic waveforms for generating one or more composite acoustic waveforms (e.g., ultrasound beam(s)).

Figure 1I:
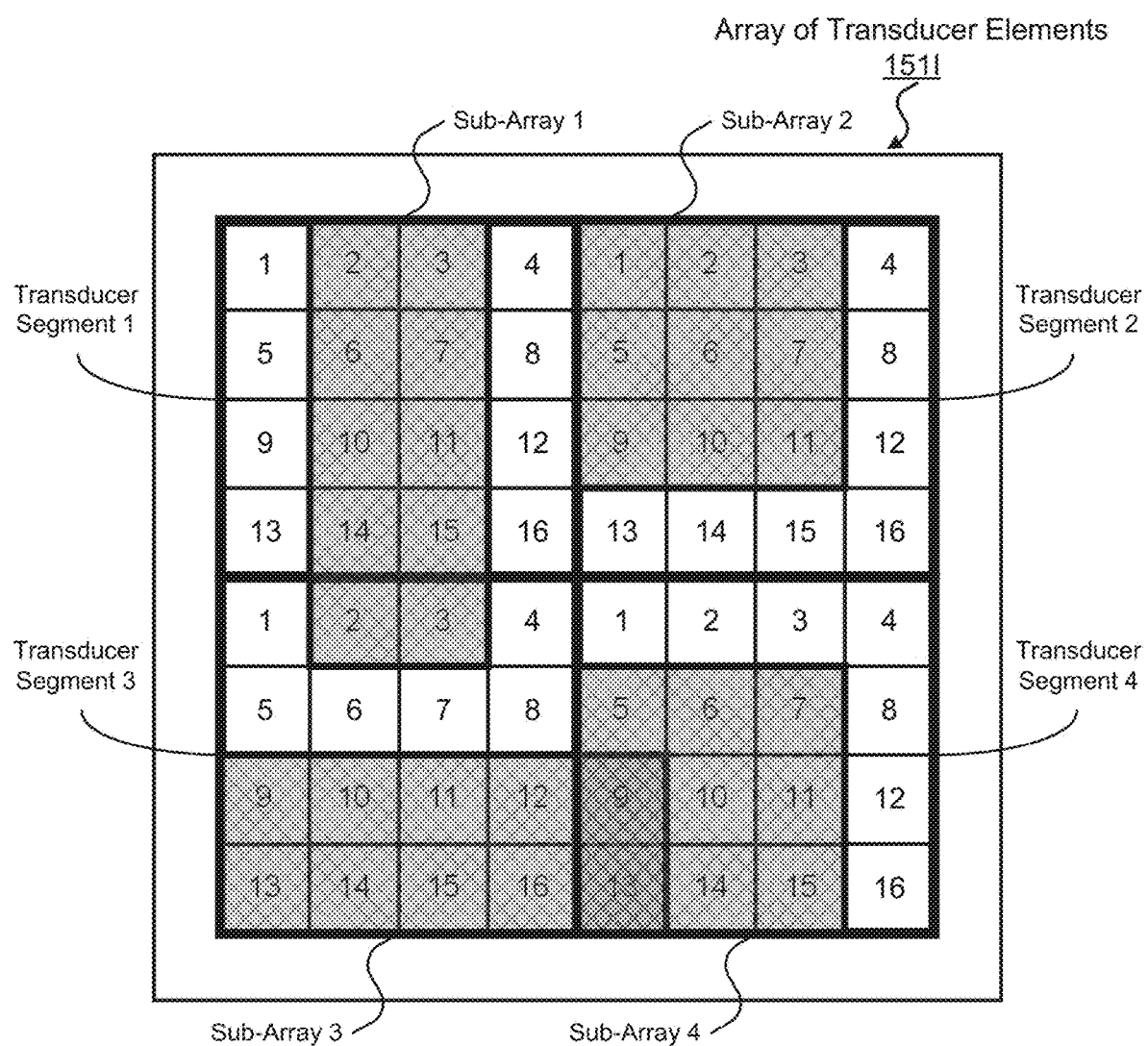
FIG. 1I shows a diagram illustrating an example embodiment of transducer array segments of an example array of transducer elements, in accordance with the present technology.

FIG. 1I shows a diagram illustrating a non-limiting example of the transducer array segments of the example array of transducer devices 151F, 151G, and 151H, shown in the diagram as array of transducer segments 151I. In this example, the array of transducer segments 151I includes 64 individual transducer elements arranged in four transducer segments (e.g., transducer segment 1, 2, 3, and 4). While the diagram illustrates the four transducer segments spatially proximate, it is understood that the four transducer segments may be arranged spatially separated, e.g., including on separate, rigidly connected transducer segments like in FIGS. 1F, 1G, and 1H. In this example of FIG. 1I, one or more sub-arrays, comprising any of the 64 individual transducer elements (e.g., including transducer elements among one or more of the four transducer segments), can transmit (e.g., either sequentially, simultaneously or randomly) the individual acoustic waveforms (e.g., including individual coded acoustic waveforms). A sub-array can include combinations of the individual transducer elements in one transducer segment or among a plurality of the transducer segments. For example, a sub-array 1 includes transducer elements 2, 3, 6, 7, 10, 11, 14 and 15 of transducer segment 1 and transducer elements 2 and 3 of transducer segment 3; a sub-array 2 includes transducer elements 1, 2, 3, 5, 6, 7, 9, 10, and 11 of transducer segment 2; a sub-array 3 includes transducer elements 9, 10, 11, 12, 13, 14, 15, and 16 of transducer segment 3 and transducer elements 9 and 13 of transducer segment 4; and a sub-array 4 includes transducer elements 5, 6, 7, 9, 10, 11, 13, 14, and 15 of transducer segment 4. Configurations of the sub-arrays can be produced using a switching element (e.g., such as a multiplexer unit), which can be included in the transmitter-receiver unit 152 in some embodiments.

Referring back to FIG. 1E, the system 150 includes an object beamformer unit 154 that is implemented on a computing device comprising one or more processors in communication with one or more memory devices, e.g., random-access memory (RAM). The output(s) of the transmitter-receiver unit 152 are communicated to the object beamformer unit 154, which is configured to utilize a model of the object (illustrated as object model 155) to be imaged in conjunction with information about the array geometry for determining echo delay and weight calculations prior to a coherent combination within the object beamformer, contained within the object beamformer unit 154.

The system 150 includes a data processing and control unit 156 (e.g., sometimes referred to as a data processing unit) comprising a processor and memory in communication with the object beamformer unit and the transmitter-receiver unit. In some embodiments, the object beamformer unit 154 is configured on the same computing device as the data processing and control unit 156; whereas in other embodiments the object beamformer unit 154 is configured on a separate computing device in communication with a computing device comprising the data processing and control unit 156. The data processing and control unit 156 is configured to adjust parameters describing the position and orientation of the array geometry relative to the model of the object, illustrated as array model 153, such that the object beamformer output is maximized (described in detail below). The data processing and control unit 156 is configured to control the transmitter-receiver unit 152 for sequencing transmissions and reception of acoustic signals.

In some implementations of the disclosed system and methods, for example, detection of the object occurs when the data processing and control unit 156 determines a match between a set of received synthetic aperture echoes beamformed in the object beamformer unit 154, the model of the object, the model of the array, and/or the position and orientation of the array relative to the model. In some implementations, for example, the decision for whether or not a match is achieved is determined by comparing one or more inputs and/or outputs (e.g., variables) or changes in one or more inputs and/or outputs (e.g., different changes between iterations), of an optimization process seeking a match, to one or more thresholds. Determining the values of the one or more thresholds may be based on empirical data, simulated data, Monte-Carlo methods, perturbation theory, and/or a number of statistical methods or detection theory methods for determining threshold values (e.g., including but not limited to statistical hypothesis testing, t-tests, receiver operating characteristics for binary classifiers, Bayesian hypothesis testing, etc.). The one or more thresholds and the conditions required of one or more variable inputs and/or outputs of an optimization process (e.g., input or output greater or less than a threshold) are sometimes referred to herein as detection criteria. For a numerical optimization, for example, such criteria may be referred to as tolerances (e.g., thresholds) or stopping criteria (e.g., when a threshold is crossed and the optimization process stops). Herein, detection criteria and stopping criteria are referring to the same criteria for detecting an object based on conditions applied to inputs and/or outputs of an optimization process. In implementations of the disclosed methods and systems involving a numerical optimization, for example, at the core of the optimization process is an algorithm responsible for searching for a solution that maximizes or minimizes an objective function. The optimization algorithm referred to herein is also known as a solver or an optimizer. Also, the specific algorithm responsible for finding the solution may be referred to as a solver or an optimizer. Many types of optimizers exist, and they are broadly categorized as either linear or nonlinear optimizers. In some embodiments in accordance with the present technology, a nonlinear optimizer is used to solve for a set of parameters that are varied until a match is found, i.e., one or more detection criteria are satisfied. More about the optimization process is discussed later, below.

In some embodiments, the system 150 may include a user interface (UI) and display unit 158 to facilitate user input to the system 150 and present a produced output 159 (e.g., an image of the physical object), according to parameters describing the object, including but not limited to position and/or orientation of the object, produced by the data processing and control unit 156 working in conjunction with the object beamforming unit 154 and transmitter-receiver unit 152.

In some embodiments of the system 150, for example, the transmitter-receiver unit 152 is configured to operate an array of multiple transducer element positions that surrounds an object and is operable to produce a sparse aperture, i.e., an aperture area with large voids and one or more instances of large physical separation between elements, where separations are typically larger than one wavelength.

In the example of FIG. 1E, there are eight transducer element positions to produce the sparse aperture. The exact geometrical placement of the eight transducer elements, shown as a cube, is not required; but it is required that the multiple transducer elements fully or at least partially surround the object and that the elements largely point towards the object, e.g., the surface normal vectors of the array elements are parallel with at least one surface normal direction on the object. In this way, the aperture may effectively work as a much larger aperture, but with very few elements (e.g., a sparse aperture) compared to an aperture that would fully surround the object.

In the example of the array model 153 shown in FIG. 1E, for example, when a surface normal of the array element (shown as an arrow emanating from each element position) is parallel with at least one surface normal, then a monostatic scattering is expected, i.e., a reflection directly back to the transmitting element. Bistatic scattering occurs when a transmission from one element is reflected in the direction of a second element. The point or region on the object where a monostatic or bistatic reflection originates creates a reflection sampling location on the surface of the object. The total number of elements is important because, depending on the shape of the object, there must be at least three to six total unique monostatic or bistatic reflection samples of the object with significant separation in order to determine the object's determinable position and/or determinable orientation in space. It is possible to have bistatic samples and monostatic samples overlap, thus the need for significant separation between elements or significant numbers of monostatic and bistatic samples such that despite redundancy in sampling, and depending on the shape of the object, at least three to six effectively unique samples of the object are produced. For example, a spherical object has determinable position but indeterminable orientation, thus requiring at least three unique samples to determine the object's position. Other types of objects have both determinable and indeterminable degrees-of-freedom, including, but not limited to, e.g., right cylinders, infinite cylinders, cones, and ellipsoids. As a general requirement for arbitrary objects with both determinable position and orientation, for example, at least six unique samples of the object are required to determine the object's position and orientation. Exceptions include, but are not limited to, e.g., cubes, rectangular prisms, tetrahedrons, and right pyramids, which have determinable position and orientation from fewer than six samples.

In the example arrangement shown by the example embodiment of the system 150 in FIG. 1E, there are at least eight monostatic samples, i.e., transmission on element index, i, and reception on the same element index, i. The number of bistatic samples, i.e., transmission on element index i and reception on element index j, such that j is not equal to i, depends on the position and orientation of the object with respect to the array and the shape of the object such that a transmission on element index i will generate a reflection into element index j. In other words, for an 8-element array, there are 28 bistatic samples of the object, but several of the bistatic samples are irrelevant because no reflection is possible.

As shown in FIG. 1E, the transducer elements are connected to transmitter devices and/or receiver devices of the transmitter-receiver unit 152, which contains at least one transmitter channel and at least one receiver channel that are multiplexed across all 8 elements. In some embodiments, for example, the transmitter-receiver unit 152 contains 8 transmitter channels and 8 receiver channels so that multiplexing is not required. In some implementations, for example, the transmitter-receiver unit 152 drives the transducers using analog amplifiers or digital amplifiers to create unfocused acoustic waveforms with fractional bandwidths of at least 1%, but preferably with bandwidths of greater than 50%. The waveforms may have low or high time-bandwidth products, for example a Gaussian-shaped waveform with a low time-bandwidth product or a coded waveform such as a linear frequency modulated chirp waveform with a high time-bandwidth product. Here, depending on the closest distance from the element to the target, a long duration waveform may fold onto itself, i.e., it may still be transmitting when the first echo from the beginning of the waveform is received. Here, the duration must be decreased so that transmission does not overlap reception, i.e., the physical length of the waveform in the medium is less than the shortest round-trip distance from the array element to the object back to the receiver element.

In various embodiments of the system 150, for example, the transducer elements of the transmitter-receiver unit 152 may be constructed from lead zirconate titanate (PZT), polyvinylidene fluoride (PVDF), capacitive micromachined ultrasonic transducer (CMUT), piezoelectric micromachined ultrasonic transducers (PMUT), or any other piezoelectric material or device that converts electrical energy to mechanical energy and vice versa. The transmitter channels in the transmitter-receiver unit 152 are operable to drive the transducers with electrical waveforms, producing acoustic waveforms. The receiver channels in the transmitter-receiver unit are protected from the transmitters using required circuitry including but not limited to diode expanders and limiters, high voltage switches, transformers, and diplexers. The receiver channels are operable to amplify and filter received echo signals, but may also perform other operations, such as microbeamforming or beamforming in the analog domain wherein analog sampling and summation is used to combine analog signals from multiple channels.

The transmitter-receiver unit 152 can include circuitry and electronic components including, but not limited to, power amplifiers, RF amplifiers, variable gain amplifiers, diplexers, multiplexers, digital-to-analog converters, analog-to-digital converters, mixers, demodulators, detectors, ASICs, FPGAs, DSPs, RF transformers, analog filters, digital filters, Ethernet circuitry, PCI circuitry, digital buffers, RAM, nonvolatile memory, communication components, analog busses, digital busses, switches, and power supply electronics. The circuitry and electronic components of the transmitter-receiver unit 152 are communicatively coupled to the transducer elements and to the data processing unit of the system 150.

In some implementations, for example, the received echo signals are amplified and converted to digital signals using a sampling rate high enough, at least two times the highest frequency component, to satisfy the Nyquist sampling theorem and a quantization bit depth such that valid but weak echoes are discernable from noise. In some implementations, for example, an analog anti-aliasing filter may precede the digital conversion to guarantee satisfaction of the Nyquist sampling theorem.

In some implementations, for example, the transmitter-receiver unit 152 receives sequencing information from the data processing and control unit 156. The control unit within the data processing and control unit 156 communicates information about which element or elements to transmit on and which receiver or receivers to receive on and convert to digital signals. In addition to which elements are used, the sequencing information also contains timing information, for example, a transmission delay(s) and reception delay(s). For example, a transmission may occur on element 1 after a defined delay and a second transmission may occur on element 2 after a defined delay. On reception, the analog-to-digital (ADC) conversion on element 1 starts after a defined delay and likewise for element 2.

In some embodiments of the system 150, for example, the array of transducer elements may each include a collection of transducer elements, such that they operate as a virtual transmitter and/or a virtual receiver—notably, which is different than with virtual apertures and virtual arrays discussed above in relation to synthetic aperture technology. In this case, the delays on each element must be independently controllable via a transmit beamformer to facilitate a virtual source point and/or via a receive beamformer to facilitate virtual a receiver point from which the wave front appears to originate and/or be observed, respectively. Since virtual elements are comprised of more than one physical element, for example, they are advantageous for increasing the transmitted energy on transmission and gain on reception such that the overall signal-to-noise ratio is improved as compared with using single elements for transmission and reception. For example, functionally, the system 150 operates with virtual sources and receivers in the same way that it operates with single element sources and receivers, albeit with more complexity within the receiver and the object beamformer unit 154 to accommodate the additional signals and ADC channels.

In some embodiments of the system 150, for example, the phase center or effective location for the virtual source is behind the array, thus creating a divergent transmitted wavefront approximating a point source. In some embodiments, following a similar operation to a virtual transmitter behind the array, a virtual receiver may be formed by digitally beamforming echoes as if to arrive at a point behind the array. In some embodiments, for example, the phase center or effective location for the virtual source is in front of the array, thus creating an acoustic source that diverges beyond said phase center or point of origination, also approximating a point source. In some embodiments, following similar operation to a virtual transmitter in front of the array, a virtual receiver may be formed by digitally beamforming echoes as if to arrive at a point in front of the array.

In some embodiments of the system 150, for example, a virtual receiver comprised of a plurality of elements can be beamformed in the analog domain using a microbeamformer, so as to generate one or more beamformed signals from the virtual receiver, e.g., thus removing the complexity of having additional receiver channels to accommodate each virtual receiver. For example, given a virtual receiver comprised of 64 elements and a bank of eight 8-to-1 microbeamformers focusing at the same virtual receiver point, the resulting eight microbeamformed signals require only eight receiver channels (e.g., comprised of analog filters, ADCs, etc.) instead of 64 channels. The resulting microbeamformed signals can be processed by the object beamformer in the same way that echoes from physical receivers are processed.

In some embodiments of the system 150, for example, the array elements may each include a collection of elements that operate as focused transmitters, such that focused beams are transmitted at one or more focal points in space that may or may not correspond to points on the object, but insonify a limited region of the object due to focusing. Focused transmission is useful to limit interference from unwanted objects or obstructions and to increase transmitted energy, e.g., thus improving the signal-to-noise ratio of received echoes. As in the virtual transmitter case, the delays on each element for the focused transmitter must be independently controllable to arbitrarily focus beams in space. Also, as in the case of the virtual receiver, the received echoes may be beamformed to further localize echoes from one or more directions, with receive focal points that may or may not correspond to points on the object.

In some implementations, for example, the transmitter-receiver unit 152 may also include analog and/or digital filters, for example, each ADC may integrate a bandpass or low pass analog anti-aliasing filter prior to conversion. Each ADC may also integrate a digital filter for the output, or the transmitter-receiver unit 152 may incorporate such a digital filter.

In some implementations, for example, the transmitter-receiver unit 152 may down-convert or demodulate the signals in the analog domain prior to digital conversion. For example, in the case of analog demodulation at the center frequency of a received waveform, two ADC channels may simultaneously sample the in-phase and quadrature (IQ) signals, or one ADC channel may perform interleaved sampling of the IQ signals, for example, an in-phase sample followed by a quadrature sample followed by an in-phase sample, etc. The delay between the in-phase and quadrature samples may be compensated, for example, using a digital interpolator or a fixed-delay all pass filter. Analog demodulation is useful for reducing the sampling rate of wideband echoes, e.g., thus reducing the number of samples that require storage and the amount of data transferred to the beamformer.

In some implementations, for example, digital IQ demodulation may be used instead of analog IQ demodulation to achieve a similar result, but with the additional advantage of being able to tune the demodulation frequency and bandwidth. Tuning demodulation frequency and bandwidth is useful for compensating frequency and depth dependent attenuation, which effectively reduces center frequency and bandwidth as a function of echo depth.

In some implementations, instead of IQ demodulation, for example, a more accurate technique for coherent IQ processing of wideband signals includes application of a Hilbert transform to the signals after conversion to the digital domain in order to obtain the analytic signal, as follows:

$$s_a(t)=s(t)+j\hat{s}(t),$$

where $s_a(t)$ is the analytic signal, s(t) is the input signal or in-phase component, and $\hat{s}(t)$ is the Hilbert transformed signal or quadrature component, which is obtained as follows:

$$\hat{s}(t) = \frac{1}{\pi t} * s(t),$$

where * is the convolution operator. The Hilbert transform may be computed using the fast Fourier transform (FFT), where a −90 degree phase shift is added to all positive frequency components and a +90 degree phase shift is added to all negative frequency components as follows:

$$\mathcal{F}(\mathcal{H}(s(t)))=-j\,\mathrm{sgn}(\omega)S(\omega),$$

where $\mathcal{F}$ is the Fourier transform operator, $\mathcal{H}$ is the Hilbert transform operator, sgn(x) is the sign function of x, ω is the angular frequency, and S(ω) is the Fourier transform of s(t). As the Hilbert transform is a multiplier operator in the frequency domain, it is also possible to approximate it using a finite impulse response (FIR) filter. The Hilbert transform technique for IQ processing is beneficial because it is immune to frequency and depth dependent attenuation of the received echoes. It is also possible to obtain an approximation to the analytic signal through quadrature sampling methods.

In some implementations, for example, the resulting digital echo signals, e.g., in either IQ form or real-only form, are transferred to the object beamformer unit 154, where they are stored within random-access memory (RAM) for beamforming. In some implementations, for example, the object beamformer unit 154 may be configurable to beamform virtual receivers in addition to object beamforming.

The model of the object is initially loaded into the data processing unit 156 by various means, e.g., reading a file in a storage system, or transferred from a computer aided design (CAD) software, or generated from a mathematical model using a computer program, or generated from an external means of imaging the object and converting the image to a model. For example, the model of the object can be comprised of simple convex polygons such as triangles, quadrilaterals, hexahedrals, etc. with complex reflectivities. For example, the model of the object can be comprised of a Delaunay triangulated model, which includes a list of vertices and a list of faces, where each face includes three indices into the list of vertices. The largest dimension of the largest element within the model should be one-wavelength or less, but preferably one-half wavelength or less, where the wavelength corresponds to the sound speed of the medium surrounding the object divided by the center frequency of transmission. It is also preferable that the faces of the polygons lie on a circle or circumcircle such that the diameters of all the circumcircles for all faces are equal or approximately equal across all faces, and such that the largest circumcircle diameter is one wavelength, but preferably one-half wavelength or less. Triangulated and quadrilateral models are preferable due to highly efficient ray-tracing algorithms that exist for these geometries. In some implementations, for example, the face center positions are computed and stored with the model, which positions are typically found by computing the mean coordinates across all vertices of the face, but other methods for center position calculation are possible. Additionally, the unit surface normal vectors for each face are also computed and stored with the model. Additionally, vertex normals for each vertex may be computed and stored with the model. Other quantities that may be computed and stored with the model, for example, can include Plucker coordinates, which are useful for efficient ray-tracing, and complex surface reflectivities for low contrast objects.

In some embodiments, the data processing unit 156 may be resident on one or more computers, e.g., a desktop computer, a laptop computer, a network of computer devices in data communication with each other via the Internet (e.g., in the 'cloud'), or other computing device including, but not limited to, a smartphone, a tablet, or a wearable computing/communications device. In some embodiments, the data processing unit may be resident in a device structure (e.g., housing) that also includes the transmitter-receiver unit 152 and/or the object beamformer unit 154. The transmitter-receiver unit 152 can be in communication with a data processing unit via a digital interface, e.g., which may be any interface or collection of interfaces including but not limited to USB, FireWire, Ethernet, PCI, IEEE 1394 Serial, Wi-Fi, Fiber Channel, fiber optics, a wireless bus, a serial bus, or a parallel bus.

In some embodiments, the data processing unit 156 may include a programmable processing unit and storage device that may include, but is not limited to, the following components, e.g., one or more processors, serial processors, parallel processors, math co-processors, general purpose graphical processing units (GPUs), FPGAs, ASICs, DSPs, nonvolatile memory, RAM, digital buffers, storage devices, hard drives, USB, FireWire, Ethernet, PCI, IEEE 1394 Serial, Wi-Fi, Fiber Channel, fiber optics, a wireless bus, a serial bus, an external display adaptor, an external display driver, a parallel bus, communications components, and power supply electronics.

In some embodiments, for example, the system 150 may also include the UI and display device 158, which can include, for example, a monitor, speaker, or other device to produce a combination of visual, audio or haptic output. For example, in some embodiments, the UI and display device 158 may be incorporated together with the data processing unit when the data processing unit is resident on a computer, e.g., such as in a single unit or separately through cabling to an external display.

In various embodiments, the data processing and control unit 156 includes one or more processors to process data and one or more memories in communication with the processor to store data. For example, the processor can include a central processing unit (CPU) or a microcontroller unit (MCU). For example, the memory can include processor-executable code, which when executed by the processor, configures the data processing and control unit 156 to perform various operations, such as receiving information, commands, and/or data, processing information and data, and transmitting or providing information/data to another entity (e.g., an external device). To support various functions of the data processing and control unit 156, the memory can store other information and data, such as instructions, software, values, images, and other data processed or referenced by the processor. Various types of random-access memory (RAM) devices, read only memory (ROM) devices, flash memory devices, and other suitable storage media can be used to implement storage functions of the memory. The memory can store data and information of the data processing and control unit 156 and other units of the system. For example, the memory can store system unit parameters, and hardware constraints, as well as software parameters and programs for operation on the system. In this example, the data processing and control unit 156 includes an input/output (I/O) unit that can allow communicative connectability of the data processing and control unit 156 to other units of the system. For example, the I/O unit can provide the data processing and control unit 156 to be in communications with other devices or systems, e.g., using various types of wired or wireless interfaces compatible with typical data communication standards, for example, including, but not limited to, Universal Serial Bus (USB), IEEE 1394 (FireWire), Bluetooth, IEEE 802.111, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE/5G cellular communication methods, and parallel interfaces. The I/O unit can also provide communicative connectability of the data processing and control unit 156 to an external interface (e.g., the external device), source of data storage, or display device (e.g., the UI and display device 158). The I/O unit of the data processing and control unit 156 can also interface with other external interfaces, sources of data storage, and/or visual or audio display devices, etc., to retrieve and transfer data and information that can be processed by the processor, stored in the memory, or exhibited on an output unit of the system 150 (e.g., UI and display device 158).

The object beamformer unit 154 includes software that contains code and/or coordinate lists and/or vector information representing a predetermined model of the object and/or code for generating a new model of the object or modifying a new or existing model of the object based on new information about the object provided to the object beamformer unit 154 by the data processing and control unit 156. In some embodiments, the object beamformer unit 154 is a data processing module of the data processing and control unit 156, where the object beamformer unit 154 utilizes the hardware of the data processing and control unit 156, e.g., including but not limited to the one or more processors and one or more memories of the data processing and control unit 156. Yet, in some embodiments, the object beamformer unit 154 includes one or more processors coupled to one or more memory units separate from that of the data processing and control unit 156.

In some implementations, for example, prior to beamformation, the model of the object is loaded into an addressable RAM unit within the object beamformer unit 154 from the data processing and control unit 156. Also prior to beamformation, the transducer array element positions and normal vectors are loaded into the object beamformer unit 154 from the data processing and control unit 156. The positions of the transducer array elements and array normal vectors are stored in the data processing and control unit 156 as a model in its own frame of reference, as depicted under the array model 153 in the example of FIG. 1E. The positions of the transducer array elements and array normal vectors communicated to the object beamformer unit 154 from the data processing and control unit 156 are varied by applying a transformation, comprised of a rotation component and a translation component. The translation component is expressed as Cartesian coordinates in three dimensions, i.e., x, y, and z. The rotation component is determined by consecutive rotations by angles about the x-axis, y-axis, and z-axis, in various consecutive orders, e.g., xyz, yzx, zxy, xzy, zyx, yxz, otherwise known as Tait-Bryan angles.

An example 3×3 rotation matrix is computed as follows:

$$R = R_z(\alpha)R_y(\beta)R_x(\gamma) =$$

$$\begin{bmatrix} \overset{yaw}{\cos\alpha} & -\sin\alpha & 0 \\ \sin\alpha & \cos\alpha & 0 \\ 0 & 0 & 1 \end{bmatrix} \begin{bmatrix} \overset{pitch}{\cos\beta} & 0 & \sin\beta \\ 0 & 1 & 0 \\ -\sin\beta & 0 & \cos\beta \end{bmatrix} \begin{bmatrix} \overset{roll}{1} & 0 & 0 \\ 0 & \cos\gamma & -\sin\gamma \\ 0 & \sin\gamma & \cos\gamma \end{bmatrix}$$

where, R, represents a rotation whose yaw, pitch, and roll angles are $\alpha$, $\beta$ and $\gamma$, respectively. More formally, it is an intrinsic rotation whose Tait-Bryan angles are $\alpha$, $\beta$, $\gamma$, about axes z, y, x, respectively. Other methods for computing the 3×3 rotation matrix component include Euler angles, axis-angle representation, Rodrigues' rotation formula, and quaternions. The rotation and translation are applied to the array model coordinates as follows:

$$A_c' = RA_c + h$$

where $A_c'$ is the transformed set of coordinates, R is the 3×3 rotation matrix, $A_c$ is the input set of array coordinates, and h is the 3×1 translation vector. The normal vectors of the array elements, $A_n$, are also transformed as follows:

$$A_n' = RA_n$$

where $A_n'$ is the set of transformed array normals. The transformed coordinates and normals are communicated to the beamformer unit for weight and delay calculations. The rotation and translation may also be formulated as a mathematically equivalent 4×4 rigid homogeneous transformation, T, as follows:

$$T = \begin{bmatrix} r_{11} & r_{12} & r_{13} & h_1 \\ r_{21} & r_{22} & r_{23} & h_2 \\ r_{31} & r_{32} & r_{33} & h_3 \\ 0 & 0 & 0 & 1 \end{bmatrix}$$

where $h_1$ is the x translation, $h_2$ is the y translation, and $h_3$ is the z translation, and $$R = \begin{bmatrix} r_{11} & r_{12} & r_{13} \\ r_{21} & r_{22} & r_{23} \\ r_{31} & r_{32} & r_{33} \end{bmatrix} \text{ and } h = \begin{bmatrix} h_1 \\ h_2 \\ h_3 \end{bmatrix}.$$

T is an efficient way of performing translation and rotation transformations on sets of coordinates, for example, arranged as a 4×N matrix, P, with the $4^{th}$ row of P containing all ones, as follows:

$$P' = TP,$$

where P' is the transformed set of coordinates. Translation is omitted simply by setting the $4^{th}$ row of P to zeros. Such operations are understood in the fields of kinematics and computer graphics.

Figure 2:
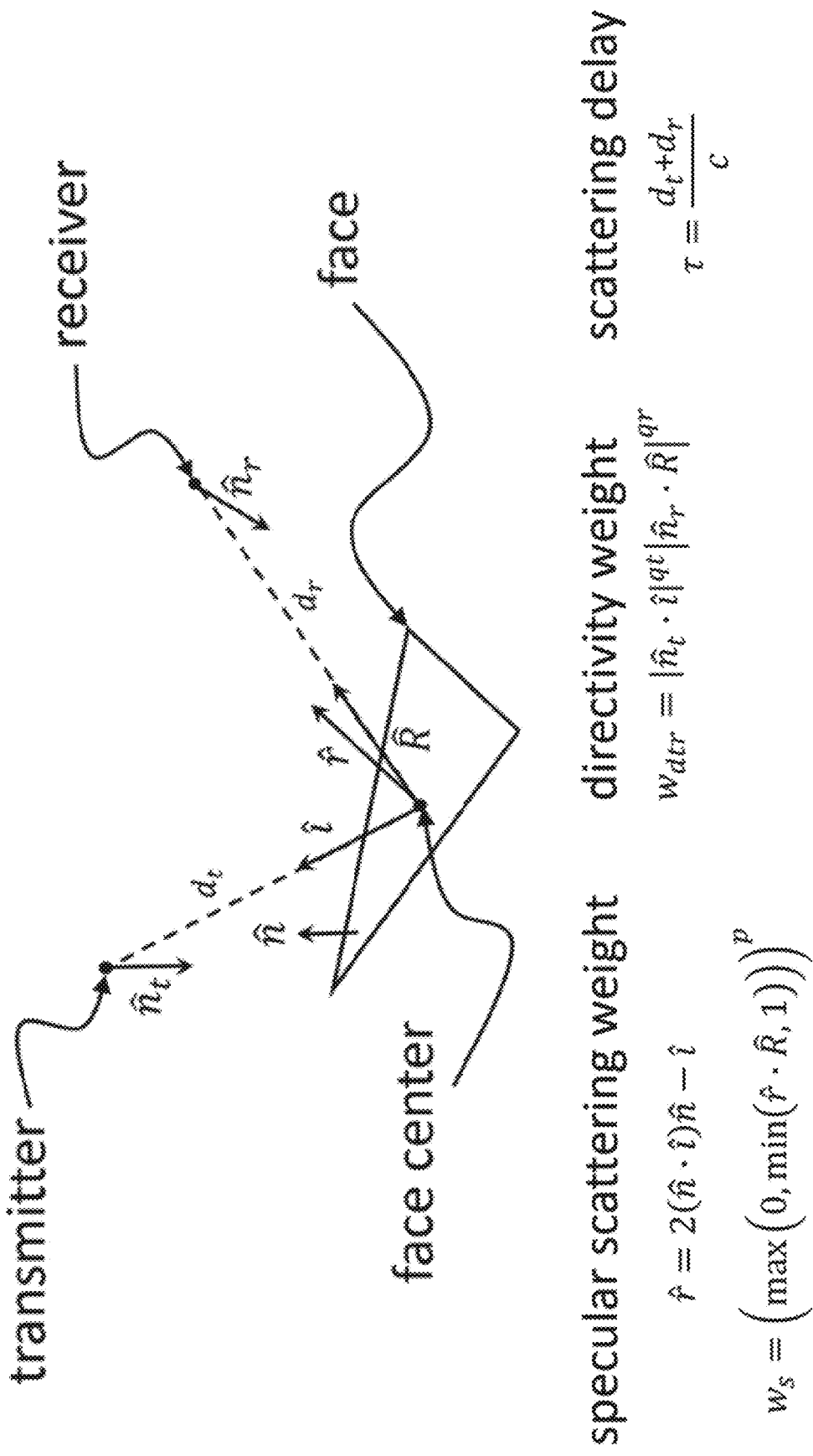
FIG. 2 shows a diagram of an example implementation of the method to beamform the object surface via the synthetic aperture transmitted and received ultrasound signals, in accordance with the present technology.

FIG. 2 shows a diagram illustrative of an example implementation of the object beamformer method to beamform the object surface via the synthetic aperture transmitted and received ultrasound signals, in accordance with the present technology. In some example embodiments of the system 150, an algorithm for beamforming the object is executed within the object beamformer unit 154 and comprises a set of example mathematical operations of the object beamformer. The diagram of FIG. 2 also illustrates example equations for calculating particular parameters by the algorithm, implementable by the object beamformer unit, which can include a specular scattering weight parameter, a directivity weight parameter, and a scattering delay parameter (also shown below).

| specular scattering weight | directivity weight | scattering delay |
|---|---|---|
| $\hat{r} = 2(\hat{n} \cdot \hat{\iota})\hat{n} - \hat{\iota}$ | $w_{dir} = \|\hat{n}_t \cdot \hat{\iota}\|^{q_t} \|\hat{n}_r \cdot \hat{R}\|^{q_r}$ | $\tau = \dfrac{d_t + d_r}{c}$ |
| $w_s = (\max(0, \min(\hat{r} \cdot \hat{R}, 1)))^p$ | | |

In some implementations of the object beamformer, for each transmitter and receiver combination, the object beamformer is configured to compute several quantities that determine delays and weights that are applied to the echoes prior to summation. In the example of FIG. 2, the geometry of the object model stored within the object beamformer is illustrated for a single triangular face, with the understanding that an object may be comprised of a plurality of such triangular faces, and that each face may be treated in the manner as the face shown.

Likewise, in FIG. 2, the geometry of a single transmitter and a single receiver location is also shown, with the understanding that the same geometrical construction is applicable to multiple pairs of transmitters and/or receivers comprising a transducer array, and is not limited to transmitters and receivers that occupy different physical or virtual positions. It is also with the understanding that the depiction of a single transmitter or single receiver may be comprised of one or more transducer elements that are beamformed to produce a single echo as if derived from a single transmitter or receiver placed at the position and orientation shown.

Notably, the geometry of the transmitters and receivers used within object beamformer is based on a transformation applied to a model of the transducer array, where the transformation is controllable and manipulates the model in the frame of reference of the object model. Contrastingly, an equivalent transformation could be applied to the object model, and the object model could be manipulated in space in the frame of reference of the array model; however, the computational demands on present-day computing devices of applying a transformation to the object model as opposed to the array model are typically much more significant and may preclude real-time operation. With the understanding that both ways are equivalent, the former method is assumed. The transformed coordinates are computed within the object beamformer unit 154 or the data processing unit 156 according to a transformation determined by the data processing unit 156.

As illustrated in FIG. 2, for each transmitter position, the object beamformer is configured to compute the distance from a transmitter position to a position on one or more faces on the model ($d_t$). Likewise, for each receiver position, the object beamformer is configured to compute the distance from a receiver position to a position on one or more faces on the model ($d_r$). Herein, a transmitter position is the known position of a transmitting transducer element or elements and/or the known position of an acoustic signal transmitted by transducer element(s) known by an acoustic transmission parameter, such as a phase center location; similarly, a receiver position is the known position of a receiving transducer element or elements and/or the known position of an acoustic echo received by transducer element(s) known by an acoustic parameter. The face position for the distance calculations may be the face center position or it may be a different position as determined, for example, through ray-tracing from the transmitter or receiver to an intersection point on the polygon. The face position may also be determined, for example, from a combination of neighboring vertices, face normal vectors, and vertex normal vectors in order to solve for an interpolated face position based on local curvature of the model.

For the purpose of this example, a global average sound speed of the medium surrounding the object, denoted with the variable, c, is assumed. Thus, the delay, $\tau$, from the transmitter to a point on the model to a receiver is computed by dividing the round-trip path, $d_t + d_r$, by the medium speed according to the equation:

$$\tau = \frac{d_t + d_r}{c}.$$

In addition to delays, for each transmitter position, the beamformer unit is configured to compute the incident unit vector, $\hat{i}$, for one or more faces on the model. Likewise, the beamformer unit can be configured to compute the specular reflection unit vector, $\hat{r}$, according to the equation:

$$\hat{r} = 2(\hat{n} \cdot \hat{i})\hat{n} - \hat{i}$$

where $\hat{n}$ is the unit normal vector of the face, $\hat{i}$ is the vector of incidence from the position of the transmitter, and the quantity $\hat{n} \cdot \hat{i}$ is the dot product, i.e., cosine of the angle, between the unit vectors $\hat{n}$ and $\hat{i}$.

Likewise, for each receiver position, the beamformer unit is configured to compute the receiver unit vector, $\hat{R}$, for one or more faces on the model. For each combination of transmitter position, face position, and receiver position, the beamformer unit is configured to compute a specular scattering weight, $w_s$, according to the following equation:

$$w_s = (\max(0, \min(\hat{r} \cdot \hat{R}, 1)))^p,$$

where $\hat{r} \cdot \hat{R}$ is the dot product, i.e., cosine of the angle, between the unit vectors $\hat{r}$ and $\hat{R}$, and p is a power term, also referred to as the specular exponent, that typically has a value of at least 1, but may be increased to narrow the specular scattering angle, for example, to match reflected intensity observed experimentally.

In this example, the beamformer unit is configured to clamp $w_s$ to the range of 0 to 1 such that negative values are given a value of 0, i.e., the specular reflection is not possible. If $\hat{r}$ and $\hat{R}$ are parallel, then $w_s = 1$. If $\hat{r}$ and $\hat{R}$ are perpendicular, then $w_s = 0$. If $\hat{r}$ and $\hat{R}$ are anti-parallel, then $w_s = 0$. This basic weighting term is solely responsible for weighting the specular scattering contribution of a scattering element on the model.

Other contributions to the echo weighting may include a transmit element directivity weighting, $w_{dt}$, which may be approximated as the absolute value of the dot product between the transmitter unit normal vector, $\hat{n}_t$, and the inverse of the unit incident unit vector, $\hat{i}$, as follows:

$$w_{dt} = |\hat{n}_t \cdot \hat{i}|^{qt},$$

where qt is a power term similar to p above, with a value of typically 1 depending on the directivity of a given element. In the above definition, the transmit directivity is mathematically equivalent to the cosine of the angle between the transmitter normal vector and it incident vector, which in agreement with the $\cos(\theta)$ obliquity factor in the first Rayleigh-Sommerfeld solution for plane wave sources.

Similarly, the echo weighting may also include a receiver element directivity weighting, $w_{dr}$, which may be approximated as the absolute value of the dot product between the receiver unit normal vector, $\hat{n}_r$, and the inverse of the unit receive vector, $\hat{R}$, as follows:

$$w_{dr} = |\hat{n}_r \cdot \hat{R}|^{qr},$$

where qr is a power term similar to p above, with a value of typically 1 depending on the directivity of a given element. In the above definition, the receiver directivity is mathematically equivalent to the cosine of the angle between the receiver normal vector and the receive vector, which in agreement with the $\cos(\theta)$ obliquity factor in the first Rayleigh-Sommerfeld solution for plane wave sources.

The overall directivity for a given transmitter and receiver pair, $w_{dtr}$, is given by the product of the individual transmitter and receiver directivities as follows:

$$w_{dtr} = w_{dt} w_{dr},$$

where the separation of the directivity allows for differing spatial responses between transmit and receive. It is noted, for example, that the meaning of $w_{dtr}$ becomes clearer when limiting cases are considered, e.g., when $\hat{n}_t$ and $\hat{i}$ are perpendicular, $w_{dt}=0$, or if $\hat{n}_r$ and $\hat{R}$ are perpendicular, $w_{dr}=0$, either of which result in $w_{dtr}=0$. Likewise, when $\hat{n}_t$ and $\hat{i}$ are parallel, $w_{dt}=1$, and if $\hat{n}_r$ and $\hat{R}$ are parallel, $w_{dr}=1$.

More exact expressions for element directivities $w_{dt}$ and $w_{dr}$ based on analytical formulas and/or measured directivity patterns of the transmit and receive elements are also possible, for example, using polynomial fits to field magnitude measurements as a function of angle from the normal of the element.

In some embodiments, for example, other weighting factors may be included as well, e.g., to account for the area of a given face. If all faces have approximately the same area as a consequence of how uniformly the object model is meshed in terms of polygon edge lengths, polygon areas, or circumcircle diameters, then the contributions from some faces are negligibly higher or lower than others, and an area weighting term can be omitted.

Examples of the other weighting factors that may be included can include a complex reflectivity term, $w_r$, which lumps together real and complex scattering behavior that may be dependent on frequency and angle of incidence, but may also be dependent on physical parameters of the object including, but not limited to, sound speed, density, acoustic impedance, compressibility, attenuation, surface texture, inhomogeneities at or beneath the surface, and multiple layers. The complex reflectivity term may take the form:

$$w_r = \alpha + j\beta,$$

where $\alpha$ is the real component of reflectivity, $\beta$ is the complex component of reflectivity, and $j$ is the unit imaginary number. It is understood that $\alpha$ and $\beta$ may both have a complex dependence on other quantities, e.g., frequency, angle of incidence, etc. Here $w_r$ may include effects of diffuse scattering, analogous to Lambert's cosine law in optics.

Examples of the other weighting factors that may be included can include a compensation weight, $w_c$, which compensates for frequency-dependent and distance-dependent attenuation and $1/r$ amplitude spreading loss (assuming a point source). For example, $w_c$ is assigned a high value for the longest propagation path and the lowest value for the shortest propagation path. In this way, the compensated echoes corresponding to the longest propagation paths have similar amplitude compared to echoes from the shortest propagation paths.

The overall complex weight, $w$, for a given transmitter, receiver, and model face is then found as follows:

$$w = w_s w_{dtr} w_r w_c.$$

In some implementations of the object beamformer, the object beamformer is configured to compute the summation of echo samples corresponding to a plurality of transmitter positions, receiver positions, and model points according to the following equation:

$$f(t, M_A, T, M_O) = \sum_{i=1}^{NTX} \sum_{j=1}^{NRX} \sum_{k=1}^{NMP} w_{ijk}(M_A, T, M_O) s_{ij}(t - \tau_{ijk}(M_A, T, M_O)),$$

where $f(t, M_A, T, M_O)$ is the beamformed signal, t is time, $M_A$ is the array model comprised of various parameters including the coordinates of $N_{TX}$ active transmitters and the coordinates of $N_{RX}$ active receivers, T is the homogeneous transformation matrix applied to the active transmitter and receiver positions, which is a function of three translation distances and three rotation angles comprising six degrees of freedom, $M_O$ is the object model comprised of various parameters including $N_{MP}$ model point positions, i is the active transmitter index, j is the active receiver index, k is the model point index, $w_{ijk}(M_A, T, M_O)$ are the overall complex beamformer weights, $s_{ij}(t)$ are the stored synthetic aperture echo signals, and $\tau_{ijk}(M_A, T, M_O)$ are the computed beamformer delays.

In the example object beamformer implementation above, the object beamformer could be mathematically compared, albeit different, to a delay-and-sum beamformer used in conventional synthetic aperture ultrasound image formation, e.g., such as synthetic aperture point beamforming. For example, a more conventional generalized synthetic aperture point beamformer may take the following mathematical form:

$$f_{conv}(t, M_A, IP) = \sum_{i=1}^{NTX} \sum_{j=1}^{NRX} w_{ij}(M_A, IP) s_{ij}(t - \tau_{ij}(M_A, IP)),$$

where t is time, IP represents one or more image points, $M_A$ is a model of the array, $w_{ij}(M_A, IP)$ is a 2D array of weights that may or may not be a function of the image point and array model, and $\tau_{ij}(M_A, IP)$ is the roundtrip delay to and from a given image point from the array. In a conventional beamformer, the weights may be fixed for a given array; for example, an apodization function, e.g., $w_{ij}(M_A)$, is a 2D array of weights chosen to be the same value for all beamformed points in space (e.g., $w_{ij}(M_A)$ is constant for a given array model), or the weights may be a variable 2D array of weights, for example, a function of a given point in space relative to the array model, e.g., a dynamic apodization function, e.g., $w_{ij}(M_A, IP)$. Many possible apodization functions are possible. In contrast with conventional delay-and-sum beamformers used in conventional imaging, it is shown that the disclosed object beamformer technology is primarily differentiated from a conventional point beamformer by (i) how the weights are computed as a function of the array model, object model, and their relative orientation, e.g., $w_{ijk}(M_A, T, M_O)$, and (ii) how the echoes are summed over the object model, e.g., a third summation over $N_{MP}$ model points. For example, both $f(t, M_A, T, M_O)$, $f_{conv}(t, M_A, IP)$, and other similar mathematical formulations, can be viewed as a beamformer. Although the disclosed object beamformer is not strictly a point beamformer, it is possible, for example in some implementations, to redefine the object beamformer as a point beamformer by setting $N_{MP}=1$ (i.e., remove third summation), setting $M_O = IP$, redefining $w_{ijk}(M_A, T, M_O)$ to $w_{ij}(M_A, IP)$, and redefining $\tau_{ijk}(M_A, T, M_O)$ to $\tau_{ij}(M_A, IP)$.

In some implementations of the object beamformer, the object beamformer is configured to determine the overall complex beamformer weights and/or other variables and parameters of the beamformed signal based on a look-up table.

In some implementations, the array of transducer elements includes N transducer elements, at least some of which are used for both transmission and reception (i.e., $N_{TX} = N_{RX}$, and $i=j$ refers to the same element) in full synthetic transmit aperture operation. Due to the property of acoustic reciprocity between a source and receiver pair, it is only necessary to compute weights and delays once for each reciprocal bistatic transmitter and receiver pair, i.e., pairs satisfying $(i,j)$ and $(j,i)$ such that $i \neq j$, e.g., $(i,j)=(1,2)$ and $(i,j)=(2,1)$. Mathematically, the object beamformer may be modified as follows:

$$f(t, M_A, T, M_O) = \sum_{i=1}^{N_{TX}} \sum_{j=i}^{N_{RX}} \sum_{k=1}^{N_{MP}} a_{ij} w_{ijk}(M_A, T, M_O) s_{ij}(t - \tau_{ijk}(M_A, T, M_O)),$$

where $a_{ij}=2$ for $i \neq j$ and $a_{ij}=1$ for $i=j$. Equivalently, according to the principle of reciprocity, the object beamformer may also be modified as follows:

$$f(t, M_A, T, M_O) = \sum_{j=1}^{N_{RX}} \sum_{i=j}^{N_{TX}} \sum_{k=1}^{N_{MP}} a_{ij} w_{ijk}(M_A, T, M_O) s_{ij}(t - \tau_{ijk}(M_A, T, M_O)),$$

where $a_{ij}=2$ for $i \neq j$ and $a_{ij}=1$ for $i=j$. The benefit of such implementations is a reduction in operations by roughly a factor of 2 from $N^2$ to $$\frac{N^2 + N}{2}.$$

In some implementations, for example, the monostatic or a subset of monostatic echoes (e.g., at least some of $i=j$ above) and/or the bistatic or a subset of bistatic echoes (e.g., at least some of $i \neq j$ above) may be summed in the object beamformer.

In some implementations, for example, the object beamformer output can be multiplied by a time domain window function. For example, $$f_{tdw}(t, M_A, T, M_O) = wf(t) f(t, M_A, T, M_O),$$

where wf(t) is a time domain window function, for example the Hann window, given by the following function:

$$wf(t) = \begin{cases} \cos^2\left(\frac{2\pi}{L} t\right), & |t| \leq \frac{L}{2}, \\ 0, & |t| > L/2 \end{cases}$$

where L is the window length in the time domain. Time domain windowing functions can be used to suppress undesirable echo components away from t=0. Other window functions may be used as well, including but not limited to: Hamming, Blackman, Nuttall, Gaussian, Tukey, Kaiser, Parzen, Welch, Slepian, ultraspherical, exponential, flat top, triangular, sine, and rectangular.

The transmitted waveforms may be spatially encoded, temporally encoded, or spatially and temporally encoded. It is assumed that the echoes, $s_{ij}(t)$, are decoded prior to beamforming. Here it is implicitly assumed that the time variable, t, is sampled, e.g., t=n dt, where n is an integer, dt=1/$f_s$, and $f_s$ is the sampling rate of the stored echo samples. In the event that the quantity, $\tau_{ijk}(M_A, T, M_O)$ does not fall on an integer multiple of dt, the beamformer unit can be configured to interpolate fractional delay values from neighboring samples using any number of methods of efficient interpolation algorithms and wideband beamformers. The summation shown above is just one embodiment that includes a weighted delay-and-sum beamformer. The function, $f(t, M_A, T, M_O)$, may be obtained through other combinations of linear and nonlinear operations, such that incoherent echo energy is suppressed.

The output of the beamformer unit is transferred to the data processing unit, where it is used in the objective function of an optimization process, in which an optimizer varies each of six degrees-of-freedom determining the transformation, T, in order to minimize the objective function. One example of an objective function, g(t), is given below:

$$g(M_A, T, M_O) = \int_{t_1}^{t_2} |f(t, M_A, M_O)|^2 dt,$$

where $t_1$ is the starting time and $t_2$ is the ending time. Another example of an objective function, g(t), that incorporates the time window described above, is given below:

$$g(M_A, T, M_O) = \int_{t_1}^{t_2} |wf(t) f(t, M_A, T, M_O)|^2 dt.$$

The goal of the optimizer is to maximize $g(M_A, T, M_O)$ as follows:

$$M_A^{opt}, T^{opt}, M_O^{opt} = \arg\max_{M_A, T, M_O} g(M_A, T, M_O),$$

where the integrated power of the beamformer output over a time window ranging from $t_1$ to $t_2$ is maximized by varying each of six degrees-of-freedom corresponding to T and a set of object model variables $M_A$ to find an optimal transformer, $T^{opt}$, and a set of optimal object model variables, $M_O^{opt}$. The time window duration, $\Delta t = t_2 - t_1$, is inversely dependent on the center frequency and bandwidth of the received echoes. For example, for waveform transmissions modeled with a Gaussian amplitude modulated sinusoidal pulse, p(t), as follows:

$$p(t) = e^{-\frac{t^2}{2t_v}} \sin(2\pi f_c t)$$

$$t_v = \frac{3 \ln 10}{5} \frac{1}{\pi^2} \frac{1}{bw^2 f_c^2}$$

where bw is the −6 dB two-way fractional bandwidth ratio, i.e., bandwidth divided by center frequency for a symmetrical spectrum, and $f_c$ is the center frequency, the −6 dB magnitude cutoff time is given by:

$$t_c^{-6 \, dB} = \sqrt{\frac{6 \ln 2 \ln 10}{5}} \frac{1}{\pi \, bw \, f_c}.$$

Here, $\Delta t = t_2 - t_1 = t_c^{-6 \, dB} - (-t_c^{-6 \, dB}) = 2 t_c^{-6 \, dB}$, which is inversely proportional to center frequency and fractional bandwidth. It is understood that other magnitude cutoffs and cutoff times may be used in order to increase or limit the window over which beamformed echo power is integrated, but the analytical formulas above give guidance as to how the window duration and limits of integration must change as a function of frequency and bandwidth.

Further example implementations were conducted, as described. A numerical simulation of the operation of the object beamformer was performed to demonstrate its ability to localize on a simple object including 25 scattering positions using a sparse synthetic aperture comprising 5 elements. The geometrical arrangement of the scatterers and the array element positions is shown in FIG. 3.

Figure 3:
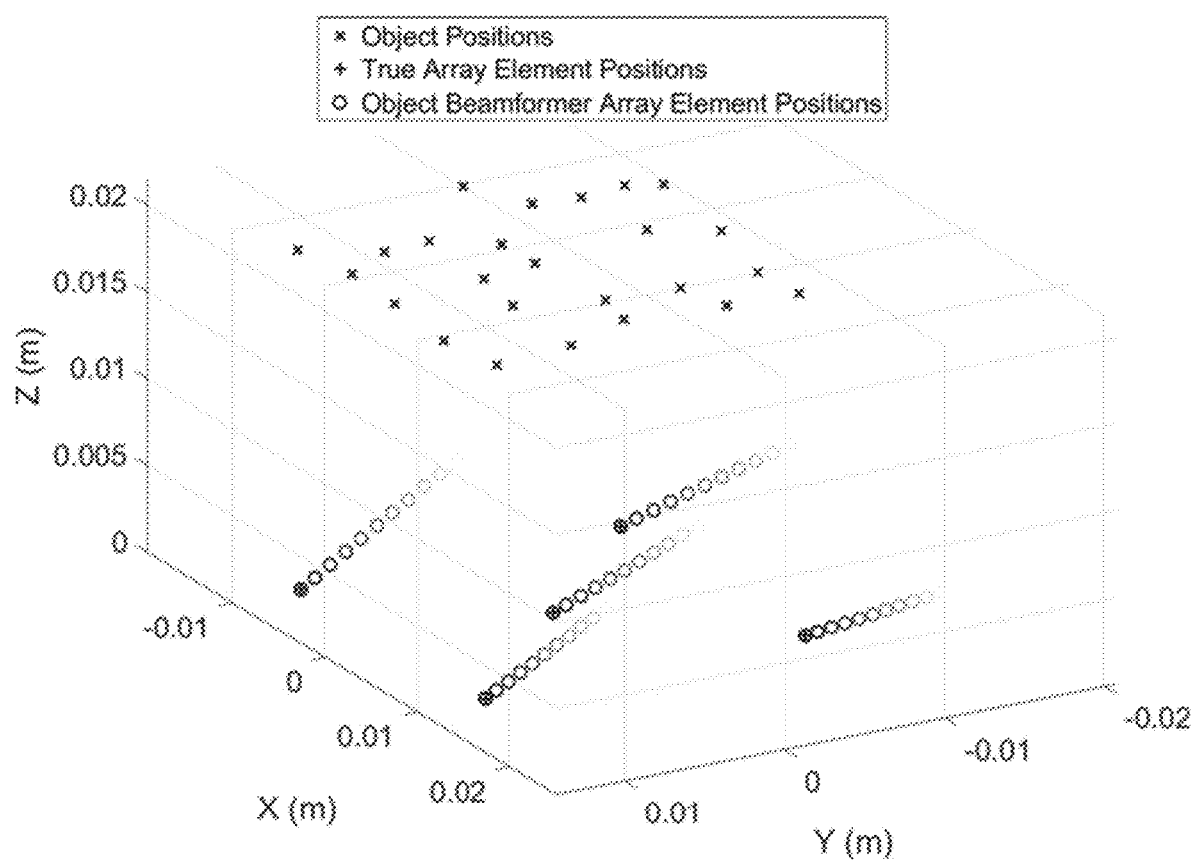
FIG. 3 shows a plot depicting the geometry used in an example implementation using numerical simulation of an example object beamformer technique in accordance with the present technology.

FIG. 3 shows a plot depicting the geometry used in an example implementation using numerical simulation of an example object beamformer technique comprised of object scatterer positions modeled as point targets (marked with 'x' symbols) and array element positions modeled as point sources and receivers. The array element positions used within the object beamformer, marked with 'o' symbols, are transformed versions of the true array element positions marked with '+' symbols. The transformed coordinates are obtained by rotating the true array element positions about the vector [1 1 1] by angles ranging from 0 to 10 degrees followed by translation of the rotated coordinate in the direction of vector [1 −1 1] by magnitudes ranging from 0 to 10 millimeters. Increasing distance from the true positions are encoded in grayscale.

For the purposes of demonstrating the function of the object beamformer, for example, each array position can be a transmitter and a receiver, thus both monostatic and bistatic scattering is considered. The transmitters and receivers are assumed to be point sources and point receivers with $\cos(\theta)$ sensitivity, e.g., in accordance with the geometry of FIG. 2 and the definitions of $w_{dr}$ and $w_{dt}$ defined above with qt=1 and qr=1, the directional sensitivity on transmission is given by $|\hat{n}_t \cdot \hat{i}|$ and the directional sensitivity on reception is given by $\hat{n}_r \cdot \hat{R}|$. The geometry of the array is a 4 cm$^2$ square sparse aperture with one transmitter/receiver at each corner and one transmitter/receiver at the center. The scatterer positions are assumed to be point reflectors with $\cos(\theta)$ scattering amplitude of incident waves, e.g., in accordance with the geometry of FIG. 2 and the definition of $w_s$ defined above with p=1. The transmitted waveform generated from each source is modeled using a Gaussian modulated sinusoidal pressure waveform as defined above using a center frequency, $f_c$, of 1 MHz and a two-way −6 dB fractional bandwidth, bw, of 60%. The sound speed is set to 1500 m/s, resulting in a wavelength of 1.5 millimeters.

Echoes are numerically computed, for example, using the approximate Rayleigh integral formulation in the time domain for pressure sources given by the following equation:

$$p(x,t) \approx \frac{1}{c_0} \int \int_A \frac{1}{2\pi \|x-x'\|} \frac{\partial}{\partial t} p_s\left(x', t - \frac{\|x-x'\|}{c_0}\right) \cos(\varphi) dx'$$

where p(x,t) is the acoustic pressure waveform at vector position x in space and time t, $c_0$ is medium sound speed, $p_s$(x,t) is the surface pressure component of the source, A is an integrand of area, $\|x-x'\|$ is the Euclidean length of the vector x−x', and $\cos(\varphi)$ is the obliquity term given by the angle between the vector x−x' and the surface normal of the source (equivalent to $\cos(\theta)$ directivity shown above). Assuming reciprocity, a homogeneous medium, and the first-order Born approximation (i.e., no multiple scattering), the pulse-echo field, $p_{pe}$(x,t), may be approximated by the following:

$$p_{pe}(x,t) = p_t(x,t) *_t p_r(x,t),$$

where $p_t$(x,t) is the field at the scatterer, $p_r$(x,t) is the field at the receiver from a source at the scatterer, and the operator $*_t$ represents convolution in the time domain. For a collection of points sources, receivers, and point scatterers, the pulse-echo responses of the individual scatterers are added with corresponding weighting for each combination, e.g., based on directivity and scattered amplitude weighting. With knowledge of unit normal vectors of the transmitters and receivers, the directivity of the transmitter and receiver responses (e.g., $\cos(\theta)$ terms) are easily included for each combination of transmitter, receiver, and scatterer position as described above (e.g., $w_{dtr}$). Likewise, the directivity of scattered waves is easily included with knowledge of scatterer unit normal vectors as described above (e.g., $w_s$). Without loss of generality, for example frequency and depth dependent attenuation are neglected in the simulation.

To simulate the received synthetic aperture echoes, for example, the true array element positions are used, as shown in FIG. 3 each marked with a '+'. In accordance with synthetic transmit aperture imaging, each source is separately excited, and the echo for each receiver is simulated by superposition of all scattering events from all point scatterers, also shown in FIG. 3 each marked with an 'x'. In this way, each transmission event results in five received echoes corresponding to the five possible receivers, which is then repeated for all sources, yielding a full synthetic transmit aperture data set including 25 echoes for each possible combination of source and receiver.

Figure 4:
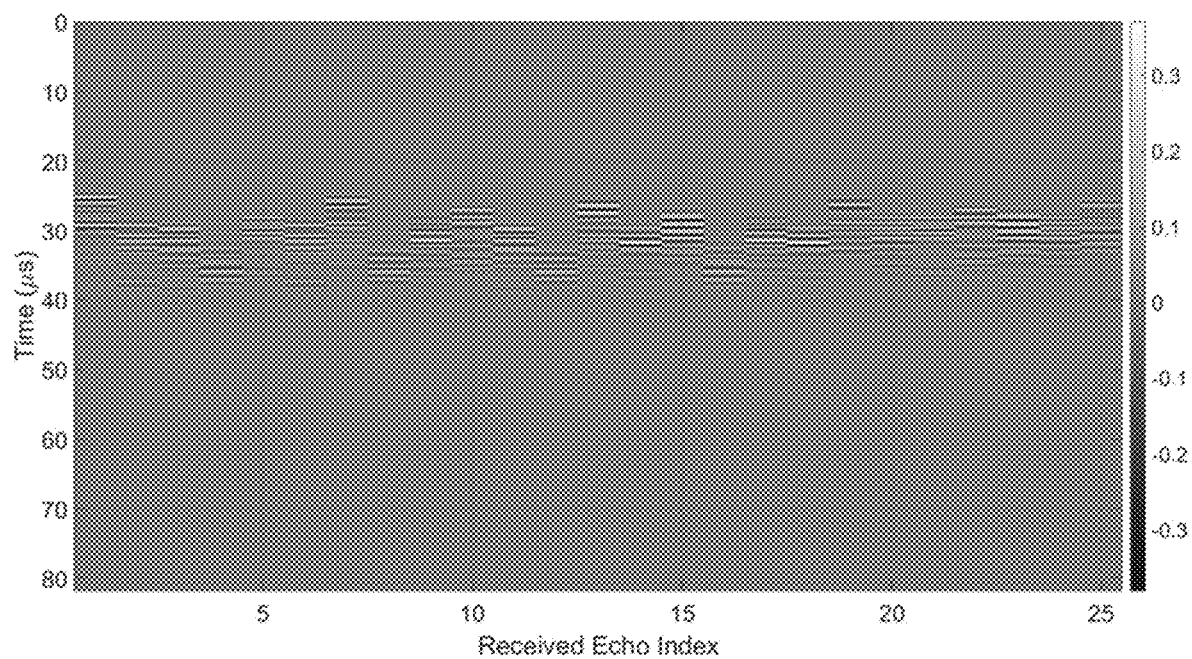
FIG. 4 shows a plot depicting simulated received echoes with time in microseconds on the vertical scale and echo index on the horizontal scale.

FIG. 4 shows a plot depicting simulated received echoes with time in microseconds on the vertical scale and echo index on the horizontal scale. The amplitude of the echoes is encoded in the shown grayscale ranging from −0.38 to 0.38. The amplitude units are in units of pressure for 1 Pascal peak pressure sources. The echoes in FIG. 4 are organized according to the full synthetic aperture data set corresponding to 25 echoes, with the echoes indexed 1-5 resulting from transmission on source index 1, echoes indexed 6-10 resulting from transmission on source index 2, and so on. This data set is equivalent to $s_{ij}$(t) in the equation above with echo indexing according to 5(i−1)+j, where i is the source index and j is the receiver index, and i and j are integers spanning the set 1, 2, 3, 4, and 5.

The object beamformer delays, $\tau_{ijk}(M_A,T,M_O)$, are computed according to the method above for varying degrees of rotation and translation of the true array element position coordinates relative to the object scatterer position coordinates (indexed k) in order to illustrate the sensitivity of the object beamformer to relative rotational and translational offsets between the array and the object. Here, the transformation, T, represents the homogenous transformation that includes a rotation followed by a translation, which is applied to the true array element position coordinates. In the simulation, the true array element position coordinates shown in FIG. 3 serve as the array model, but the array model could also be represented in an arbitrary frame of reference. Likewise, the object position coordinates shown in FIG. 3 also serve as the object model, but the object model could also be represented in an arbitrary frame of reference. Importantly, the number of object beamformer delays for this problem is 5×5×25=625, which is far more than 25, or the number of synthetic aperture delay terms for beamforming a point in space using the same aperture. In this way, as stated above, the synthetic aperture is formed with the object. It is also seen here that the incorporation of the object model into the beamformer massively increases the spatial diversity of the coherence condition required for coherent detection.

In the simulation, the homogeneous transformation, T, includes a rotation about the vector [1 1 1] by angles ranging from 0 to 10 degrees followed by translation in the direction of vector [1 −1 1] by translation magnitudes ranging from 0 to 10 millimeters. FIG. 3 depicts the range of array position coordinates used in the object beamformer, each marked with a 'o' and with grayscale shading from black to white to show increasing distance from the true array element position coordinates.

Given $s_{ij}$(t), $w_{ijk}$ ($M_A$,T,$M_O$) computed according to specular scattering element directivity as described above, and $\tau_{ijk}(M_A,T,M_O)$, the object beamformer summation is performed as a function of the transformation, T, in increments of 0.1 degrees of rotation and 0.1 mm of translation magnitude, i.e., both rotation and translation occur for each value of T.

Figure 5:
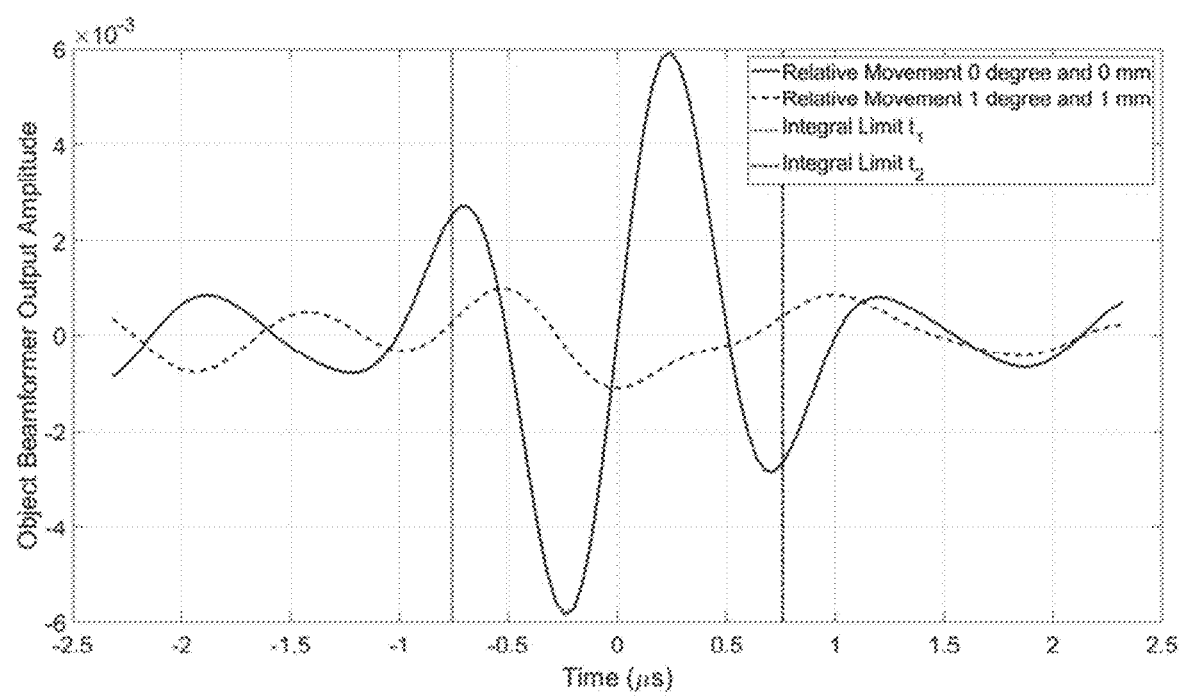
FIG. 5 shows a data plot depicting the output of an example object beamformer for rotation and translation in an example implementation.

FIG. 5 shows a data plot depicting the output of an example object beamformer, i.e., corresponding to the quantity $f(t,M_A,T,M_O)$ given above, for rotation and translation equal to 0 degree and 0 millimeter, respectively, of the true array element positions shown in FIG. 3, and for rotation and translation equal to 1 degree and 1 millimeter, respectively, of the true array element positions shown in FIG. 3. The amplitude units are arbitrary units. Note that the amplitude of the beamformer object echo (in units of acoustic pressure, Pa) for zero rotation and translation is much greater than the echo for 1 degree and 1 millimeter of rotation and translation. The beamformed object echo as shown is computed over a time range of −2.32 to 2.32 microseconds, which approximately corresponds to the −60 dB envelope level of the transmitted Gaussian pulse.

As detailed above as a method of detecting the object and determining the position and orientation of the object, the power of the beamformer object echo may be integrated over a time window according to $g(M_A,T,M_O)$ shown above. One such time window is shown in FIG. 5, with corresponding times $t_1$ and $t_2$ plotted as vertical lines. Here, $t_1=-t_c^{-6\ dB}$ and $t_2=t_c^{-6\ dB}$ as computed according equations given above for $t_c^{-6\ dB}$ and the Gaussian pulse parameters used in the simulation. It is understood that $t_1$ and $t_2$ can have other values as well, for example, $\pm t_c^{-12\ dB}$, or other arbitrary values that produce a window of integration that are centered at t=0.

Figure 6:
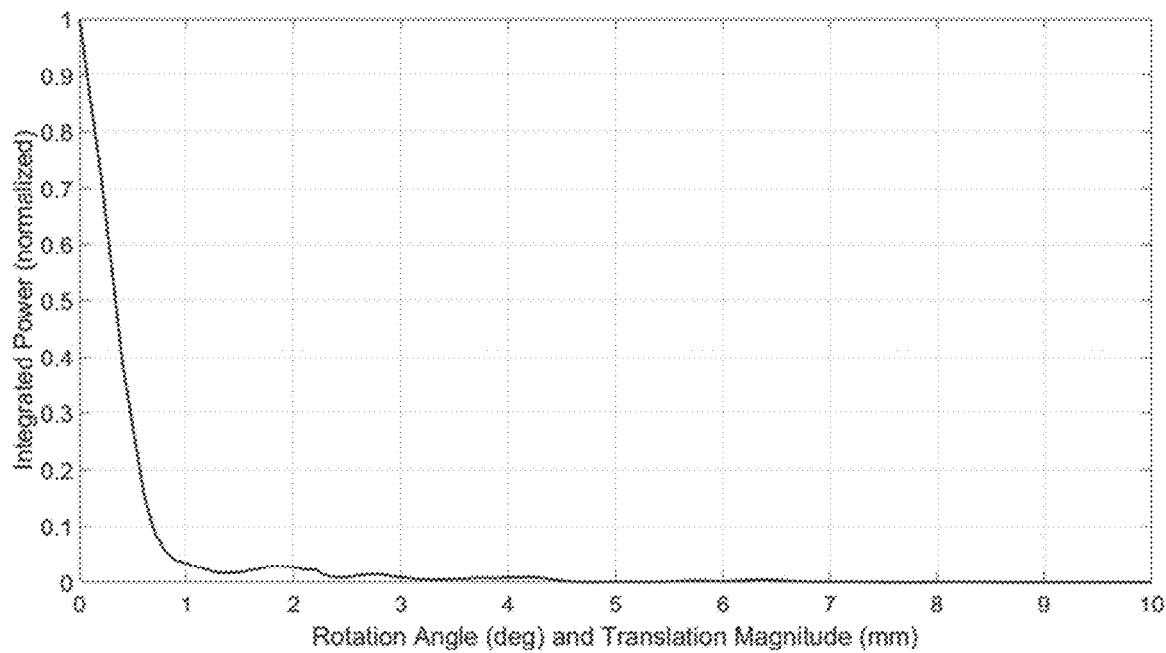
FIG. 6 shows a data plot depicting the normalized integrated power of the output of the example object beamformer shown in FIG. 5 for a range of rotation and translation magnitudes.

FIG. 6 shows a data plot depicting the normalized integrated power of the output of the object beamformer (shown in FIG. 5 for two example positions) for a range of rotation and translation magnitudes ranging from 0 to 10 degrees about the vector [1 1 1] and 0 to 10 millimeters in the direction of [1 −1 1], respectively. The power is normalized by the power obtained for 0 rotation and 0 translation.

The plot of FIG. 6 shows $g(M_A,T,M_O)$ normalized by $g(M_A,T_0,M_O)$, where $T_0$ corresponds to the case of zero rotation and translation (e.g., $T_0$ equals the 4×4 identify matrix). The plot shows a rapid decrease in the beamformed object echo power as a function of increasing transformation values, thus demonstrating the sensitivity of the method for coherently detecting and localizing the object. For example, an appropriately seeded optimizer could find the peak shown in FIG. 6, in order to simultaneously detect and localize the position and orientation of the object. Note that the half-power point is approximately 0.35 degree/millimeter, which is far smaller than the wavelength of 1.5 mm (<λ/4.3), thus illustrating the extremely high sensitivity of the technique to relative movement between the array and the object, which in this example is a small fraction of a wavelength. Given its capacity to localize an object to much less than a wavelength, the synthetic aperture object beamformer may be viewed a super resolution imaging method.

For example, without loss of generality, the assumption of point sources/receivers and point scatterers is expected to hold for larger diffracting apertures and targets, which are typically approximated as groups of point sources/receivers and groups of point scatterers to facilitate fast computations. Also, for example, without loss of generality, the object beamformer is demonstrated for one possible set of arbitrarily chosen trajectories of rotation and translation; however, similar results are expected for other arbitrary rotation and/or translation magnitudes and directions. Also, for example, without loss of generality, the object beamformer is demonstrated for one possible set of arbitrarily chosen set of source/receiver positions representing the array model; however, similar if not better results are expected for other array geometries, particularly if the array surrounds or partially surrounds the object. Also, for example, without loss of generality, the object beamformer is demonstrated for one possible set of arbitrarily set of scatterers representing the object model; however, similar if not better results are expected for larger numbers of points and different geometries.

Example embodiments of the optimizer can include any type of nonlinear optimizer, including, but not limited to: Gauss-Newton method, Nelder-Mead method, Levenberg-Marquardt algorithm, sequential Monte-Carlo method, particle filter method, genetic algorithm, interior-point method, grid search method, and penalty method. Once a viable solution is found by satisfying stopping criteria of the optimizer (e.g., the object is detected), the solution can be used to seed and constrain the optimization for the next set of echoes acquired from the object, which can make the optimization process much faster because the next solution is likely very close to the previous solution, e.g., if the object moves slightly relative to the array.

Other nonlinear objective functions are possible, including finding the maximum over a time window as follows:

$$g(M_A, T, M_O) = \max_{t_1 \leq t \leq t_2} (|f(t, M_A, T, M_O)|).$$

In some implementations, for example, the disclosed systems and methods for tomographic synthetic aperture acoustic imaging can beamform the object pseudo-coherently. In such implementations of pseudo-coherent object beamforming, for example, the system 150 is configured to coherently object beamform regions of the object model separately, and then incoherently combine signals from each region in the objective function. For example, given an object model, $M_O$, comprised of more than one non-intersecting and/or intersecting, but rigidly connected regions, each region may have its own associated object model region, $M_O^m$, where m is the integer index of the particular object model region such that $M_O$ may be defined as follows:

$$M_O = \cup_{m=1}^{N} M_O^m,$$

where ∪ is the union operator and N is the number of regions. Each region may be object beamformed separately, for example, using the notation above, the object beamformer output for a model region, $M_O^m$ is given by $f(t,M_A,T,M_O^m)$. The resulting objective function may be any linear and/or nonlinear combination of $f(t,M_A,T,M_O^m)$, for example, in some implementations, the objective function may be defined as follows:

$$g(M_A,T,M_O)=\Sigma_{m=1}^{N}\int_{t_1}^{t_2}|f(t,M_A,T,M_O^m)|^2 dt,$$

where each object model region, $M_O^m$ is coherently beamformed, the object beamformer power is integrated, and at least some or all of the model regions are incoherently combined with a final summation. A consequence of this objective function formulation is that destructive interference between object beamformed echoes from different regions of the model is prevented due to the incoherent summation, which can aid the optimization process due to a reduction in the number of local maxima around the optimal solution. A basic example of a multiregional object is a three-body object comprised of three spheres with equal radii arranged in an equilateral triangle by rigid connections between the spheres. The object is naturally divided into three regions, with each region corresponding to one of the three spheres (neglecting the rigid support structure of the spheres).

In some implementations, the object model, $M_O$, may be comprised of more than one non-intersecting and/or intersecting, and possibly unconnected regions (e.g., randomly sampled), each region may have its own associated object model region, $M_O^m$, where m is the integer index of the particular object model region such that $M_O$ may be defined as follows:

$$M_O = \cup_{m=1}^{N} M_O^m,$$

where $\cup$ is the union operator and N is the number of regions.

In implementations of coherent or pseudo-coherent object beamforming, for example, the optimizer is seeded with an initial guess, which may be determined in a number of ways, for example, by a priori knowledge of approximately where the object is relative to the array, for example, based on external measurements or observations. Random seed values may be tested until one gives a significantly better optimization result than others, e.g., a lower minimum upon termination of the optimization. Seed values may also be tested using a gridded search over a range of possible orientations and positions, which may be constrained to speed up the process.

Once the optimizer determines $T_{opt}$, the transformation represents the position of the array in the frame-of-reference of the object model. To display the object model in the frame-of-reference of the array, the vertices of the object model must be transformed by the inverse of $T_{opt}$, denoted by $T_{opt}^{-1}$, which is mathematically equivalent to a rotation component of $R_{opt}^{-1} = R_{opt}^T$ (R transposed) followed by a translation component of $-R_{opt}^T h_{opt}$ as follows:

$$T_{opt}^{-1} = \begin{bmatrix} r_{11} & r_{21} & r_{31} & -(r_{11}h_1 + r_{21}h_2 + r_{31}h_3) \\ r_{12} & r_{22} & r_{32} & -(r_{12}h_1 + r_{22}h_2 + r_{32}h_3) \\ r_{13} & r_{23} & r_{33} & -(r_{13}h_1 + r_{23}h_2 + r_{33}h_3) \\ 0 & 0 & 0 & 1 \end{bmatrix},$$

where $$R_{opt} = \begin{bmatrix} r_{11} & r_{12} & r_{13} \\ r_{21} & r_{22} & r_{23} \\ r_{31} & r_{32} & r_{33} \end{bmatrix} \text{ and } h_{opt} = \begin{bmatrix} h_1 \\ h_2 \\ h_3 \end{bmatrix}.$$

The transformation and model can be transferred to the UI and Display Unit 158, e.g., as shown in FIG. 1E, which performs the transformation on the model and displays the model relative to the array.

In some implementations, for example, the objective function can also be formulated such that the optimizer minimizes the inverse of $g(M_A, T, M_O)$, i.e., $$\frac{1}{g(M_A, T, M_O)},$$

in order to detect and localize the position and orientation of an object, e.g., $$T^{opt} = \arg\min_T \frac{1}{g(M_A, T, M_O)}.$$

For example, most optimization algorithms are formulated to minimize objective functions.

In some implementations, for example, the object beamformer can be configured to neglect object model parameters, $M_O$, that may vary the object model's geometry, and to neglect array model parameters, $M_A$, that may vary the array's geometry; however, varying such parameters is expected to have similar effects on the objective function $g(M_A, T, M_O)$. For example, by varying the scale of the object model, e.g., by multiplying the model coordinates by constant scale factor in each dimension, the optimizer could determine the optimal value of the scale factor. As another example, if the object model is a sphere, the radius of the sphere could be varied by the optimizer to determine the optimal value of the radius. In some implementations, for example, the optimization of model parameters (i.e., $M_O$ and/or $M_A$) is performed simultaneously with the optimization of the transformation, T. In other implementations, for example, the optimization of model parameters (i.e., $M_O$ and/or $M_A$) and transformation, T, are performed independently.

In some implementations, for example, other parameters, besides $M_O$, $M_A$, and T, relating to acoustic properties can be varied and optimized, including but not limited to: global acoustic medium sound speed, acoustic medium sound speeds local to each transmitter and receiver, global acoustic medium attenuation, acoustic medium attenuation local to each transmitter and receiver, global medium acoustic impedance, and acoustic impedance local to each transmitter and receiver, acoustic impedance of the object, acoustic impedance of the object local to each transmitter and receiver, and acoustic impedance of the transducer array. For example, such parameters may be lumped into the object beamformer as follows:

$$f(t, M_A, T, M_O, Z) = \sum_{i=1}^{NTX} \sum_{j=1}^{NRX} \sum_{k=1}^{NMP} w_{ijk}(M_A, T, M_O, Z) s_{ij}(t - \tau_{ijk}(M_A, T, M_O, Z)),$$

where the set of parameters, Z, denotes additional acoustic parameters that affect the object beamformer output, e.g., sound speed, attenuation, acoustic impedance, etc. Herein, acoustic properties relating to the transducer array itself (e.g., matching layers, lens material, etc.), the medium between the transducer array and the object (e.g., water or other coupling medium), and the acoustic medium comprising the object itself (e.g., steel other material) are referred to as acoustic properties.

In the case of using the object beamformer to optimize medium sound speed, for example, the optimizer can be seeded with an initial guess of the sound speed, e.g., 1500 m/s, or a sound speed can be estimated from pitch-catch measurements between spatially separated transmitters and receivers, and the estimates can be used to seed the optimizer. If the exact or very good approximation of the object model is known a priori, and the array geometry is known a priori, then the optimized sound speeds can be used to improve conventional synthetic aperture or real aperture imaging around the object.

In some implementations, for example, other parameters comprising the array model, $M_A$, besides points, normal vectors, etc. relating to the geometry of the array may be varied and optimized, including but not limited to, array element positions, array element normal directions, array element dimensions, array element shape, and array element rotations about array element positions. For example, one such application of an extended parameter set $M_A$ would be for the process of calibrating a given array under precisely known object geometry, object properties, and medium properties.

In some implementations, for example, other parameters comprising the object model, $M_O$, besides points, normal vectors, areas, curvatures, regions, etc. relating to the geometry of the object may be varied and optimized, including but not limited to parameters associated with: rigid transformations, non-rigid transformations, affine transformations, perspective transformations, non-uniform transformations, a statistical model of the object, a mathematical model of the object (e.g., an analytical model), and a numerical model of the object (e.g., a polynomial fit).

In some implementations, for example, other parameters that affect object beamformer output may be included in the same way that parameters $M_A$, T, $M_O$, Z have been included above. For example, including but not limited to: parameters relating to the electrical characteristics of the transducers, parameters relating to the time domain impulse response of the transducers, parameters relating to the spatial impulse response of the transducers, parameters relating to the center frequency of the transmitted waveforms, parameters relating to the bandwidth of the transmitted waveforms, and parameters relating to the delays of the transmitted waveforms.

In some embodiments of the disclosed object imaging system, the synthetic aperture array geometry is pre-optimized for a given object such that small perturbations to the position and orientation of the object generate maximum change in the object beamformer output, i.e., to optimize sensitivity to small translational and/or rotational displacements.

In some embodiments of the disclosed object imaging system, the synthetic aperture array geometry is pre-optimized for a given object such that redundancy of spatial sampling on the surface of the object is minimized, i.e., such that spatial samples are approximately uniformly distributed over the object. For example, the array geometry for a spherical object would ideally be spherical. Likewise, for example, the array geometry for a cylindrical object would ideally be cylindrical.

In some embodiments of the disclosed object imaging system, the synthetic aperture array geometry provides at least as many spatial samples as there are unknowns being solved for by the optimizer.

Figure 7:
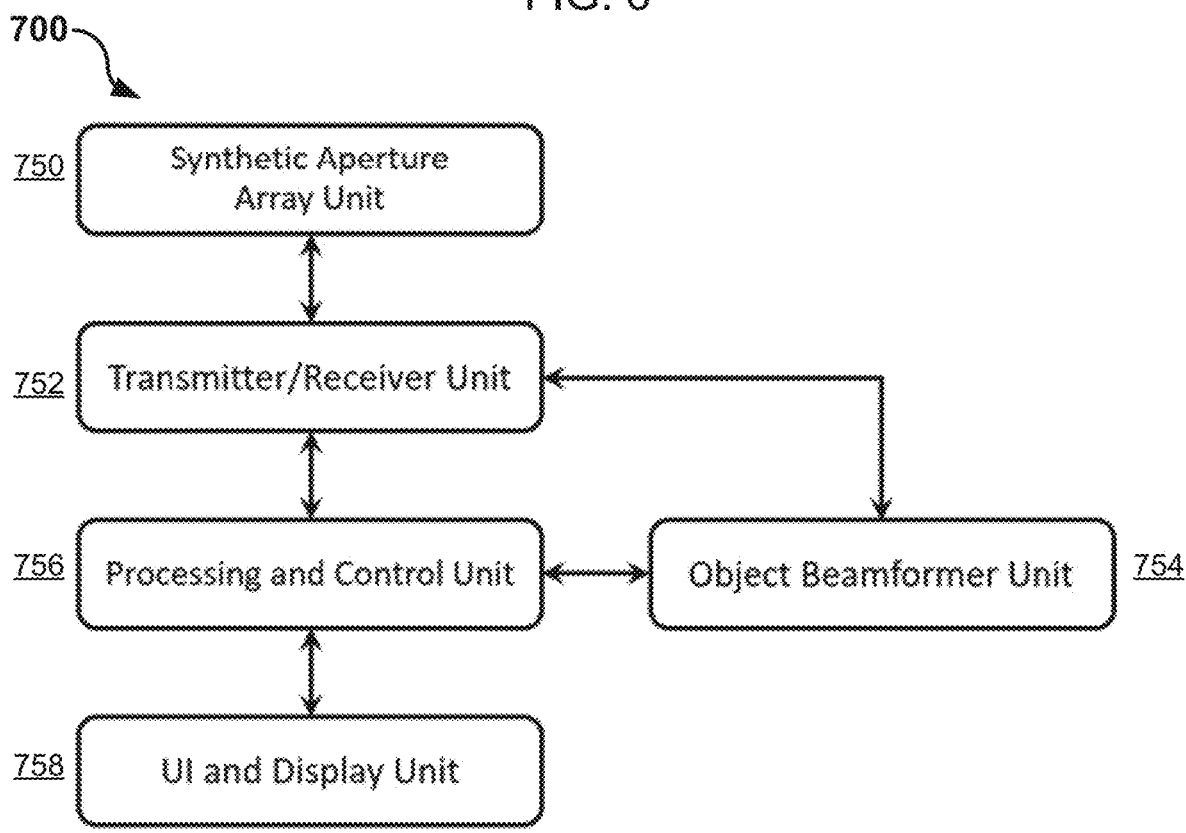
FIG. 7 shows a diagram of another example embodiment of a tomographic synthetic aperture object imaging system in accordance with the present technology.

FIG. 7 shows a diagram of an example embodiment of a synthetic aperture object imaging system in accordance with the present technology, referred to as synthetic aperture object imaging system 700 or system 700. The synthetic aperture object imaging system 700 includes hardware and software subsystems, including a synthetic aperture array unit 750 that is in communication with a transmitter/receiver unit 752 of the system 700, which the transmitter/receiver unit 752 is in communication with a processing and control unit 756 and an object beamformer unit 754 of the system 700. In some embodiments, for example, the system 700 optionally includes a user interface and display unit in communication with the processing and control unit. In some embodiments, for example, the system 700 is operable to implement the disclosed techniques as discussed above and/or include features discussed in relation to the system 150 shown in FIG. 1E.

FIG. 8A shows a diagram illustrating an example embodiment of a method 800 for tomographic synthetic aperture imaging of an object by beamforming the object as a whole in accordance with the present technology. The method 800 includes a process 810 to transmit, receive, and/or transmit and receive acoustic signals at an object that forms a synthetic aperture based on transmitting of transduced acoustic waveforms at the object and receiving returned acoustic echoes from the object. In some embodiments of the process 810, the transmitted acoustic waveforms can be formed as composite waveforms, which, further, can be spatially encoded, temporally encoded, or spatially and temporally encoded. In some embodiments of the process 810, when transmitted acoustic waveforms are spatially encoded, temporally encoded, or spatially and temporally encoded, the process 810 may include decoding of encoded received waveforms.

The method 800 includes a process 815 to beamform the object using echo samples of the returned acoustic echoes from one or more regions of the object to produce one or more beamformed output signals. For example, the one or more beamformed output signals can be functions of one or more inputs for the beamforming, where the one or more inputs for the beamforming includes information representative of the object. In some implementations of the process 815, the object is beamformed by coherently combining (e.g., summing and/or multiplying) delayed and weighted echo samples of the returned acoustic echoes from the one or more regions of the physical object to produce the one or more beamformed output signals. In some implementations of the process 815, the process 815 includes generating delayed echo samples, e.g., comprising real or complex radio frequency (RF) sample waveforms $s_{ij}(t-\tau_{ijk}(M_A,T,M_O))$ as discussed above, and weighting factors, e.g., comprising $w_{ijk}(M_A,T,M_O)$ as discussed above, corresponding to (i) a plurality of transmitter positions (indexed i) and receiver positions (indexed j) of a transducer array, at least partially comprising array model $M_A$, (ii) a plurality of points of an object model (indexed k), at least partially comprising object model $M_O$, and/or (iii) attributes of the transformation, T, relating the relative position and orientation of the array to the model. In some nonlimiting embodiments, for example, the process 815 to generate the object beamformer output samples includes summation of delayed and weighted echo samples computed by the equation:

$$f(t,M_A,T,M_O)=\sum_{i=1}^{NTX}\sum_{j=1}^{NRX}\sum_{k=1}^{NMP}w_{ijk}(M_A,T,M_O)s_{ij}(t-\tau_{ijk}(M_A,T,M_O)),$$

with the parameters discussed above. For example, the one or more beamformed output signals produced at the process 815 are functions of one or more inputs for the beamforming process, discussed below with respect to FIGS. 8C and 8D. In implementations of the method 800, the process 815 to beamform the object includes producing one or more coherently-beamformed output signals (e.g., one or more object beamformed echoes) in a digital format. In implementations of the method 800, the process 815 to beamform the object includes producing one or more pseudo-coherently-beamformed output signals (e.g., one or more object beamformed echoes) in a digital format.

The method 800 includes a process 820 to optimize the one or more beamformed output signals to determine (one or more of) a position, an orientation, a geometry, and/or a physical property or set of physical properties of the object. Examples of a physical property or set of physical properties include, but are not limited to, the density, bulk modulus, an acoustic property or properties, such as an acoustic impedance, surface reflections, volumetric or internal reflections, acoustic absorptions, etc., or other physical properties of the object. In some embodiments of the process 820, the determination of the position, orientation, geometry, and/or physical or acoustic properties of the object from the optimization of the one or more beamformed output signals includes generating one or more scalar outputs that are based on the one or more beamformed output signals; optimizing the one or more scalar outputs as a function of at least some of a position, an orientation, a geometric property, or a physical property of the object; and detecting the object by determining a degree of optimization of one or more objective functions based on values of or changes in inputs and outputs of an optimization, using an optimizer, compared to detection criteria.

The method 800 includes a process 840 to produce an image of the object based on a rendition of the optimized position, orientation, the geometric properties, and/or the properties of the object (e.g., physical properties, including surface properties, volumetric properties, and/or acoustic properties).

For example, in some embodiments of the method 800, the process 820 can include a process 821 to generate one or more scalar outputs that are based on the one or more beamformed output signals. In some implementations of the process 821, for example, one or more scalar outputs are generated by summing the power of the one or more coherently beamformed output signals over a time window determined by the center frequency and bandwidth of the transmitted pulse as described above. As discussed in further detail with respect to FIGS. 8C and 8D, the one or more scalar outputs can correspond to the outputs of one or more objective functions. One or more inputs to the beamforming process 815 (e.g., parameters describing the object, array, and their relative position and orientation; acoustic properties) are the independent variables of the one or more objective functions.

In some embodiments of the method 800, the process 820 can include a process 825 to optimize the one or more scalar outputs as a function of at least some of the position, the orientation, or geometry of the transducer array, and/or at least some of the position, the orientation, the one or more geometric properties, and/or the physical properties (e.g., surface or volumetric property) of the object and/or acoustic properties of the object. For example, the process 825 optimizes one or more objective functions using an optimizer (i.e., an optimization algorithm) to produce one or more optimizer outputs. In some example implementations, the one or more optimizer outputs produced at the process 825 includes, but not limited to, the norm of object parameters, the norm of array parameters, one or more optimality measures, one or more feasibility measures, one or more residuals, and/or step size information. In implementations of the process 825, for example, the one or more scalar outputs is optimized by varying parameters associated with the array of transducer elements and/or the model of the object and/or the transformation relating the object to the array in space, and/or acoustic properties. In this way, the one or more scalar outputs is a function of parameters associated with the array of transducer elements and/or the model of the object and/or the transformation relating the object to the array in space, and/or parameters associated with acoustic properties, i.e., forming an objective function (e.g., at the process 821) that is optimized by an optimizer (i.e., an optimization algorithm). The one or more optimized parameters can include, but are not limited to, (i) at least one output of the objective function, i.e., at least one dependent variable, e.g., such as an integrated object beamformed echo power, and/or (ii) at least one output of the objective function, i.e., at least one independent variable, e.g., including but not limited to parameters describing the position and orientation of the object, parameters describing the geometry of the object, parameters describing properties of the object, parameters describing the position and orientation of the array, parameters describing the geometry of the array, and/or parameters describing acoustic properties.

In some implementations of the method 800, the process 825 determines the position, the orientation, one or more geometric properties, and/or one or more physical properties of the object and/or one or more acoustic properties of the object based on the one or more beamformed output signals produced at the process 815 and further refined in process 821 in response to varying attributes of the transducer array and attributes of the object model to optimize one or more attributes of the one or more beamformed output signals.

In some embodiments of the method 800, the process 820 can include a process 830 to detect the object by determining a degree of optimization of one or more objective functions (e.g., process 821) based on (i) values of and/or (ii) changes in inputs and outputs of an optimizer with respect to (e.g., compared to) detection criteria or stopping criteria (e.g., one or more thresholds). In some implementations, the process 830 detects the object by comparing the one or more scalar output to a threshold value, e.g., a value of total integrated power is satisfied. In some implementations, the determined degree of optimization can be based on a detection decision where optimized variables (e.g., object parameters, object position, objection orientation) satisfy a threshold value (e.g., detection criteria or stopping criteria). In some implementations, the determined degree of optimization can be based on a detection decision where changes in optimized variables (e.g., object parameters, object position, objection orientation) between two or more iterations of the optimizer satisfy a threshold value (e.g., detection criteria or stopping criteria). In some implementations, detecting the object may include localizing one or more regions of the object as a function of the geometry, position, and/or orientation of the array of transducer elements (e.g., transducers, receivers, and/or transceivers) and the position and/or orientation of one or more regions (e.g., one or more different sets of points) on the object model by maximizing the power contained within one or more beamformed output signals. In this manner, the process 830 detects the object by determining at least some of the position, the orientation, geometric properties, and/or the physical properties of the object and/or the acoustic properties of the object based on one or more optimized parameters and optimization criteria applied to one or more optimized parameters, e.g., as discussed in further detail with respect to FIG. 8C.

In some implementations, for example, the process 830 detects the object by determining a degree of optimization based on absolute values and/or changes between iterations in the inputs and/or outputs of the optimizer. For example, optimizers must iterate as they search for and refine solutions (e.g., maximize an objective function). For example, inputs may be comprised of one or more scalar outputs of one or more objective functions (e.g., from process 821), and outputs may be comprised of geometry, position and/or orientation of the array and/or geometry, position, and/or orientation of one or more regions (e.g., one or more different or overlapping sets of points) on the object model.

In some implementations of the process 830, in the process of optimizing one or more inputs, if the values of one or more inputs exceed one or more respective absolute thresholds, thus satisfying a degree of optimization, the process 830 may signal that the object is detected. In some implementations, in the process of optimizing one or more inputs, if the differential change in values of one or more inputs between two or more iterations of the optimization algorithm fall below one or more respective thresholds, thus satisfying a degree of optimization, the process 830 may signal that the object is detected. In some implementations, in the process of optimizing one or more inputs, the object may be detected by a combination of one more inputs exceeding one or more thresholds and/or the differential change in one or more inputs falling below one or more thresholds.

Since the outputs of the optimization algorithm are generally unknown, e.g., initially, the object has an unknown position and orientation relative the array, detection thresholds based on the absolute values of the one or more outputs from the optimization algorithm are generally not considered for detection except to possibly validate, for example, that the optimized position and orientation are within reasonable limits. For example, if the optimized position and orientation are outside of reasonable limits, then the object cannot be detected. Thus, in some implementations of the process 830, in the process of optimizing one or more outputs, if the values of one or more outputs fall outside of one or more ranges or limits, thus not satisfying a degree of optimization, the process 830 may signal a determination that the object is not detected.

In some implementations of the process 830, in the process of optimizing one or more outputs, if the differential change in values of one or more outputs between two or more iterations of the optimization algorithm fall below one or more respective thresholds, thus satisfying a degree of optimization, the process 830 may signal a determination that the object is detected. For example, if the norm (e.g., vector length) of the array position output of the optimizer changes by less than a specified amount, the optimization algorithm has converged, and the object is detected.

In some implementations of the process 830, a norm or function operating on a vector to produce a scalar measure of the vector may be computed across all optimizer output variables (e.g., Euclidean norm or length of a multidimensional vector) or one or more subsets of optimizer output variables (e.g., array position is one subset, array orientation is another subset, and so on). One or more norms may be normalized and/or linearly or nonlinearly combined to compute a composite norm or scalar value as a function of two or more outputs of the optimizer. In accordance with previously described implementations of the process 830 and without limitation, one or more norms may be substituted in place of outputs of the optimizer for determination of the degree of optimization, and without limitation, separate detection criteria may be associated with one or more norms as outputs of the optimizer. The vector norm can be used as an optimizer convergence measure, for example, when objective functions contain a large number of independent variables.

In some implementations of the process 830, the norm may include any function applied to a vector of optimized outputs that produces a scalar measure, that may include, but is not limited to, Euclidean norm (also referred to as $L^2$ norm, $l^2$ norm, 2-norm, or square norm), Manhattan norm (also referred to as 1-norm, Manhattan distance, $l_1$ norm, $l_1$ distance, or taxicab norm), p-norm, maximum norm, composite norm, asymmetric norm, and Mahalanohis distances.

Figure 8B:
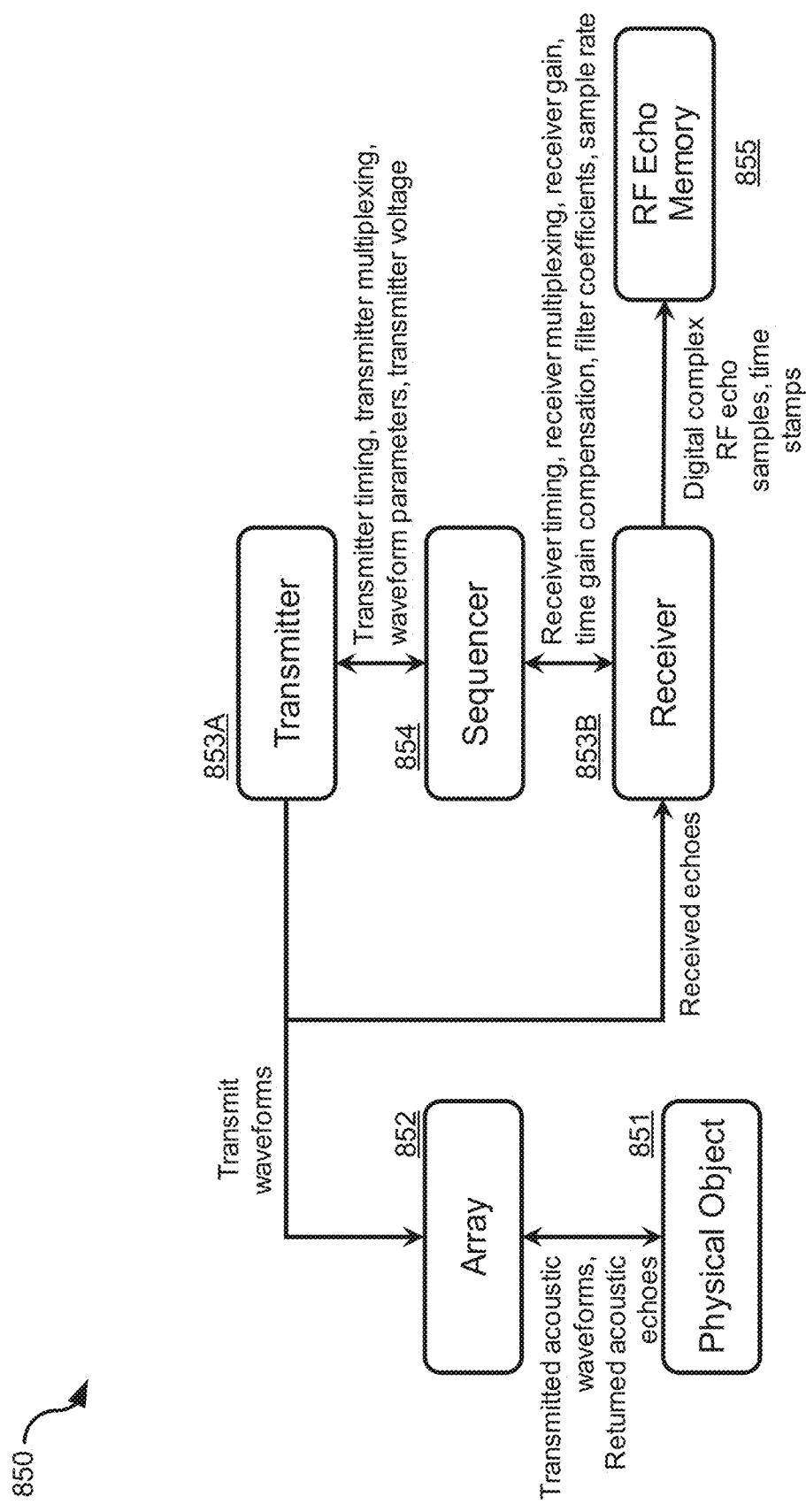
FIG. 8B shows a data and variable flow diagram illustrating an example embodiment of front-end hardware and software modules operable on the tomographic synthetic aperture object imaging system shown in FIG. 7 and in accordance with the method of FIG. 8A.

FIG. 8B shows a diagram illustrating an example embodiment of a front-end subsystem 850 in accordance with example embodiments of an object imaging system of the disclosed technology, depicting data flow and example variables in communication between different functional subsystems executable in hardware and software, and in accordance with the method 800 shown in FIG. 8A.

For example, the diagram of FIG. 8B depicts a physical object 851 acoustically interrogated by transmitted acoustic waveforms (e.g., through a medium supporting acoustic waves) that are generated and controlled by transmitter 853A and transduced by an array of transducer elements 852, e.g., according to the process 810 discussed shown in FIG. 8A. In some embodiments, the array of transducer elements 852 include an arrangement of the transducer elements organized in a contiguous arrangement, a discontiguous arrangement, a symmetric arrangement, an asymmetric arrangement, one or a plurality of transducer segments or sub-arrays, or other arrangements. In some embodiments, for example, the array of transducer elements 852 is included in a single acoustic probe unit or device; whereas in some embodiments, for example, the array of transducer elements 852 is included in multiple acoustic probe units or devices. Also, according to process 810, the returned echoes (e.g., reflected and/or scattered echoes) are transduced by the array of transducer elements 852 and processed (e.g., amplified, sampled, and/or filtered) by receiver 853B, which stores digital complex radiofrequency (RF) samples in the one or more memory units (e.g., illustrated in the diagram of FIG. 8B as RF echo memory 855), e.g., which can include a non-transitory computer readable medium, such as random-access memory (RAM). The timing, multiplexing, and parameters associated with the generation of waveforms by the transmitter 853A are controlled by a sequencer unit 854, which is also in coordinated and time-base referenced communication with the receiver 853B such that transmissions and receptions are coherent, e.g., reception occurs after a deterministic and known period of time after transmission according to a digital clock or timer. In this way, real or complex or quadrature digital samples stored in RF echo memory 855 have known timing, e.g., time stamps and sample rate, in accordance with coherent transmission and reception.

Figure 8C:
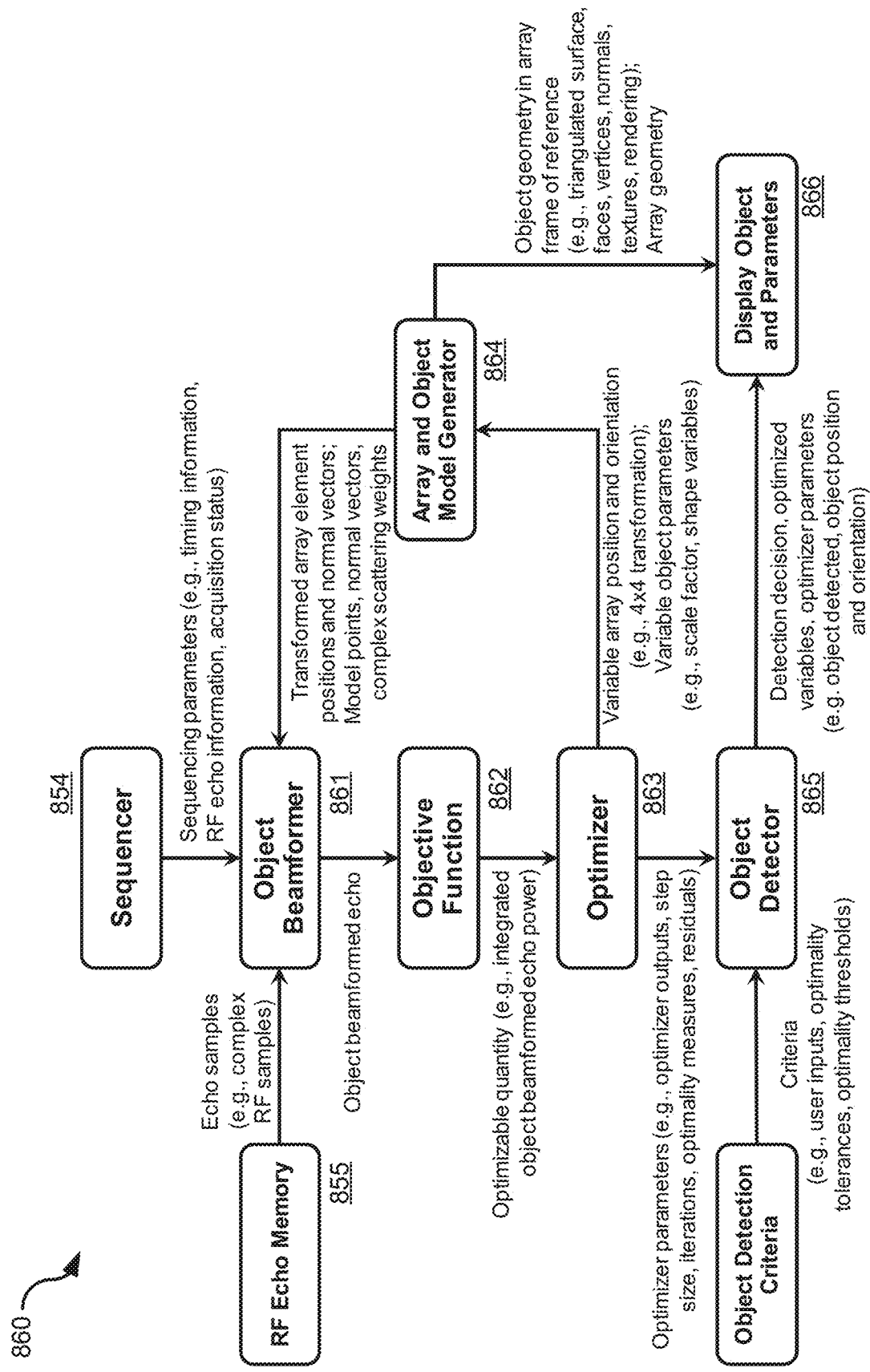
FIG. 8C shows another data and variable flow diagram illustrating an example embodiment of back-end hardware and software modules operable on the tomographic synthetic aperture object imaging system shown in FIG. 7 and in accordance with the method of FIG. 8A and in continuation of the embodiment of FIG. 8B.

FIG. 8C shows a diagram illustrating an example embodiment of a back-end subsystem 860 in accordance with example embodiments of an object imaging system of the disclosed technology, depicting data flow and example variables in communication between different functional subsystems executable in hardware and software, and operable to implement the disclosed methods, including the method 800 shown in FIG. 8A.

The diagram of FIG. 8C depicts a continuation of FIG. 8B, where the processed and sampled acoustic echoes as echo samples (e.g., digital complex RF samples) storable in memory, as described above, can be passed as data to the object beamformer 861 to be processed by an object beamforming algorithm in accordance with the present technology, e.g., implementing at least some processes of the method 800 discussed above.

For example, in some implementations of the processes 815-830 described with respect to FIG. 8A, the beamformed output signals (e.g., digital signals representative of non-scalar waveforms) can be passed to objective function 862 to generate an optimizable (scalar) quantity (e.g., integrated object beamformed echo power). For example, the optimizable (scalar) quantity can be used by the optimizer 863 (e.g., optimizer algorithm executable by the object beamformer unit and/or the data processing unit) to change variables describing the array model, object model, and their relative position and orientation. For example, the variables describing the array model, the object model, and their relative position and orientation (e.g., 4×4 transformation) generated by the optimizer 863 can be passed to an array and object model generator 864, which can be embodied as an algorithm for modification of the array model and/or object model. In such implementations, a new or modified array model and/or a new or modified object model can be passed into the object beamformer 861 to re-beamform the object, i.e., iteratively repeat the object beamforming process. The resulting beamformed output signals, e.g., optimized or unoptimized, can be passed again through the objective function 862 and the optimizer 863. In accordance with processes 815-830 in FIG. 8A, the output of the optimizer can be passed to the object detector 865, which determines based on depicted object detection criteria (e.g., thresholds, tolerances, stopping criteria, optimizer convergence measures) if the object is detected. If the object is detected, a representation of the detected object and object parameters can be displayed at display object and parameters module 866 (e.g., the user interface and display unit), according to process 840 described above.

Figure 8D:
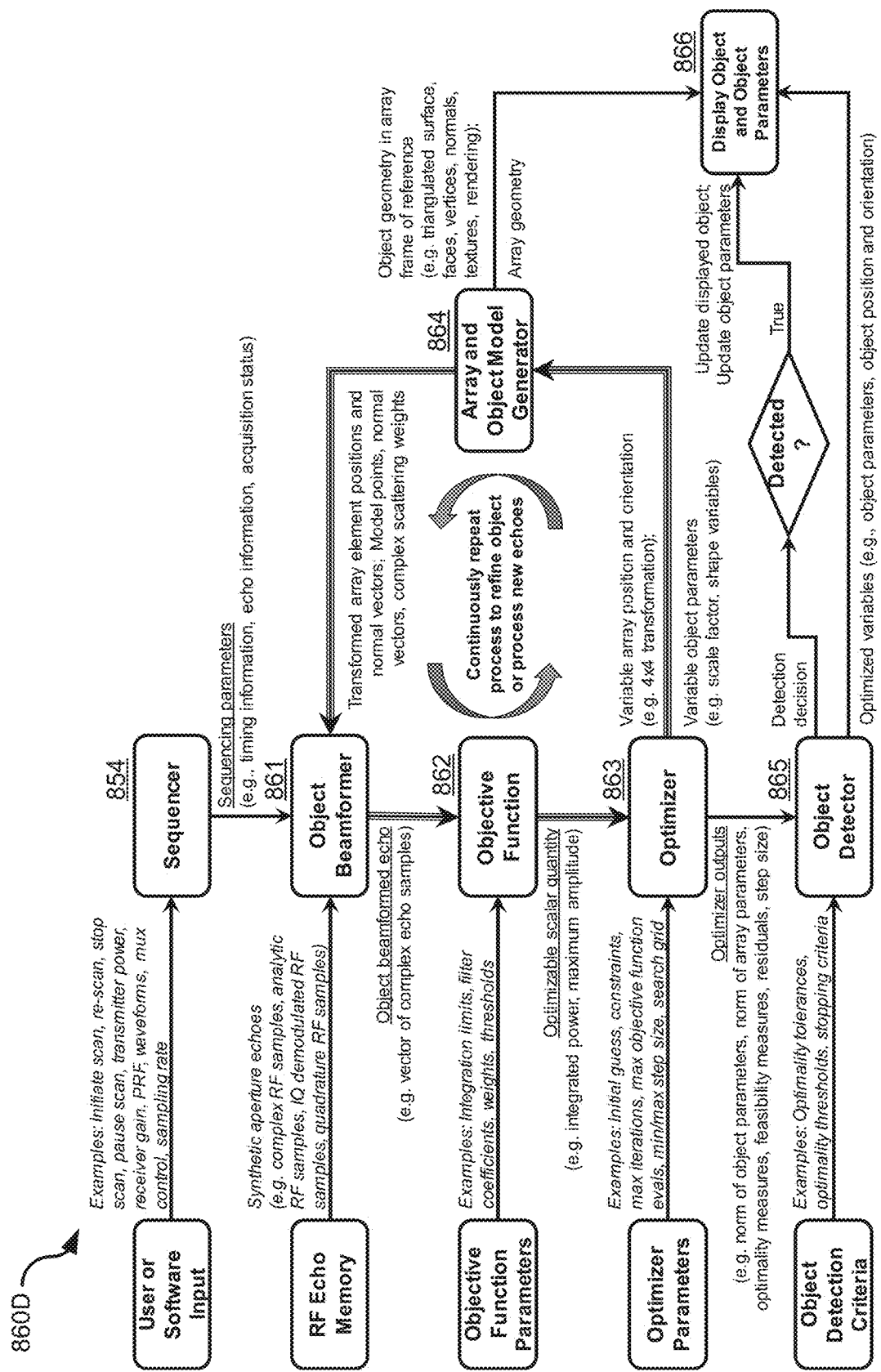
FIG. 8D shows another diagram as in FIG. 8C of an example embodiment of the back-end hardware and software modules operable on the tomographic synthetic aperture object imaging system shown in FIG. 7 and in accordance with the method of FIG. 8A and in continuation of the embodiment of FIG. 8C.

FIG. 8D shows another diagram of an example embodiment of the back-end subsystem 860D in accordance with example embodiments of an object imaging system of the disclosed technology operable to implement the disclosed methods, including the method of FIG. 8A. The diagram of the example back-end subsystem 860D in FIG. 8D provides further details in some implementations of the embodiment of the back-end subsystem 860 shown in FIG. 8C.

As shown in the diagram (of FIG. 8D), in some implementations of the processes 815-830 described with respect to FIG. 8A, multiple inputs can be provided to the object beamformer 861 to produce the beamformed output signal(s). For example, the sequencer 854 provides sequencing parameters (e.g., timing information, echo information, acquisition status, or other) based on a sequencing algorithm that utilizes input, e.g., from a user and/or automated inputs, such as commands like initiate scan, re-scan, stop scan, and/or other parameters like transmitter power, receiver gain, etc. Also, for example, the object beamformer 861 receives echo information, e.g., from the RF echo memory 855 (shown in FIG. 8B), which includes the synthetic aperture echoes, e.g., comprising complex RF samples, analytic RF samples, IQ demodulated RF samples, quadrature RF samples, and/or other echo samples. The beamformed output signals (e.g., the object beamformed echo, which can be a vector of complex echo samples and represented digitally) can be passed to objective function 862 to generate, e.g., based on objective function parameters (examples: integration limits, filter coefficients, weights, thresholds, etc.), an optimizable (scalar) quantity (e.g., integrated object beamformed echo power, maximum amplitude, or other). For example, the optimizable (scalar) quantity can be used by the optimizer 863 (e.g., optimizer algorithm executable by the object beamformer unit and/or the data processing unit) to change variables describing the array model, object model, and their relative position and orientation (e.g., 4×4 transformation). The optimized variables and/or optimized outputs are determined by the optimizer 863 using optimizer parameters, e.g., including an initial guess result (such as for the first output), constraints, max iterations, max objective function evaluations, min/max step size, search grid, or other parameters. For example, the variables describing the array model and the object model, such as variable array position and orientation, generated by the optimizer 863 can be passed to an array and object model generator 864, which can be embodied as an algorithm for modification of the array model and/or object model. In such implementations, a new or modified array model and/or a new or modified object model can be passed into the object beamformer 861 to re-beamform the object, i.e., to iteratively repeat the object beamform process. The resulting beamformed output signals, e.g., optimized or unoptimized, can be passed again through the objective function 862 and the optimizer 863. In accordance with processes 815-825 in FIG. 8A, the output of the optimizer can be passed to the object detector 865, which determines based on object detection criteria (e.g., stopping criteria, tolerances, and/or thresholds) if the object is detected. If the object is detected, a representation of the detected object and object parameters can be displayed at display object and parameters module 866 (e.g., the user interface and display unit), according to process 840 described above. Also, the object detector 865 is able to provide optimized variables (e.g., object parameters, object position and orientation information) to the display object and parameters module 866 to produce the image. The produced image can also be used in the update or modification of the object model, for example, where object geometry in the array frame of reference (e.g., triangulated surface(s), face(s), vertex/vertices, normal(s), area(s), texture(s), and/or rendering(s)) and/or array geometry information can be provided to the array and object model generator 864 from the display object and object parameters module 866.

Example features of the embodiments of a synthetic aperture acoustic imaging system, like that shown in FIGS. 1, 7 and 8A-8D and/or discussed throughout this patent disclosure, can include the following.

In some embodiments, for example, an acoustic imaging system for imaging scattering characteristics of an object, contained within a medium with different acoustic impedance than the object, includes (i) an array of transducer elements operable to transmit, receive, and/or transmit and receive acoustic signals by forming a synthetic aperture of the system; (ii) transmitter and receiver circuitry coupled to the array of transducer elements and configured to produce and/or process transmit acoustic waveforms (e.g., digital signals) to be transduced and transmitted by selected transmit transducer element(s) of the array, and configured to convert received acoustic echoes (received at selected receive transducer element(s)) to digital signals representative of acoustic return echo waveforms; (iii) a digital beamformer unit operable to store and/or generate a model of the object, and to compute delays and weights based on the array geometry and object model geometry, and to generate digital signals derived from beamforming received echoes according to computed delays and weights; (iv) a data processing unit comprising a processor and a memory to operate as a data processing and control unit of the system that is configured to control transmit and receive sequencing, and configured to control the beamformer unit in order to determine surface properties based on the digital signals produced by the beamformer; (v) and a display unit operable to produce an image of the object based on a rendition of the position, orientation, and surface properties as determined by the data processing unit.

In some embodiments of the acoustic imaging system for imaging surface reflection characteristics of the object, for example, the digital beamformer unit is configured to compute delays determined from each transmitter position to points on the model and back to each receiver position; to compute weights for specular scattering, acoustic field directivity, and complex reflectivity according to vectors of incidence, vectors of reflection, vectors of reception, transducer normal vectors, object face normal vectors, and/or a priori information about the object relating to the complex reflectivity; and to apply the computed delays and the computed weights to stored echoes prior to summing delayed and weighted echoes to produce a single beamformed echo.

In some embodiments, one or more beamformed echoes are processed with additional analysis and filtering, including, but not limited to, finite impulse response filters, infinite impulse response filters, low pass filters, high pass filters, bandpass filters, matched filters, autocorrelation, cross-correlation, envelope detection, demodulation, Wiener filters, nonlinear filters, causal filters, noncausal filters, digital filters, frequency domain filters, time domain filters, principle component analysis, wavelet analysis, Fourier transforms, filter banks, time-frequency analysis, cyclostationary analysis, singular value decompositions, Eigen decompositions, interlaced decompositions, even/odd decompositions, adaptive filters, interpolators, deconvolution filters, inverse filters, and neural networks.

In some embodiments of the acoustic imaging system for imaging reflection characteristics of the object, for example, the data processing unit is configured to integrate beamformer echo power over a time window, and to optimize a transformation applied to array element positions and normal vectors as inputs to the beamformer in order to maximize said integrated beamformer echo power over a time window.

In some embodiments of the acoustic imaging system for imaging reflection characteristics of the object, for example, the display unit is configured to visualize the object in the frame of reference of the array according to the inverse of the optimized transformation.

In some embodiments of the system, for example, the array of transducer elements includes one or more transmitter transducer elements and one or more receiver transducer elements that are spatially separated, e.g., positioned adjacent, to an object. In some embodiments, for example, the one or more transmitter transducer elements and one or more receiver transducer elements are fully or at least partially surrounding the object.

In some embodiments of the system, for example, the array of transducer elements includes at least three transducer elements creating at least three monostatic reflection samples and at least three bistatic reflection samples of the object, such that the samples are significantly separated on the surface of the object.

In some embodiments of the system, for example, the array of transducer elements includes an array geometry configured to produce at least six independent monostatic or bistatic reflection samples of the object such that the samples are significantly separated on the surface of the object.

In some embodiments of the system, for example, the model of the object includes vertices and faces approximating the object with faces no larger than one acoustic wavelength resolution. In some embodiments, for example, the faces are one-half acoustic wavelength resolution or less.

In some embodiments of the system, for example, the model of the object includes points and surface normal vectors corresponding to each point that approximate the object with at most one-wavelength acoustic resolution. In some embodiments, for example, the points and surface normal vectors corresponding to each point approximate the object with less than one-half acoustic wavelength resolution.

In some embodiments of the system, for example, in addition to points and surface normal vectors, the object model is also comprised of surface curvature parameters relating to the major and minor curvature of the surface at the point.

In some embodiments of the system, for example, the object model is comprised of faces and face normals.

In some embodiments of the system, for example, the object model is comprised of vertices and vertex normals.

In some embodiments of the system, for example, the object model is comprised of both faces and face normals and vertices and vertex normals.

In some embodiments of the system, the object points and normals used within the beamformer are a subset of the points and normals representing the whole object.

In some embodiments of the system, for example, the beamformer unit is configured to compute a first time delay from a transducer element 1 to a face or point on the model, and back to the transducer element 1.

In some embodiments of the system, for example, the beamformer unit is configured to compute a second time delay from the transducer element 1 to a face or point on the model, and back to a transducer element 2.

In some embodiments of the system, for example, the beamformer unit is configured to compute a first weighting factor based on the normal vector of a transducer element 1, the vector of incidence from the transducer element 1 to a face or point on the model, the vector of reflection from the face or point on the model, and the vector of reception from the point or face on the model to the transducer element 1.

In some embodiments of the system, for example, the beamformer unit is configured to compute a second weighting factor based on the normal vector of the transducer element 1, the vector of incidence from the transducer element 1 to a face or point on the model, the vector of reflection from the face or point on the model, the vector of reception from the point or face on the model to the transducer element 2, and the normal vector of the transducer element 2.

In some embodiments of the system, for example, a transmission occurs on a transducer element 1 of the array and subsequent receptions occur on the transducer element 1 and a transducer element 2 of the array, and the echo received on the transducer element 1 is delayed and weighted according to the first delay and the first weighting factor and the echo received on the transducer element 2 is delayed and weighted according to the second delay and the second weighting factor, and both delayed and weighted echoes are summed together in the beamformer resulting in a single beamformed echo output signal.

In some embodiments of the system, for example, a transmission occurs on a transducer element 1 of the array and after a delay a transmission occurs on a transducer element 2 of the array, such that the delay is substantially less than the round-trip time from the transducer element 1 to the nearest point on the object back to the transducer element 2.

In some embodiments of the system, for example, a plurality of weighted and delayed echoes determined for a plurality of faces or points on the model each contribute to a single beamformed echo output signal.

In some embodiments of the system, for example, coordinates of a plurality of transducer elements of the array and their corresponding normal vectors are varied by applying a homogeneous transformation determined by an optimization algorithm in order to maximize the integrated power of the said beamformer single echo signal over a time window duration inversely proportional to the center frequency and bandwidth of the received echoes.

In some embodiments of the system, for example, the model of the object or an equivalent representation of the object used within the beamformer unit is presented on a display relative to a coordinate system of the array by transforming its coordinates using the inverse of said optimized transformation.

In some embodiments of the system, for example, the acoustic impedance of the object is significantly different from the surrounding medium so as to create monostatic and bistatic specular reflections observable from a plurality of transmitter and receiver positions.

In some embodiments of the system, for example, the system is operable such that a transmission event occurs on a group of transducer elements of the array each with individual delays such that the transmission appears to emanate from a single point in space.

In some embodiments of the system, for example, the system is operable such that a reception event occurs on a group of transducer elements of the array where each group is separately beamformed so as to generate a single echo as if the receiver is located at a single point in space.

In some embodiments of the system, for example, the system is operable such that the center frequency of transmitted waveforms is substantially less than 5 MHz.

In some embodiments of the system, for example, the center frequency of the transmitted waveforms is adjustable over the bandwidth of the transducer operable to assist the said optimization of the array position and orientation by reducing the sensitivity of the optimization to the position and orientation of the array.

In some embodiments of the system, for example, the bandwidth of the transmitted waveforms is adjustable over the bandwidth of the transducer, e.g., from 10% to 100%, operable to assist the said optimization of the array position and orientation by reducing the sensitivity of the optimization to the position and orientation of the array.

In some embodiments of the system, for example, the system is operable such that a center frequency and/or bandwidth of the transmitted waveforms may be increased to improve the spatial localization of the object.

In some embodiments of the system, for example, the system is operable such that specific transmitted waveforms or types of waveforms may be transmitted to improve the spatial localization of the object, improve the signal-to-noise ratio (SNR) of echoes, and/or reject sources of interference, for example, frequency modulated waveforms, phase modulated waveforms, orthogonal frequency-division multiplexing (OFDM) waveforms, direct-sequence spread spectrum (DSSS) modulated waveforms, pseudorandom noise waveforms, pseudorandom binary sequence waveforms, maximum length sequence waveforms, binary coded waveforms, complementary waveforms, arbitrary coded sequence waveforms, range compressible waveforms, arbitrary waveforms, etc.

In some embodiments of the system, multiple different waveforms are transmitted simultaneously from different sources, for example, orthogonal waveforms, coded waveforms, and waveforms with different frequencies and/or bandwidths and/or time-bandwidth products and/or durations.

In some embodiments of the system, multiple different waveforms are transmitted from different sources at different times, for example, orthogonal waveforms, coded waveforms, and waveforms with different frequencies and/or bandwidths and/or time-bandwidth products and/or durations.

In some embodiments of the system, multiple different waveforms are transmitted from the same sources at different times, for example, orthogonal waveforms, coded waveforms, and waveforms with different frequencies and/or bandwidths and/or time-bandwidth products and/or durations.

In some embodiments of the system, for example, the object is repeatedly localized in real-time, such that movement of the object relative to the array may be visualized on the display unit.

In some embodiments of the system, for example, the position and orientation coordinates of the object produced by the object imager are communicated for use by a separate system.

In some embodiments of the system, the object imager output includes an estimate of the quality of the object detection.

In some embodiments of the system, the object imager is operable to beamform multiple objects.

In some embodiments of the system, the object imager is operable to beamform specific features of an object.

In some embodiments of the system, the object imager is operable to beamform specific features of more than one object.

In some embodiments of the system, the object imager is operable to locate multiple features of the object such that distance and angle between the features may be quantified.

In some embodiments of the system, the object imager is operable to locate features on multiple objects such that distance and angle between the features may be determined.

Additional examples of a synthetic aperture system and method for synthetic aperture acoustic imaging, which can be employed for implementing the beamformed object imaging technique in accordance with the present technology, are described in U.S. Pat. No. 9,844,359, which is incorporated by reference as part of the disclosure of this patent document for all purposes. For example, any of the example embodiments of the synthetic aperture object imaging systems and subsystems described herein, including but not limited to the systems of FIG. 1E, of FIG. 7, FIG. 8B, FIG. 8C, and/or FIG. 8D, can include and/or employ one or more features, including structural features and/or functional features, of the devices, systems and methods described in U.S. Pat. No. 9,844,359.

Further Discussion and Example Data from Example Embodiments of the Disclosed SAOI Techniques The new advantages and benefits from implementations of the disclosed synthetic aperture object imaging (SAOI) systems and methods for image formation, spatial sampling requirements, and spatial resolution are envisioned to be profound because conventional limitations in acoustic imaging do not apply to the disclosed SAOI techniques. Conventional synthetic aperture imaging utilizing regularly sampled, planar arrays is well defined. The far field spatial response of such a synthetic aperture array may be approximated as the Fourier transform of the convolution of the transmit and receive arrays. The spatial response (e.g., the response in azimuth or elevation) is typically characterized in terms of beam characteristics, e.g., main lobe width, sidelobe height, depth-of-field, Fresnel distance, etc. Apodization functions, e.g., windows, applied to either the transmit or receive apertures modify the beam characteristics. Transmitted frequency, bandwidth, and waveform shape also modify the beam shape parameters. Focusing delays applied on transmission and/or reception to such an aperture serve to bring the far field response into the near field, which also modifies the beam shape parameters. For example, the beamwidth is typically defined in proportion to wavelength times f-number, where f-number is defined as the focal distance divided by the effective aperture size (which may be larger than the physical aperture size, e.g., in the case of synthetic aperture). The element spacing of such an aperture is also critical when high degrees of focusing and beam steering are considered. The at least one-half wavelength sampling requirement, e.g., defining the array pitch, is critical when beams are both focused and steered so as to avoid grating lobes, which may also be characterized for a given array.

The disclosed SAOI systems and methods does not suffer from these or similar restrictions on array pitch because grating lobe energy is almost always incoherent for objects with finite volume, i.e., grating lobe energy is scattered elsewhere, often in unobservable directions and/or directions away from the object itself, due to the at least some convexity and finite size that any object with finite volume must have. This feature is extremely useful, for example, because it enables sparse synthetic apertures, lower channel counts, and inexpensive systems for imaging objects. Additionally, sparse apertures need not be regularly sampled, which serves to further suppress grating lobe energy in the beamforming process. Additionally, sparse apertures formed with objects modeled as irregularly-sampled surfaces serve to further suppress grating lobe energy in the beamforming process.

In conventional synthetic aperture imaging, all of the factors defining beam characteristics on both transmission and reception affect the appearance of a point scatterer in space when echoes are coherently beamformed over a spatial grid and an image is formed, e.g., the spatial response is characterized as a point spread function (PSF). The PSF may be incoherent, for example, when synthetic aperture echoes are beamformed for a point scatterer, the beamformed echoes are envelop detected, removing all phase information, and the peak value of the envelope is stored for a given location of the scatterer in space, regardless of the range of the peak or range of the scatterer. The resulting incoherent field magnitude is then mapped, e.g., over a grid of point scatter locations, to form a beam plot or beam pattern, which are often measured and/or simulated for a given array to characterize its performance.

In conventional synthetic aperture imaging, the PSF may also be coherent, for example, when synthetic aperture echoes are not beamformed, and they are left as time domain echoes. In this way, the PSF represents the spatial-temporal response of a point scatterer that may be very different for every transmitter-receiver pair because all spatial and temporal information is retained. In other words, much more information is present in the spatial-temporal response of a given aperture as compared to the beamformed and incoherently summarized beam response as described above. State of the art imaging systems utilize such coherent information to improve imaging performance in terms of resolution, speckle reduction, and contrast, e.g., through compounding multiple phase coherent wavefronts for a set of known spatial-temporal responses, which has the effect of reducing phase incoherent components (e.g., corresponding to sidelobes and grating lobes) and emphasizing phase coherent information (e.g., corresponding to the main lobe).

The disclosed SAOI systems and methods do not strictly have a PSF, except in the limiting case when the object becomes a point target, which is impossible for an object with finite volume. Consider an object approximated as a set of point scatterers (see expanded discussion below), and the PSF for each scatterer contribution is summed (assuming linear acoustics and superposition) for a given transmitter and receiver pair; the resulting quantity is no longer a PSF, instead, an object spread function (OSF) is a more appropriate term for describing the quantity. Thusly, the OSF for each transmitter/receiver pair in a synthetic aperture is the sum of PSFs for that pair for a given object. The resulting OSF for a given synthetic aperture array is therefore the collection of OSFs corresponding to all transmit-receive pairs within an aperture. One possible OSF for a given synthetic aperture can be defined as the set of all received synthetic aperture echoes each corresponding to a different transmit element, e.g., the set of synthetic transmit aperture (STA) echoes from an object is the OSF for the aperture. Another possible definition of an OSF can include all possible synthetic aperture echoes formed from one or more transmit elements and one or more receive elements. Yet another possible definition of an OSF can include all possible synthetic aperture echoes formed from all possible combinations of one or more points on an object, and all possible combinations of one or more transmit elements, and all possible combinations of one or more receive elements. The number of possible combinations is virtually limitless. This disclosed SAOI techniques provide a novel way to describe an imaging system believed to have far reaching and profound implications.

The disclosed SAOI systems and methods can utilize the spatial-temporal response from a one or more elements of an array to the object and back to one or more elements of the array, and this spatial-temporal response is the OSF. For example, the OSF depends on the shape of the object, physical properties of the object, physical properties of the medium, its orientation relative to the transmit and receive array elements, the shape, size, and geometry of the transmit and receive elements, and the diffraction and propagation of sound waves.

The object spread function (OSF) definition may be used to quantify the spatial resolution of the disclosed synthetic aperture object imaging systems and methods. Spatial resolution is a subjective characteristic of an imaging system that depends on the precise definition. One commonly used definition is the full-width half maximum (FWHM) or −6 dB magnitude width, or equivalently, the −3 dB power width. As described above, the diffraction limited spatial resolution of conventional imaging systems is proportional to f-number times wavelength. The temporal spatial resolution, e.g., as measured using the coherent PSF described above, is often defined as being proportional to transmitted pulse length (or compressed pulse length for coded waveforms), which in turn is proportional to wavelength divided by fractional bandwidth. The f-number of the disclosed SAOI system is difficult to define because the synthetic aperture is formed with object. For example, neglecting the influence of the object on the f-number (for sake of argument), if the aperture surrounds the object, then the effective f-number to points on object can be quite small, enabling very high diffraction limited spatial resolution of points on the object in the conventional sense (e.g., PSF). In this way, the disclosed SAOI systems and methods may be viewed as tomographic in nature, and tomographic systems are known to achieve high spatial resolution. Taken a step further, by considering the extension of the aperture made with the object, more of the aperture interrogates points on the object through bistatic reflections because more of the aperture is visible to each point. The resulting larger effective aperture further decreases the effective f-number, and increases the diffraction limited spatial resolution of points on the object in the conventional sense (e.g., PSF). It is not hard to see that diffraction limited resolution of points on an object in the conventional sense can be much smaller than a wavelength using a tomographic aperture.

The above can be taken an additional step further. Consider the OSF for a given object-aperture system in one orientation, and only synthetic aperture echoes are observable, e.g., the OSF for the object-aperture system is the synthetic aperture data set, defined as $OSF_0$. Now consider a second OSF measured for the same object-aperture system, but with a small 6DoF perturbation (e.g., displacement) between the object and the aperture, call it OSF(d). OSF(d) will be different than OSF(0), and how much different depends on many factors, including all aspects of the aperture and object, wavelength, bandwidth, and how the difference is quantified as a function of OSF(0) and OSF(d), e.g., linear and/or non-linear combinations of OSF(0) and OSF(d), cross-correlation, summation, etc., to quantify similarity. One definition of spatial resolution may be formulated as 2d such that $|S(OSF(0),OSF(d))|=0.5$ for perturbations d in one or more spatial dimensions, where the function S, returning a scalar value in units of echo amplitude, determines the similarity between the two sets of synthetic aperture echoes. The resulting value of 2d can be very small, relative to a wavelength, at least one-half wavelength using an aperture substantially encompassing the object, in the same way that an interferometer can resolve very small displacements.

The disclosed SAOI systems and methods may be viewed as a multipath acoustic interferometer that takes into account all possible round-trip paths from the array to the object and back to the array, which is what makes the disclosed synthetic aperture object imaging systems and methods extremely sensitive to small displacements and for localizing objects in space. The example result shown in FIG. 6 illustrates the potential sensitivity to small displacements for a non-tomographic aperture, for example.

In some implementations, for example, the object beamformer of an example embodiment of an SAOI system functions in a similar way to the function S above, e.g., the measured coherent OSF is an input (e.g., synthetic aperture echoes), a model of the array is an input (e.g., array model), the model of the object is an input, (e.g., object model), the medium is an input (e.g., sound speed, usually assumed constant), and the relative orientation of the array to the object is an input (i.e., d as above or 6DoF coordinate or 4×4 transformation matrix), and the output (e.g., object beamformed echo) as a function of d is computed in order to maximize some measure of the output (i.e., integrated object beamformed echo power). In this way, the object beamformer may be used to estimate the spatial resolution of the object imaging system. For example, given a set of synthetic aperture echoes recorded from an object in a known position (e.g., the OSF), the response of the object beamformer to displacements of the object (or array) away from the known position in one direction gives a measure of the spatial resolution (e.g., displacement required to achieve one-half maximum power) in that direction. An example of this measure of spatial resolution may be derived from the peak width of the result shown in FIG. 6, which is approximately one-half wavelength for the simulated problem (again, which is not a tomographic aperture).

In the aforementioned discussions and descriptions with regards to the object beamformer, a clear case has been made that the object beamformer attempts to match synthetic aperture observations with a model of the problem. Without loss of generality and for example, this is only one possible formulation of the object detection and locating problem using a synthetic aperture, and other formulations are possible, for example, within the framework of maximum likelihood estimation theory or other estimation and/or detection theories. However, the foundations, principles, and goals of alternative formulations are still the same, and such formulations cannot escape the novel concept of a synthetic aperture formed with an object as a means to detect and localize said object.

The acoustic transmit/receive response of an object may be simulated by approximating the object and the array of transducer elements, e.g., representing the object and array as collections of point targets, point sources, and point receivers. In this way, the object is spatially sampled. Ideally, the spatial samples of the object and array are infinitesimally small so as to generate the best approximation. Computational considerations require that the spatial samples be finite, and approximately on the order of one wavelength based on simulations and experiments, but an exact requirement is hard to define for a given object and array geometry. In some example implementations, numerical integration of the Rayleigh-Sommerfeld integral can be made to converge accurately in the nearfield of an aperture (e.g., using a fast-nearfield method) or the spatial impulse response method may be applied to compute a spatial impulse response of the object, which can then be convolved with the time domain transmit/receive response. Likewise, when beamforming the object, a similar spatial sampling requirement of the object applies, e.g., the spatial sampling requirement to accurately simulate echoes from the object is also required to object beamform echoes from the object. Thus, the spatial sampling requirements for the disclosed SAOI systems and methods are loosely defined as (i) achieving an adequate number of spatial samples to determine one or more unknown parameters describing the array, the object, and their relation, i.e., at least as many independent measurements as there are unknowns are required, and (ii) for assuring adequate spatial sampling of the object itself in order to approximate an analog scattering process with a discretized and computationally feasible scattering process, e.g., in accordance with established numerical methods for approximating the transmit/receive response of an object.

Example implementations including proof-of-concept experiments were performed demonstrating certain aspects, features, and capabilities of the disclosed SAOI method. In the examples described below, an example implementation of the SAOI method was used for locating two different objects in a three-dimensional space, the first with three degrees of freedom and the second with six degrees of freedom, which was performed using commercial ultrasound imaging hardware and an off-the-shelf computing platform. The hardware used in the example implementations included a Verasonics Vantage 256 research ultrasound system (Verasonics, Inc., Kirkland, Wash.) interfaced to a Vermon 3 MHz 32×32 matrix array probe (Verasonics, Inc., Kirkland, Wash.) using the Verasonics UTA 1024-MUX adapter (Verasonics, Inc., Kirkland, Wash.), 1 UR10 robot arm (Universal Robots A/S, Odense, Denmark), and a Dell Precision Tower 7920 workstation (Dell, Inc., Round Rock, Tex.) containing a NVIDIA Quadro P620 GPU (NVIDIA Corp., Santa Clara, Calif.).

The robot arm was programmed to manipulate the object within a 50-gallon water tank filled with temperature-monitored distilled water. Acoustic energy was coupled through a thin TPX plastic acoustic window on the side of the tank and directed at the object. The probe was held stationary against the acoustic window using a custom holder. Aquasonic 100 coupling gel (Parker Laboratories, Inc, Fairfield, N.Y.) was applied to the probe to provide acoustic coupling into the TPX window. Software was written in MATLAB vR2019b (MathWorks, Inc., Natick, Mass.), Microsoft Visual Studio Community 2019 (Microsoft Corp., Redmond, Wash.), and CUDA v10.1 GPU (NVIDIA Corp., Santa Clara, Calif.) and executed in a Windows 10 operating system (Microsoft Corp., Redmond, Wash.) environment to coordinate data acquisition and processing.

The matrix array probe includes a nominally 3 MHz center frequency, nominally 50% fractional bandwidth 32×32 array of elements (e.g., 1024 total elements) addressable in four sub-arrays of 8×32 elements (e.g., 4 sub-arrays of 256 elements). The element pitch of the array is 0.3 mm×0.3 mm (e.g., 0.6 wavelength at c=1500 m/s, thus approximately a phased array), with three inactive rows in elevation, making the array aperture size 10.5 mm in elevation and 9.6 mm in azimuth.

Figure 9:
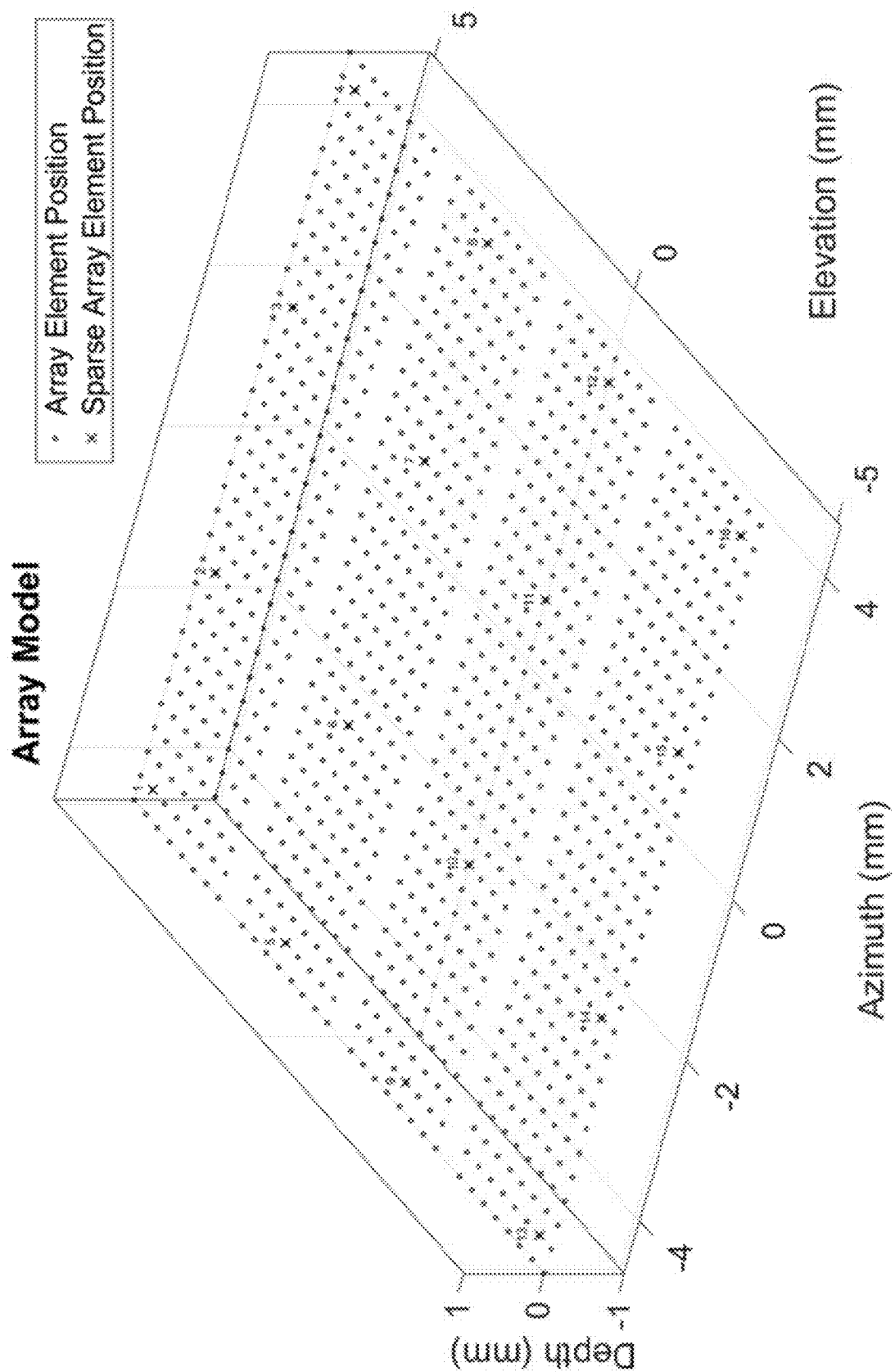
FIG. 9 shows a diagram depicting an example full array geometry and a 4×4 sparse array geometry used in an example object beamformer, in accordance with the present technology.

The ultrasound system was programmed to transmit wideband single cycle pulses at 30 Volts peak-to-peak on 16 elements with elements arranged sparsely on a 4×4 grid within the 32×32 grid as shown in FIG. 9, with the element positions plotted with an "o" and the spare aperture positions plotted with an "x" and also numbered from 1 to 16.

FIG. 9 shows a diagram depicting an example full array geometry and a 4×4 sparse array geometry used in an example object beamformer.

Echoes were received on 256 elements at a time per transmission, which required 4 transmissions per transmit element to cover reception on all 1024 receive elements. The 4-to-1 multiplexing was enabled UTA 1024-MUX adaptor that interfaces all 1024 elements to 256 transmit/receive channels on the ultrasound system. In total, 64 transmissions were required to form a full synthetic transmit (STA) aperture with the 16-element sparse aperture, at a pulse-repetition-frequency (PRF) of 6.41 kHz.

Received echoes were bandlimited to 5 MHz prior to 14-bit ADC sampling at 35.7143 MHz, FIR filtered with a 23-tap lowpass filter (−3 dB point at 4.885 MHz), decimated by a factor of 3 to 11.9048 MHz, and FIR filtered again with a 41-tap bandpass filter (−3 dB points at 1.488 MHz and 4.464 MHz) prior to storage as a 2D array of 1024 16-bit signed integer samples by 256 echoes comprising full STA for the 4×4 sparse aperture. Only received echoes corresponding to the transmit elements were retained for processing, resulting in 256 total echoes per complete STA acquisition.

Redundant reciprocal echoes were directly summed (as discussed above) in order to reduce the amount of data and processing, which resulted in a 2D array of 1024 signed integer samples by 136 echoes comprising the full unique STA dataset for the 4×4 sparse aperture. Prior to beamforming, the echoes were converted to floating point and up sampled by a factor of 3 to restore the original sample rate of 35.7143 MHz.

Two objects were investigated: (i) a 6.35 mm diameter steel sphere, and (ii) a complex object that includes eight 6.35 mm diameter steel spheres arranged on a spiral approximately 5 cm in diameter. The complex object was comprised of multiple spheres due to the availability of only one ultrasound probe for testing. Multiple spheres effectively simulate using multiple probes directed from multiple vantage points around a different object, e.g., looking out the face of the probe, eight independent spheres are observable as if eight probes surrounding a different type of object observe eight independent locations on the object from eight different directions. Both objects were constructed by 3D printing a plastic structure with posts topped with 6.35 mm diameter cups to receive nominally 6.35 mm diameter steel bearings glued in place with marine epoxy.

Figure 10:
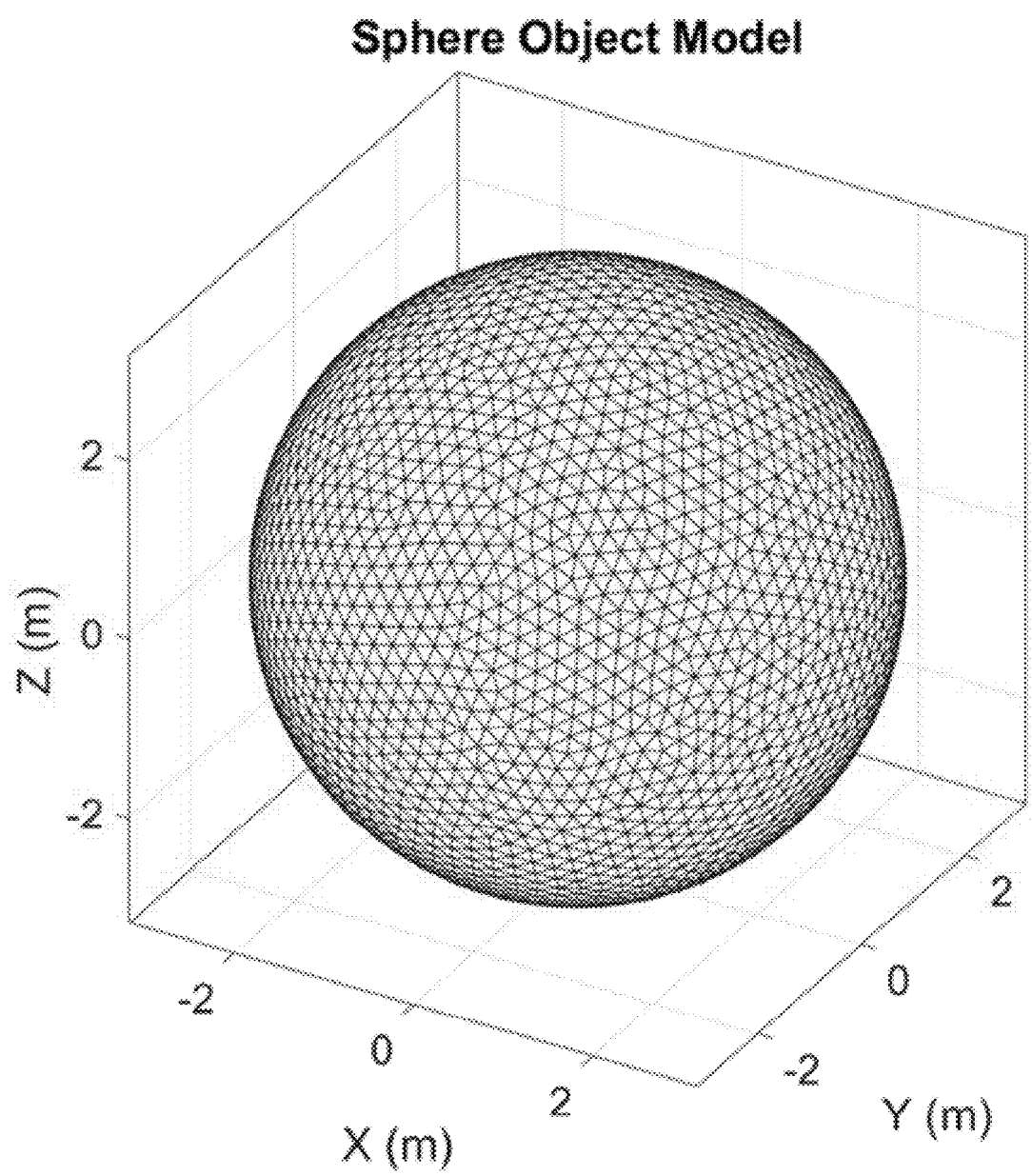
FIG. 10 shows a diagram illustrating a sphere object model used in an example object beamformer, like that discussed in connection with FIG. 9.
Figure 11:
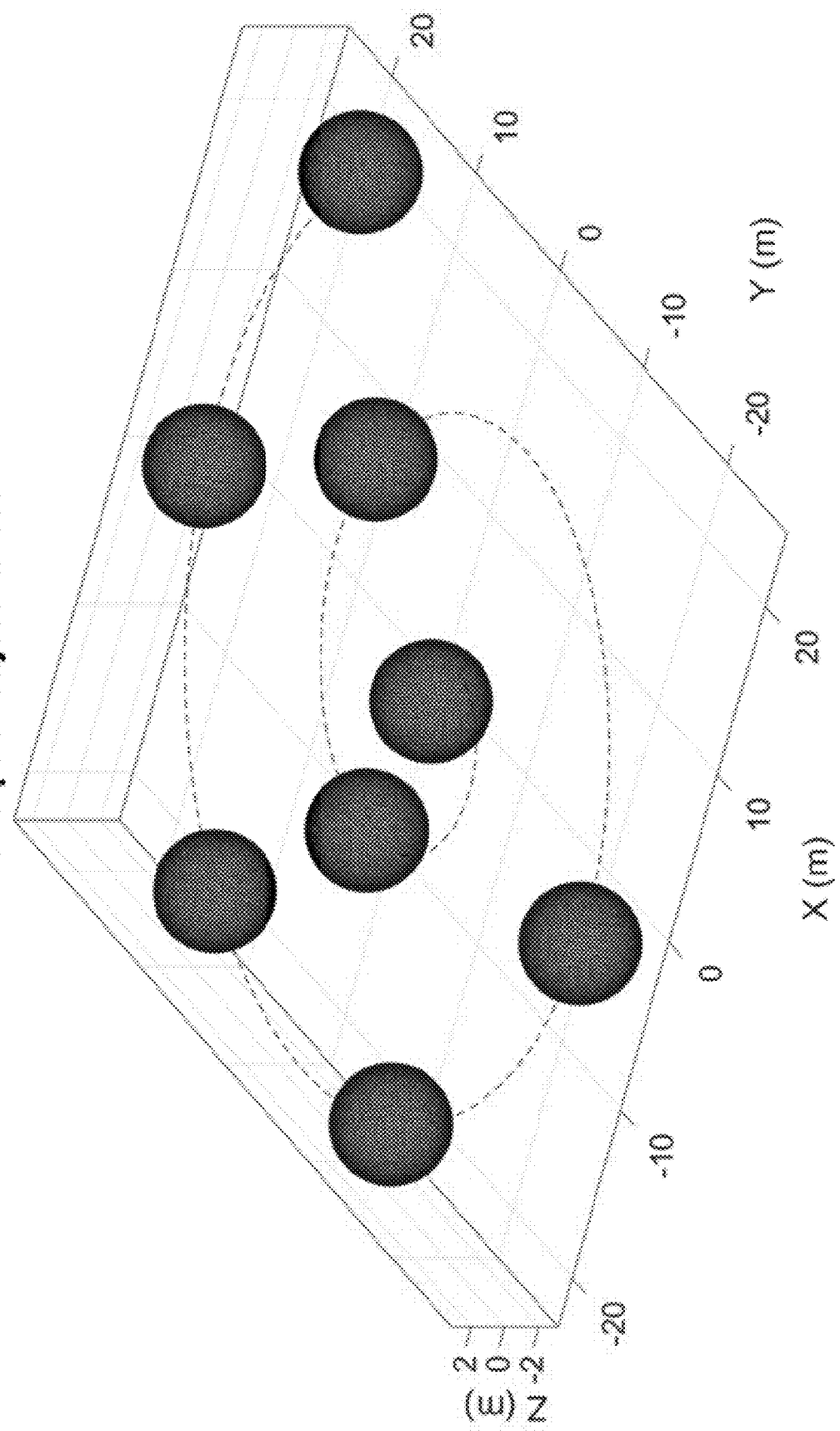
FIG. 11 shows a diagram illustrating a complex object model used in an example object beamformer, like that discussed in connection with FIG. 9.

The sphere object was modeled as a triangulated surface comprised of 5,804 triangles 2,904 and vertices as shown in FIG. 10. The mean edge length of the triangles is 0.2148 mm (standard deviation 0.0226 mm), which is less than the one-half wavelength value of approximately 0.25 mm. The triangles are approximately equilateral. Likewise, the complex object is modeled as eight spheres modeled using 23,232 vertices and 46,432 triangles as shown in FIG. 11. The objects were stored on the GPU in arrays containing the vertex points, vertex normals averaged from adjacent faces, and normalized effective vertex areas averaged from adjacent faces. Additionally, the 4×4 sparse array element positions modified by a 4×4 transformation matrix were also stored on the GPU.

FIG. 10 shows a diagram illustrating a sphere object model used in the example object beamformer.

FIG. 11 shows a diagram illustrating a complex object model used in the example object beamformer.

The objects were mechanically fastened to the robot arm and lowered into the tank. The effective center position of each object as determined by the coordinate system of each's object model was programmed to be at the origin in the robot tool frame-of-reference. For example, the center position of the sphere object model is at (x,y,z) coordinate (0,0,0), thus, an appropriate offset was added to the robot's end effector position to center the tool center position at the center of the sphere. The coordinates of the robot tool position were recorded along with RF ultrasound echoes for 100 randomly selected independent positions of the object, e.g., 100 random XYZ positions of the sphere object and 100 random 6DoF positions (e.g., XYZ and three Euler angles) of the complex object. For the complex object, the randomly generated EAX and EAY angles were set to the same value as an additional check of consistency. Due to the nature of the control system within the robot, both a commanded position and an actual position are generated. The actual position is a function of position encoders on each of 6 joints on the robot arm, and thus, is a measurement of the object's position in space. It is the robot actual position that is used as the measured position in the trials, which may be slightly different than the commanded position depending on many factors beyond the scope of this demonstration.

Figure 12A:
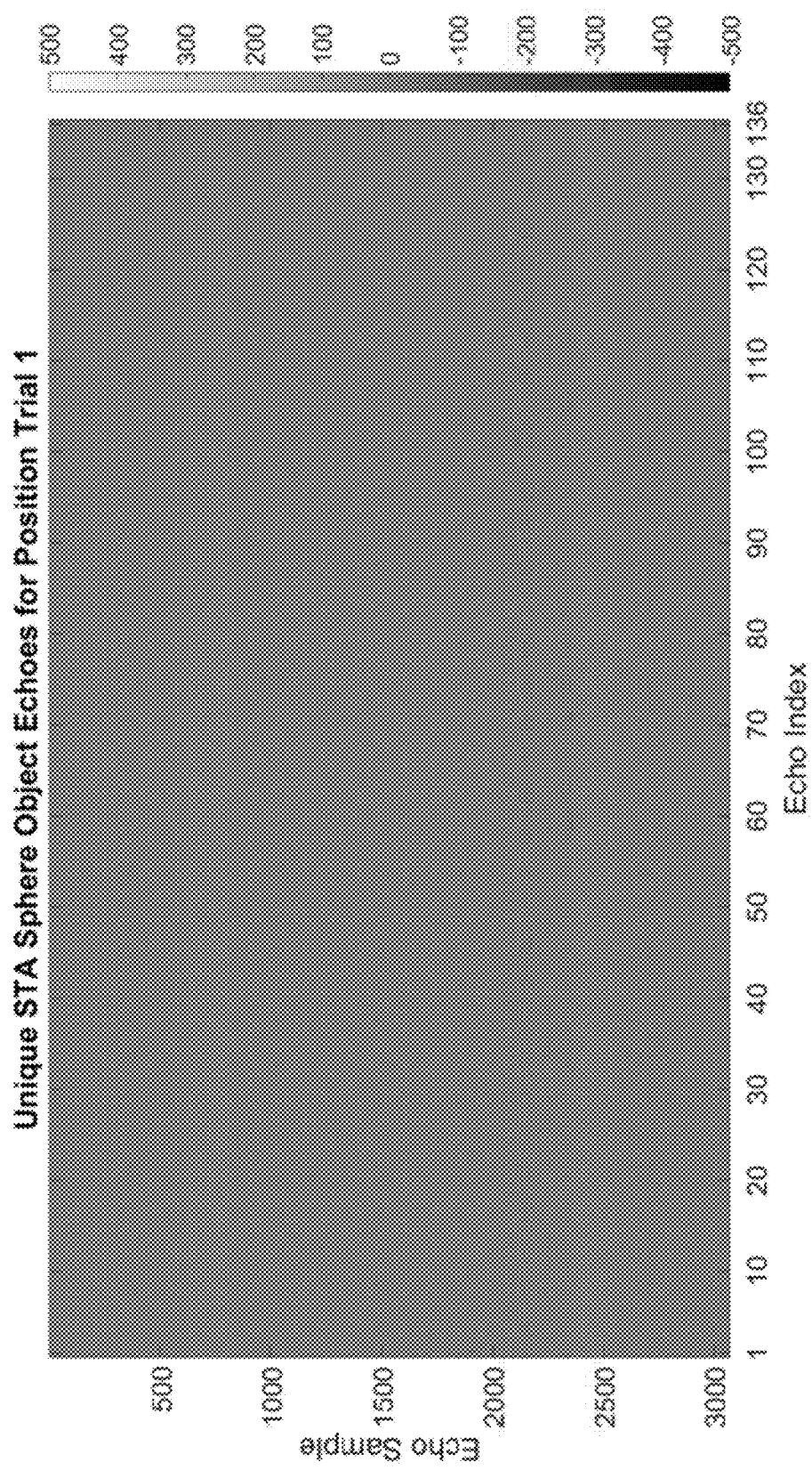
FIG. 12A shows a data plot depicting example sphere object unique STA RF echoes.
Figure 12B:
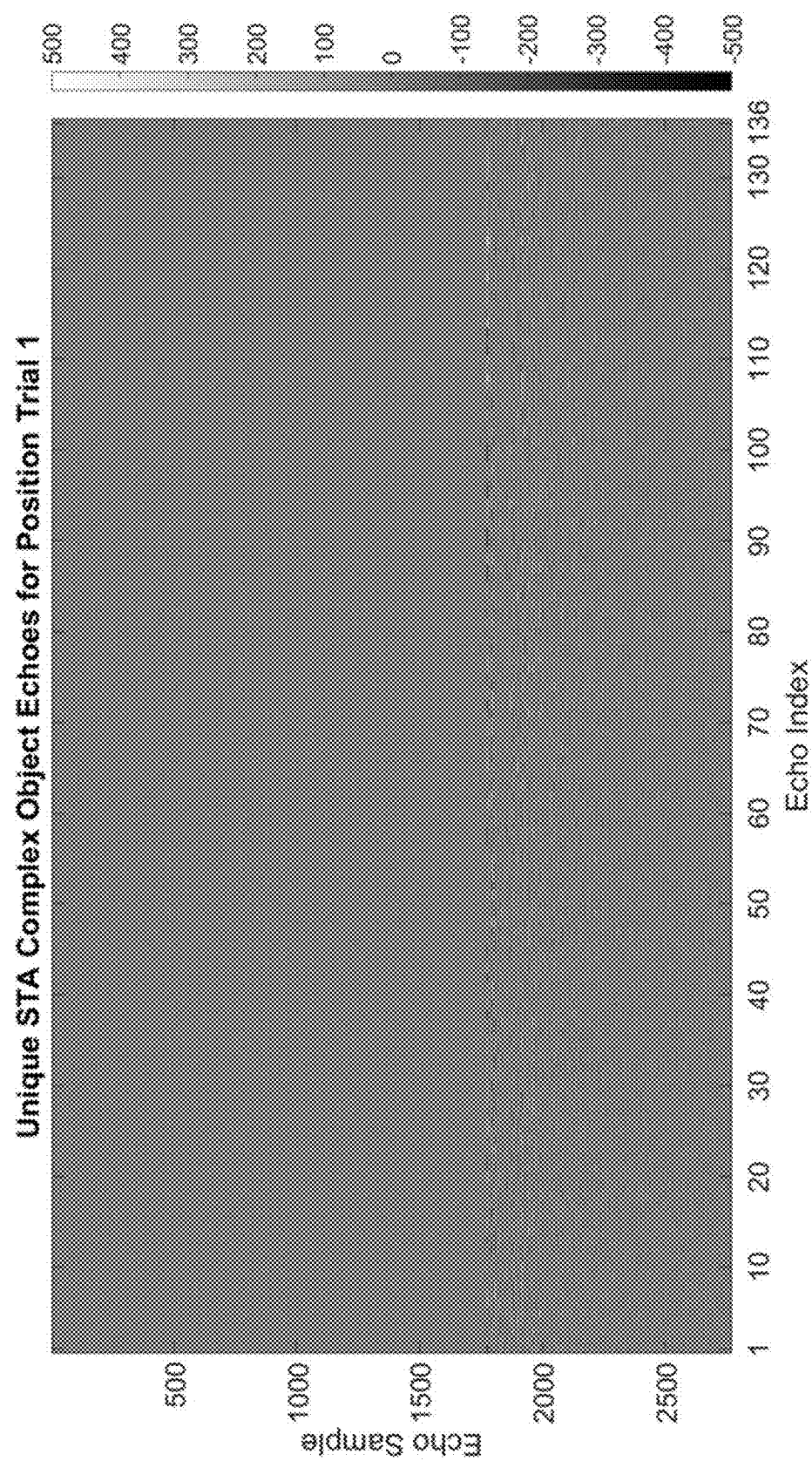
FIG. 12B shows a data plot depicting example complex object unique STA RF echoes.

FIGS. 12A and 12B show example full unique STA RF echoes for the 4×4 sparse array recorded for the sphere and eight sphere complex object, respectively. For the purposes of display, the monostatic echoes were summed twice to maintain similar amplitude with the twice summed bistatic echoes, the first 300 samples were blanked out to omit transmit pulse interference, resulting in arrays of size 3072 samples×136 echoes as shown (e.g., 35.7143 MHz sample rate). The grayscale indicates the amplitude of the echoes ranging from −500 to 500 in scaled ADC units (e.g., the maximum range for unit receive apodization is −16384 to +16382). In FIG. 12(a), the echoes from the surface of the steel sphere are observed around sample range 2100-2160, which correspond to a depth range of 43.8-45.1 mm for the estimated sound speed of 1491 m/s at 22.75° C. tank temperature. Likewise, in FIG. 12(b), the echoes from the surface of the complex object are observed starting around sample range 1740, which corresponds to a depth of 36.1 mm for the estimated sound speed of 1482 m/s at 20.0° C. tank temperature. Note how much more complex the echoes are for the complex object compared with the sphere object.

Using the object model, the array model, and the RF echoes in an object beamformer function coded for the GPU, an objective function was formulated based on the integrated object beamformed echo power over a time window spanning 23 samples at 35.7143 MHz, e.g., −0.308 to 0.308 microsecond in increments of 0.028 microsecond, resulting in a scalar value. Within the object beamformer, parameters affecting the output include a specular exponent value of 4 (e.g., p=4), a transmit directivity exponent of 1 (e.g., qt=1), and a receive directivity exponent value of 1 (e.g., qr=1). For each trial position of the object, the position of the object was solved for using a Monte-Carlo optimizer, e.g., XYZ position for the sphere, and 6 DoF position comprised of XYZ and three Euler angles for the complex object. The least root mean square error (LRMSE) transformation relating the measured robot tool position in the robot frame-of-reference to the SAOI estimated position in the array frame-of-reference was estimated using the well-known Kabsch algorithm, and the coordinates of the object and robot are reported in the array frame-of-reference for ease of interpretation.

Figure 13:
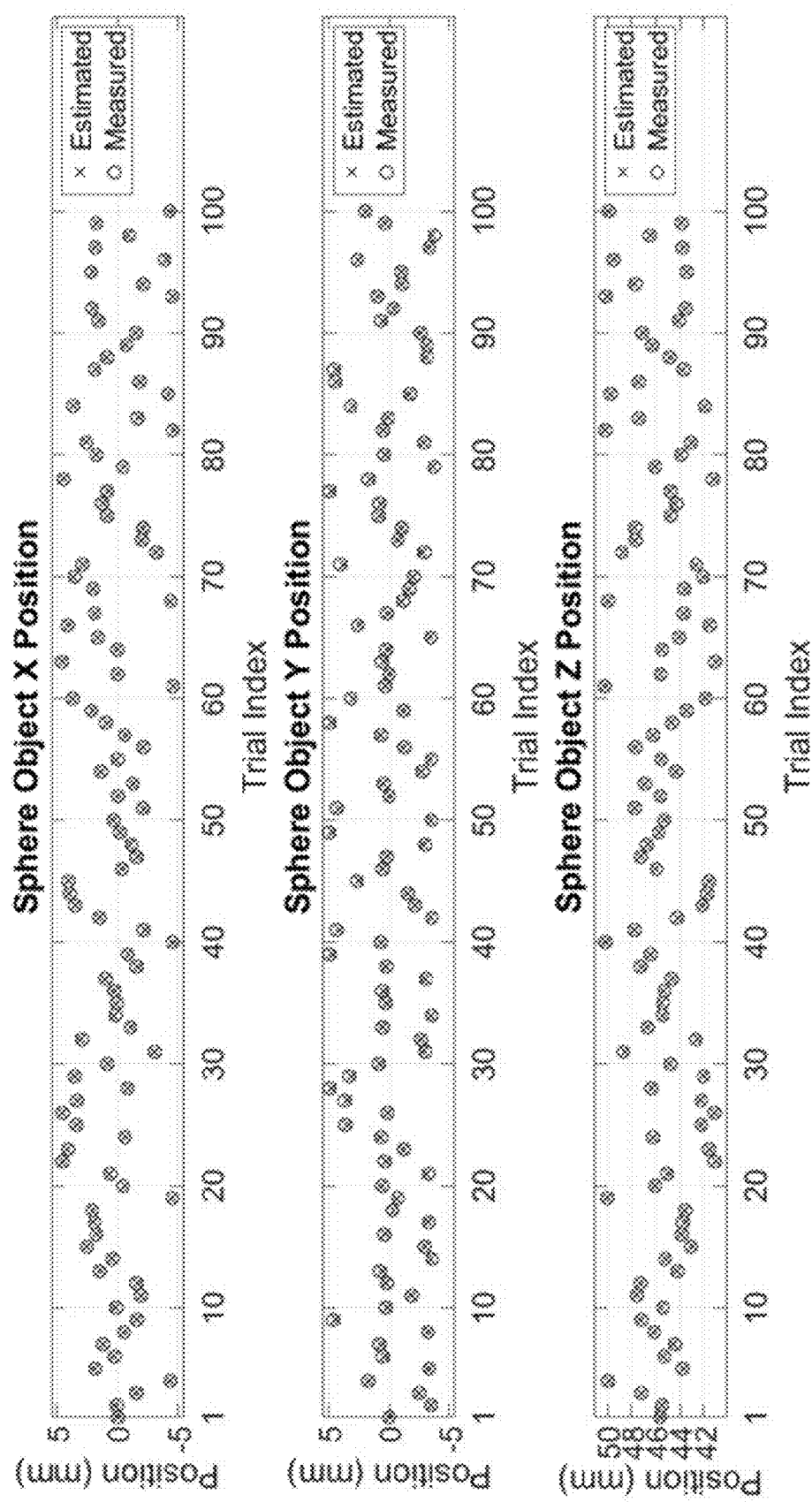
FIG. 13 shows plots depicting example sphere object SAOI estimated and robot measured X, Y, and Z positions for 100 trials.

FIG. 13 shows the example results for 100 position trials of the sphere object, with SAOI estimated positions plotted as "x" and robot positions plotted as "o". Note the tested range of approximately ±5 mm in each dimension from the first trial. A statistical analysis of the errors for the complex object is presented in Table 1. Note the positional errors are approximately zero mean, and the RMS values are substantially less than the wavelength value of 0.494 mm at the sound speed during data collection. The RMS error of the estimated transformation relating the robot frame-of-reference to the array frame-of-reference is 0.16 mm. Note that the robot coordinates are internally referenced to the coordinate system at the base of the robot, which was over 1 meter away from the tool center position of the object in the tank. Very careful measurements using a reference measurement device (e.g., a FaroArm) might determine that the robot could be a significant source of error since it has a claimed positional repeatability of ±0.1 mm.

TABLE 1

Error analysis for 100 positions of the sphere object.

| Coordinate | RMS error | Mean error | Median Error |
|---|---|---|---|
| X | 0.072 mm | −0.001 mm | 0.009 mm |
| Y | 0.126 mm | 0.020 mm | −0.001 mm |
| Z | 0.070 mm | −0.006 mm | −0.011 mm |

Figure 14A:
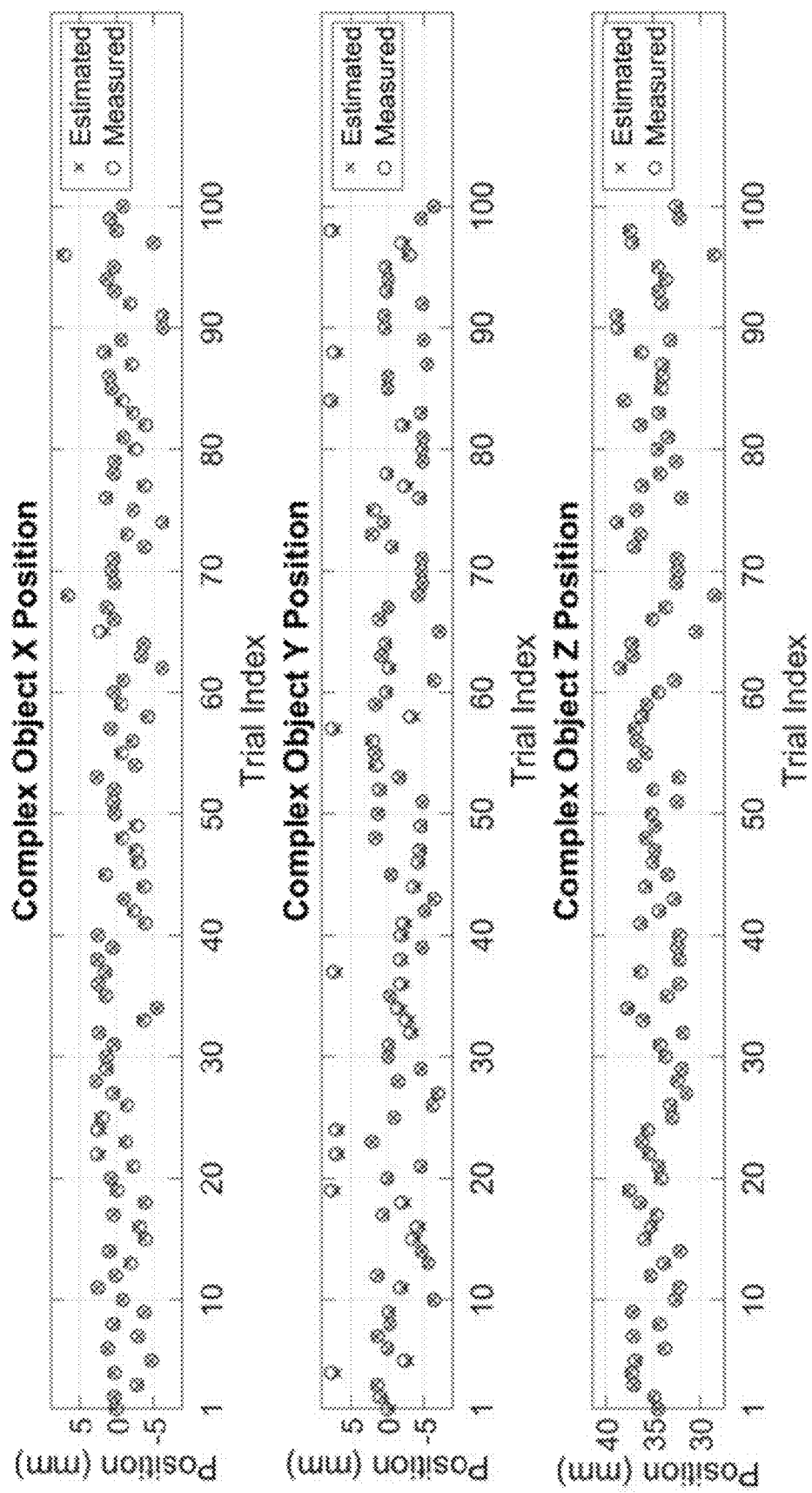
FIG. 14A shows plots depicting example complex object SAOI estimated and robot measured X, Y, and Z positions for 100 trials.
Figure 14B:
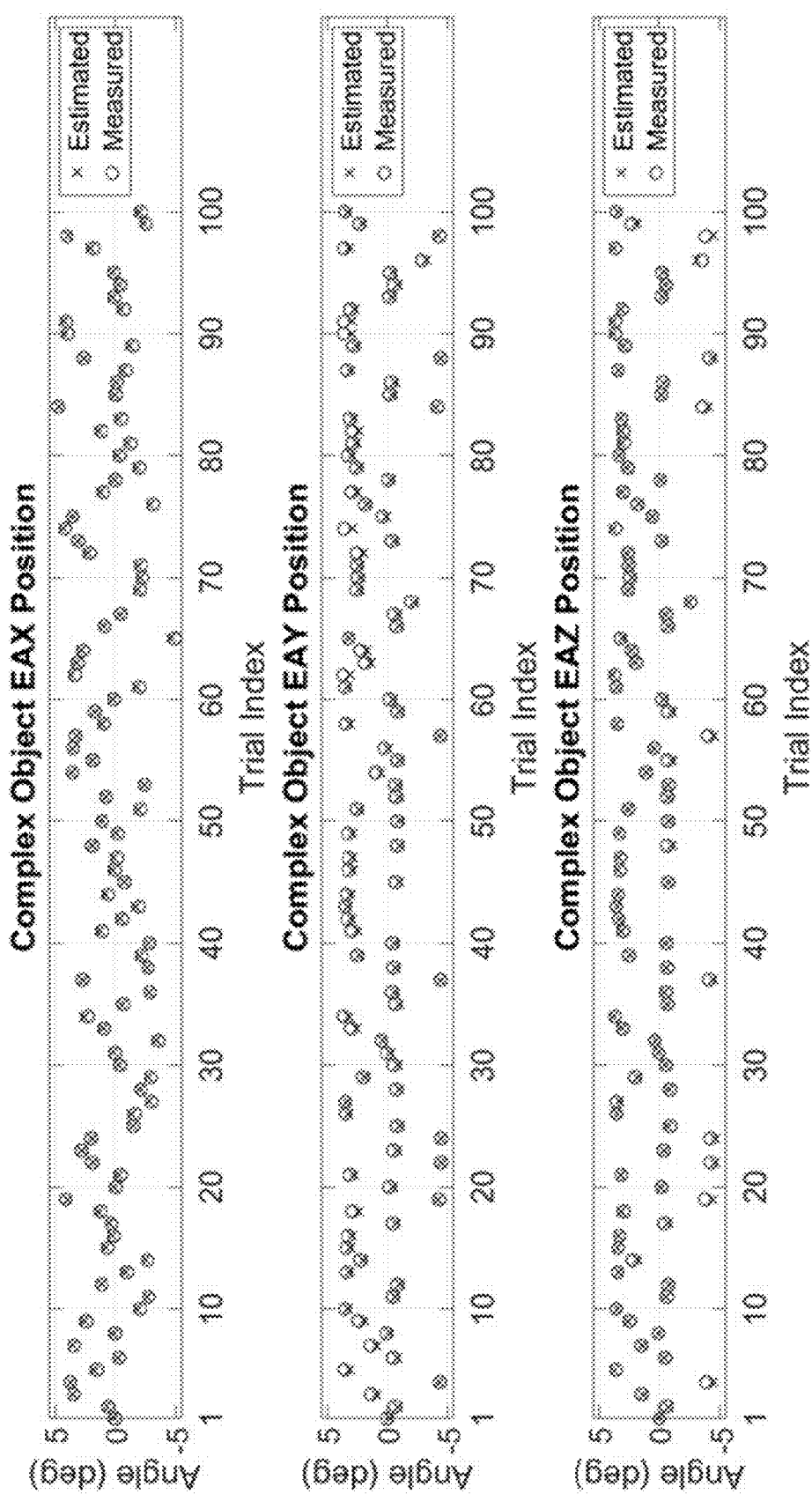
FIG. 14B shows plots depicting example complex object SAOI estimated and robot measured EAX, EAY, and EAZ angles for 100 trials.

The example results for the 100 position trials of the complex object are shown in FIG. 14(a) for XYZ positions and FIG. 14(b) for Euler angles EAX, EAY, and EAZ, with SAOI positions plotted as "x" and robot positions plotted as "o". Note the tested range of approximately ±8 mm and ±5 degrees in each dimension from the first trial. A statistical analysis of the errors for the complex object is presented in Table 2.

To check the consistency of the robot measurements and the SAOI estimated position across two degrees-of-freedom, for example, the EAY and EAZ coordinates, set to be equal in the trials, were compared for the robot and for the estimated positions. In other words, the RMS error between EAY and EAZ was compared for the robot and for the SAOI measured positions, and the results are summarized in Table 3. Note that the RMS error of the robot accounts for approximately 60% of the SAOI error, at least for EAY and EAZ.

TABLE 2

Error analysis for 100 positions of the complex object

| Coordinate | RMS error | Mean error | Median Error |
|---|---|---|---|
| X | 0.279 mm | 0.094 mm | 0.088 mm |
| Y | 0.306 mm | −0.221 mm | −0.189 mm |
| Z | 0.192 mm | 0.007 mm | −0.008 mm |

TABLE 2-continued

Error analysis for 100 positions of the complex object

| Coordinate | RMS error | Mean error | Median Error |
|---|---|---|---|
| EAX | 0.101 deg | 0.138 deg | 0.138 deg |
| EAY | 0.162 deg | −0.290 deg | −0.284 deg |
| EAZ | 0.204 deg | −0.043 deg | −0.023 deg |

For this example implementation, the errors, though more significant than for the single sphere object, are reasonable considering the significantly greater complexity of solving for six unknown degrees-of-freedom. A number of factors may have contributed to the errors, including but not limited to: error in defining the tool center position of the complex object, repeatability error of the robot, superposition of multiple echoes, existence of many nearby local maxima in the 6DoF parameter space, and inaccuracies of the sphere placement within the complex object. Nonetheless, the complex object spanning nearly 50 mm in size, was successfully located at a distance of approximately 35 mm for a wide range of positions and angles. The example result is particularly impressive considering the relatively small 4×4 sparse aperture comprised of only 16 elements and spanning less than 10 mm×10 mm. Modifications in the implementation of the example SAOI method may be used to improve the performance.

TABLE 3

Consistency analysis for EAY and EAZ for both the measured robot and SAOI estimated positions

| Coordinate | Robot RMS error | SAOI RMS error |
|---|---|---|
| EAY-EAZ | 0.168 deg | 0.273 deg |

EXAMPLES

In some embodiments in accordance with the present technology (example A1), a tomographic synthetic aperture acoustic imaging system includes an array of transducer elements operable to transmit, receive, and/or transmit and receive acoustic signals at an object that forms a synthetic aperture of the acoustic imaging system with the object, wherein the acoustic signals include transmitted acoustic signals and received acoustic echoes returned from the object; an object beamformer unit comprising one or more processors and one or more memories and configured to (i) beamform the object coherently for one or more regions of the object as a function of position, orientation, and/or geometry of the array of transducer elements with respect to a model of the object (e.g., where the model of the object comprises information representative of a surface of the object), and (ii) produce one or more beamformed output signals in digital format that includes spatial information about the one or more regions of the object derived from beamforming the acoustic echoes; a data processing unit, comprising a processor and a memory, in communication with the object beamformer unit and the array of transducer elements, and configured (i) to process the one or more beamformed output signals to produce at least one scalar output associated with the one or more beamformed output signals, (ii) to process the at least one scalar output to produce optimized parameters associated with the array of transducer elements and/or the model of the object, (iii) to instruct the object beamformer to re-beamform the object with updated optimized parameters associated with the array of transducer elements and/or the model of the object producing an updated one or more beamformed output signals, and (iv) to detect the object by (a) comparing the at least one scalar output to a threshold value, (b) comparing a differential change in the at least one scalar output to a threshold value, and/or (c) comparing at least one of the optimized parameters and/or a differential change in the at least one of the optimized parameters to a threshold value; and a display unit operable to produce an image of the object based on a rendition of the position, the orientation, the geometry, and/or the surface properties of the object, relative to the coordinate system of the array, as determined by the data processing unit.

Example A2 includes the system of any of examples A1-A31, comprising transmitter and receiver circuitry coupled to the array of transducer elements and configured to (i) produce and/or process transmit acoustic waveforms as digital signals to be transduced and transmitted as the one or more acoustic waveforms by one or more selected transmit transducer elements of the array, and (ii) convert the acoustic echoes that are received at one or more selected receive transducer elements of the array into digital signals representative of acoustic return echo waveforms.

Example A3 includes the system of any of examples A1-A31, wherein the at least one scalar output produced by the data processing unit includes a quantitative value of a beamformed echo derived from one or more of integrated power, peak power, peak amplitude, peak magnitude, root-mean-squared amplitude, root-mean-squared magnitude, mean-amplitude, mean-magnitude, peak-to-peak amplitude, peak auto-correlation magnitude, peak auto-correlation amplitude, spectral bandwidth, or spectral center frequency.

Example A4 includes the system of any of examples A1-A31, wherein at least one scalar output produced by the data processing unit includes a quantitative value of a beamformed echo derived by (i) matching the received acoustic echoes returned from the object to a stored echo using one or more of mean absolute difference, mean Euclidean distance, mean edit distance, peak cross-correlation magnitude, or peak cross-correlation amplitude, peak convolution magnitude, peak convolution amplitude, peak coherence, and peak magnitude-squared coherence; wherein the stored echo is derived from one or more of a calibrated beamformed echo from the object, a measured echo from the object, a measured transmit impulse response, a measured receive impulse response, the transmit/receive impulse response, the system impulse response, the transmitted waveform, the transmitted waveform convolved with itself, a filtered transmitted waveform, an analytic transmitted waveform, a windowed transmitted waveform, a demodulated transmitted waveform, a mathematically-defined transmitted waveform, or a mathematically-defined system impulse response.

Example A5 includes the system of any of examples A1-A31, wherein the data processing unit is configured to detect the object by comparing the at least one scalar output to the threshold value and based on a convergence of one or more optimized parameters to satisfy one or more threshold values.

Example A6 includes the system of any of examples A1-A31, wherein the object beamformer unit is configured to (i) compute delays and weights based on the geometry of the array of transducer elements and the model of the object, and (ii) generate digital signals corresponding to the produced one or more beamformed output signals that are derived from beamforming the acoustic echoes according to computed delays and weights.

Example A7 includes the system of any of examples A1-A31, wherein the data processing unit or the object beamformer unit is configured to generate an optimization including two or more iterations to produce two or more of one scalar output corresponding to two or more beamformed echoes of the object corresponding to two or more sets of parameters describing the array and/or the object such that a more optimal of two or more of one scalar output may be chosen.

Example A8 includes the system of example A7 and/or any of examples A1-A31, wherein the object is detected when the optimization produces an insignificant change, below a threshold value, in the two or more of one scalar output corresponding to two or more re-beamformed echoes of the object corresponding to two or more sets of parameters describing the array and/or the object.

Example A9 includes the system of example A7 and/or any of examples A1-A31, wherein the object is detected when the optimization produces an insignificant change, below a threshold value, in the two or more sets of parameters and/or a function of two or more sets of parameters describing the array and/or the object corresponding to two or more re-beamformed echoes of the object.

Example A10 includes the system of example A9 and/or any of examples A1-A31, wherein the function applied to of two or more sets of parameters includes one or more of Euclidean norm, Manhattan norm, p-norm, maximum norm, composite norm, asymmetric norm, and Mahalanobis distance.

Example A11 includes the system of example A9 and/or any of examples A1-A31, wherein a same function is applied to two or more sets of parameters producing two or more scalar quantities representing two or more sets of parameters.

Example A12 includes the system of any of examples A1-A31, wherein the object beamformer uses the same set of synthetic aperture echoes to re-beamform the object.

Example A13 includes the system of any of examples A1-A31, wherein the object beamformer uses a partially-updated set of synthetic aperture echoes to re-beamform the object.

Example A14 includes the system of any of examples A1-A31, wherein the object beamformer used a fully-updated set of synthetic aperture echoes to re-beamform the object.

Example A15 includes the system of any of examples A1-A31, wherein the object beamformer unit is configured to store the model of the object.

Example A16 includes the system of any of examples A1-A31, wherein the object beamformer unit is configured to generate the model of the object and/or modify the model of the object.

Example A17 includes the system of any of examples A1-A31, wherein the object beamformer unit is configured to store the geometry of the array of transducer elements.

Example A18 includes the system of any of examples A1-A31, where the object beamformer unit is configured to generate the geometry of the array of transducer elements and/or modify the geometry.

Example A19 includes the system of any of examples A1-A31, wherein the display unit includes a display screen and configured to is configured to a present a visual display the object on a display screen, where the rendition of the object is made useful in the frame of reference of the array of transducer elements or in an external frame of reference, such that the visual display of the object is operable to update and visualize relative movement between the object and the array of transducer elements.

Example A20 includes the system of any of examples A1-A31, wherein the object beamformer unit is configured to (i) compute delays determined from each transmitter position to points on the model of the object and back to each receiver position; (ii) compute weights for one or more of specular scattering, acoustic field directivity, and complex reflectivity according to vectors of incidence, vectors of reflection, vectors of reception, transducer normal vectors, object face normal vectors, and/or a priori information about the object relating to the complex reflectivity; and (iii) apply the computed delays and the computed weights to stored echoes prior to summing delayed and weighted echoes to produce a single beamformed echo.

Example A21 includes the system of any of examples A1-A31, wherein the data processing unit is configured to integrate beamformed echo power over a time window, and to optimize a transformation applied to transducer element positions and normal vectors as inputs to the beamformer in order to maximize the integrated beamformer echo power over the time window.

Example A22 includes the system of any of examples A1-A31, wherein the display unit is configured to visualize the object in the frame-of-reference of the array according to the inverse of the optimized transformation.

Example A23 includes the system of any of examples A1-A31, wherein the array of transducer elements includes one or more transmitter transducer elements and one or more receiver transducer elements that are spatially-separated to an object.

Example A24 includes the system of example A23 and/or any of examples A1-A31, wherein the one or more transmitter transducer elements and the one or more receiver transducer elements are fully or at least partially surrounding the object.

Example A25 includes the system of any of examples A1-A31, wherein the array of transducer elements includes at least three transducer elements configured to create at least three reflection samples including monostatic reflection samples and bistatic reflection samples of the object, such that the reflection samples are significantly separated on a surface of the object.

Example A26 includes the system of any of examples A1-A31, wherein the array of transducer elements includes at least three transducer elements configured to create at least three monostatic reflection samples and at least three bistatic reflection samples of the object, such that the reflection samples are significantly separated on a surface of the object.

Example A27 includes the system of any of examples A1-A31, wherein the model of the object includes a plurality of vertices and a plurality of faces approximating the object with faces no larger than one acoustic wavelength resolution.

Example A28 includes the system of example A27 and/or any of examples A1-A31, wherein the faces are one-half acoustic wavelength resolution or less.

Example A29 includes the system of any of examples A1-A31, wherein the model of the object includes a plurality of points and a plurality of surface normal vectors corresponding to each point that approximate the object within at least one-wavelength acoustic resolution.

Example A30 includes the system of example A29 and/or any of examples A1-A31, wherein the plurality of points and the plurality of surface normal vectors corresponding to each point approximate the object within less than one-half acoustic wavelength resolution.

Example A31 includes the system of any of examples A1-A30, wherein the one or more acoustic waveforms include one or more composite waveforms that comprise two or more individual coded waveforms.

In some embodiments in accordance with the present technology (example A32), a method for tomographic synthetic aperture acoustic imaging includes transmitting and receiving acoustic signals, by transducer elements of a transducer array, at and from an object by forming a synthetic aperture based on transmitting of transduced acoustic waveforms at the object and receiving returned acoustic echoes from the object; beamforming the object by coherently summing delayed and weighted echo samples of the received returned acoustic echoes that returned from one or more regions of the object to produce one or more beamformed output signals, wherein the one or more beamformed output signals are functions of one or more inputs for the beamforming; generating one or more scalar outputs that are based on the one or more beamformed output signals; optimizing the one or more scalar outputs as a function of at least some of a position, an orientation, a geometric property, or a surface property of the object; detecting the object by determining a degree of optimization of one or more objective functions based on values of or changes in inputs and outputs of an optimization, using an optimizer, compared to detection criteria; and producing an image of the object based on a rendition of the position, orientation, and geometry properties and/or surface properties of the object.

Example A33 includes the method of any of examples A32-A39, wherein beamforming the object includes computing delays and weights corresponding to one or more regions of the object as a function of at least some of a position, an orientation, and a geometry of the array of transducer elements with respect to the model of the object.

Example A34 includes the method of any of examples A32-A39, wherein the one or more scalar outputs are optimized as a function of at least some of a position, an orientation, or a geometry of the array of transducer elements.

Example A35 includes the method of any of examples A32-A39, wherein the produced one or more beamformed output signals includes spatial information about the one or more regions of the object derived from coherently summing delayed and weighted echo samples from one or more regions of the object.

Example A36 includes the method of any of examples A32-A39, wherein the determining the at least some of the position, the orientation, the geometry, or the surface properties of the object includes: producing at least one scalar output associated with the one or more beamformed output signals, and processing the at least one scalar output to produce a set of optimized parameters that define the array of transducer elements and/or define the model of the object.

Example A37 includes the method of any of examples A32-A39, comprising generating delayed echo samples and weighting factors of echo samples corresponding to transmitter positions and receiver positions of the transducer array, points of a model of the object, attributes of the transducer array, and attributes of the model of the object, wherein the generated delayed echo samples and weighting factors of echo samples are used in the coherently summing the delayed and weighted echo samples from the one or more regions of the object.

Example A38 includes the method of any of examples A32-A39, wherein the one or more beamformed output signals are repeatedly produced from the same set of received echo samples, a partially new set of received echo samples, or a fully new set of received echo samples as a function of optimizing the one or more scalar outputs.

Example A39 includes the method of any of examples A32-A38, wherein the method is implemented by the system of any of examples A1-A31.

In some embodiments in accordance with the present technology (example A40), a method for tomographic synthetic aperture acoustic imaging includes transmitting and receiving acoustic signals to and from an object to form a synthetic aperture of an acoustic imaging system, wherein the acoustic signals include transmitted acoustic signals and received acoustic echoes returned from the object; beamforming the object coherently for one or more regions of the object as a function of position, orientation, and/or geometry of the array of transducer elements with respect to a model of the object; producing one or more beamformed output signals in digital format that includes spatial information about the one or more regions of the object derived from beamforming the acoustic echoes; processing the one or more beamformed output signals to produce at least one scalar output associated with the one or more beamformed output signals, processing the at least one scalar output to produce optimized parameters associated with (i) an array of transducer elements of the acoustic imaging system and/or (ii) the model of the object; re-beamforming the object with updated optimized parameters associated with the array of transducer elements and/or the model of the object to produce an updated one or more beamformed output signals; detecting the object by (i) comparing the at least one scalar output to a threshold value, (ii) comparing a differential change in the at least one scalar output to a threshold value, and/or (iii) comparing at least one of the optimized parameters and/or a differential change in the at least one of the optimized parameters to a threshold value; and producing an image of the object based on a rendition of the position, the orientation, the geometry, and/or the surface properties of the object, relative to the coordinate system of the array.

Example A41 includes the method of any of examples A40-A42, further comprising the method of any of claims 32-38.

Example A42 includes the method of any of examples A40-A41, wherein the method is implemented by the system of any of examples A1-A31.

In some embodiments in accordance with the present technology (example B1), a tomographic synthetic aperture acoustic imaging system includes: an array of transducer elements operable to transmit, receive, and/or transmit and receive acoustic signals at an object that forms a synthetic aperture of the acoustic imaging system with the object, wherein the acoustic signals include transmitted acoustic signals and received acoustic echoes returned from the object; an object beamformer unit comprising one or more processors and one or more memories and configured to (i) beamform the object for one or more regions of the object as a function of position, orientation, and/or geometry of the array of transducer elements with respect to a model of the object, the model of the object comprising information representative of the object, and (ii) produce one or more beamformed output signals in digital format that includes spatial information about the one or more regions of object derived from beamforming the acoustic echoes; a data processing unit, comprising a processor and a memory, in communication with the object beamformer unit and the array of transducer elements, and configured to optimize one or more beamformed output signals to determine one or more of a position, an orientation, a geometry, or a set of physical properties; and a display unit operable to produce an image of the object based on a rendition of one or more of the position, the orientation, the geometry, or the set of physical properties, relative to the coordinate system of the array of transducer elements, as determined by the data processing unit. In some example embodiments, the object beamformer unit is an independent hardware unit from the data processing unit; whereas in some embodiments, the object beamformer unit is a software module and the one or more processors and the one or more memories of the object beamformer unit are the processor and the memory, respectively, of the data processing unit.

Example B2 includes the system of any of examples B1-B35, where the system includes transmitter and receiver circuitry coupled to the array of transducer elements and configured to (i) produce and/or process transmit acoustic waveforms as digital signals to be transduced and transmitted as the one or more acoustic waveforms by one or more selected transmit transducer elements of the array, and (ii) convert the acoustic echoes that are received at one or more selected receive transducer elements of the array into digital signals representative of acoustic return echo waveforms.

Example B3 includes the system of any of examples B1-B35, wherein the object beamformer unit is configured to (i) compute delays and weights based on the geometry of the array of transducer elements and the model of the object, and (ii) generate digital signals corresponding to the produced one or more beamformed output signals that are derived from beamforming the acoustic echoes according to computed delays and weights.

Example B4 includes the system of any of examples B1-B35, wherein the data processing unit is configured to optimize the one or more beamformed output signals produced by the object beamformer unit by: (i) processing the one or more beamformed output signals to produce at least one scalar output associated with the one or more beamformed output signals, (ii) processing the at least one scalar output to produce optimized parameters associated with the array of transducer elements and/or the model of the object, (iii) instructing the object beamformer unit to re-beamform the object with updated optimized parameters associated with the array of transducer elements and/or the model of the object producing an updated one or more beamformed output signals, and (iv) detecting the object by (a) comparing the at least one scalar output to a threshold value, (b) comparing a differential change in the at least one scalar output to a threshold value, and/or (c) comparing at least one of the optimized parameters and/or a differential change in the at least one of the optimized parameters to a threshold value.

Example B5 includes the system of example B4 or any of examples B1-B35, wherein the data processing unit is configured to detect the object by comparing the at least one scalar output to the threshold value and based on a convergence of one or more optimized parameters to satisfy one or more threshold values.

Example B6 includes the system of example B4 or any of examples B1-B35, wherein the optimized parameters include one or more of an optimizer output, a step size, an optimality measure, or a residual.

Example B7 includes the system of example B4 or any of examples B1-B35, wherein the at least one scalar output produced by the data processing unit includes a quantitative value of a beamformed echo derived from one or more of integrated power, peak power, peak amplitude, peak magnitude, root-mean-squared amplitude, root-mean-squared magnitude, mean-amplitude, mean-magnitude, peak-to-peak amplitude, peak auto-correlation magnitude, peak auto-correlation amplitude, spectral bandwidth, or spectral center frequency.

Example B8 includes the system of example B4 or any of examples B1-B35, wherein at least one scalar output produced by the data processing unit includes a quantitative value of a beamformed echo derived by (i) matching the received acoustic echoes returned from the object to a stored echo using one or more of mean absolute difference, mean Euclidean distance, mean edit distance, peak cross-correlation magnitude, or peak cross-correlation amplitude, peak convolution magnitude, peak convolution amplitude, peak coherence, and peak magnitude-squared coherence; wherein the stored echo is derived from one or more of a calibrated beamformed echo from the object, a measured echo from the object, a measured transmit impulse response, a measured receive impulse response, the transmit/receive impulse response, the system impulse response, the transmitted waveform, the transmitted waveform convolved with itself, a filtered transmitted waveform, an analytic transmitted waveform, a windowed transmitted waveform, a demodulated transmitted waveform, a mathematically-defined transmitted waveform, or a mathematically-defined system impulse response.

Example B9 includes the system of example B4 or any of examples B1-B35, wherein the data processing unit or the object beamformer unit is configured to generate an optimization including two or more iterations to produce two or more of one scalar output corresponding to two or more beamformed echoes of the object corresponding to two or more sets of parameters describing the array of transducer elements and/or the object such that a more optimal of two or more of one scalar output may be chosen.

Example B10 includes the system of example B9 or any of examples B1-B35, wherein the object is detected when the optimization produces an insignificant change, below a threshold value, in the two or more of one scalar output corresponding to two or more re-beamformed echoes of the object corresponding to two or more sets of parameters describing the array of transducer elements and/or the object.

Example B11 includes the system of example B9 or any of examples B1-B35, wherein the object is detected when the optimization produces an insignificant change, below a threshold value, in the two or more sets of parameters and/or a function of two or more sets of parameters describing the array of transducer elements and/or the object corresponding to two or more re-beamformed echoes of the object.

Example B12 includes the system of example B11 or any of examples B1-B35, wherein the function applied to the two or more sets of parameters includes one or more of Euclidean norm, Manhattan norm, p-norm, maximum norm, composite norm, asymmetric norm, and Mahalanobis distance.

Example B13 includes the system of example B11 or any of examples B1-B35, wherein a same function is applied to two or more sets of parameters producing two or more scalar quantities representing two or more sets of parameters.

Example B14 includes the system of any of examples B1-B35, wherein the object beamformer unit is configured to beamform the object coherently for a plurality of regions of the object by coherently object beamforming each region of the plurality of regions of the object model separately, and subsequently coherently combining signals, obtained from each region that were coherently object beamformed, in an objective function.

Example B15 includes the system of any of examples B1-B35, wherein the object beamformer unit is configured to beamform the object coherently for a plurality of regions of the object by coherently object beamforming each region of the plurality of regions of the object model separately, and subsequently incoherently combining signals, obtained from each region that were coherently object beamformed, in an objective function.

Example B16 includes the system of any of examples B1-B35, wherein the set of physical properties of the object include one or more surface properties, one or more volumetric properties, or both of one or more surface properties and one or more volumetric properties of the object.

Example B17 includes the system of example B16 or any of examples B1-B35, wherein the set of physical properties of the object include density, bulk modulus, or an acoustic property of the object.

Example B18 includes the system of any of examples B1-B35, wherein the object beamformer unit is configured to use the same set of synthetic aperture echoes to re-beamform the object.

Example B19 includes the system of any of examples B1-B35, wherein the object beamformer unit is configured to use a partially updated set of synthetic aperture echoes to re-beamform the object.

Example B20 includes the system of any of examples B1-B35, wherein the object beamformer unit is configured to use a fully updated set of synthetic aperture echoes to re-beamform the object.

Example B21 includes the system of any of examples B1-B35, wherein the object beamformer unit is configured to store the model of the object.

Example B22 includes the system of any of examples B1-B35, wherein the object beamformer unit is configured to generate the model of the object, modify the model of the object, or both generate and modify the model of the object.

Example B23 includes the system of any of examples B1-B35, wherein the object beamformer unit is configured to store the geometry of the array of transducer elements.

Example B24 includes the system of any of examples B1-B35, wherein the object beamformer unit is configured to generate information about the geometry of the array of transducer elements, modify information about the geometry of the array of transducer elements, or generate and modify information about the geometry of the array of transducer elements.

Example B25 includes the system of any of examples B1-B35, wherein the display unit includes a display screen and is configured to present a visual display of the object on the display screen, where the rendition of the object is made useful in the frame of reference of the array of transducer elements or in an external frame of reference, such that the visual display of the object is operable to update and visualize relative movement between the object and the array of transducer elements.

Example B26 includes the system of any of examples B1-B35, wherein the object beamformer unit is configured to (i) compute delays determined from each transmitter position to points on the model of the object and back to each receiver position; (ii) compute weights for one or more of specular scattering, acoustic field directivity, attenuation, spreading loss, and complex reflectivity according to vectors of incidence, vectors of reflection, vectors of reception, transducer normal vectors, object face normal vectors, and/or a priori information about the object relating to the complex reflectivity; and (iii) apply the computed delays and the computed weights to stored echoes prior to combining delayed and weighted echoes to produce one or more beamformed echoes.

Example B27 includes the system of any of examples B1-B35, wherein the data processing unit is configured to integrate beamformed echo power over a time window, and to optimize a transformation applied to transducer element positions and normal vectors as inputs to the beamformer in order to maximize the integrated beamformer echo power over the time window.

Example B28 includes the system of any of examples B1-B35, wherein the display unit is configured to visualize the object in the frame of reference of the array of transducer elements according to the inverse of the optimized transformation.

Example B29 includes the system of any of examples B1-B35, wherein the array of transducer elements includes one or more transmitter transducer elements and one or more receiver transducer elements that are spatially separated to the object.

Example B30 includes the system of example B29 or any of examples B1-B35, wherein the one or more transmitter transducer elements and the one or more receiver transducer elements are fully or at least partially surrounding the object.

Example B31 includes the system of any of examples B1-B35, wherein the array of transducer elements includes at least three transducer elements configured to create at least three reflection samples including monostatic reflection samples and bistatic reflection samples of the object, such that the reflection samples are significantly separated on a surface of the object.

Example B32 includes the system of any of examples B1-B35, wherein the array of transducer elements includes at least three transducer elements configured to create at least three monostatic reflection samples and at least three bistatic reflection samples of the object, such that the reflection samples are significantly separated on a surface of the object.

Example B33 includes the system of any of examples B1-B35, wherein the model of the object includes a plurality of vertices and a plurality of faces approximating the object with faces no larger than one acoustic wavelength resolution.

Example B34 includes the system of any of examples B1-B35, wherein the model of the object includes a plurality of points and a plurality of surface normal vectors corresponding to each point that approximate the object within at least one acoustic wavelength resolution.

Example B35 includes the system of any of examples B1-B35, wherein the one or more acoustic waveforms include one or more composite waveforms that comprise two or more individual coded waveforms.

In some embodiments in accordance with the present technology (example B36), a method for tomographic synthetic aperture acoustic imaging includes: transmitting and receiving acoustic signals, by transducer elements of an array of transducer elements, at and from an object by forming a synthetic aperture based on transmitting of transduced acoustic waveforms at the object and receiving returned acoustic echoes from the object; beamforming the object using echo samples of the received returned acoustic echoes that returned from one or more regions of the object to produce one or more beamformed output signals, wherein the one or more beamformed output signals are functions of one or more inputs for the beamforming, wherein the one or more inputs for the beamforming includes information representative of the object; optimizing the one or more beamformed output signals to determine one or more of a position, an orientation, a geometry, or a set of physical properties of the object; and producing an image of the object based on a rendition of the one or more of the position, the orientation, the geometry, or the set of physical properties of the object.

Example B37 includes the method of any of examples B36-B45, wherein the one or more of the position, the orientation, the geometry, or the set of physical properties of the object are determined by: generating one or more scalar outputs that are based on the one or more beamformed output signals; optimizing the one or more scalar outputs as a function of at least some of the position, the orientation, the geometric property, or the physical property of the object; detecting the object by determining a degree of optimization of one or more objective functions based on values of or changes in inputs and outputs of an optimization, using an optimizer, compared to detection criteria.

Example B38 includes the method of example 37 or any of examples B36-B45, wherein the one or more scalar outputs are optimized as a function of at least some of a position, an orientation, or a geometry of the array of transducer elements.

Example B39 includes the method of any of examples B36-B45, wherein determining the one or more of the position, the orientation, the geometry, or the set of physical properties of the object includes: producing at least one scalar output associated with the one or more beamformed output signals, and processing the at least one scalar output to produce a set of optimized parameters that define the array of transducer elements and/or define the model of the object.

Example B40 includes the method of any of examples B36-B45, wherein the set of physical properties of the object include one or more surface properties, one or more volumetric properties, or both of one or more surface properties and one or more volumetric properties of the object.

Example B41 includes the method of any of examples B36-B45, wherein beamforming the object includes computing delays and weights corresponding to one or more regions of the object as a function of at least some of a position, an orientation, and a geometry of the array of transducer elements with respect to the model of the object.

Example B42 includes the method of example 41 or any of examples B36-B45, wherein the produced one or more beamformed output signals includes spatial information about the one or more regions of the object derived from coherently summing delayed and weighted echo samples from one or more regions of the object or derived from coherently multiplying delayed and weighted echo samples from one or more regions of the object.

Example B43 includes the method of any of examples B36-B45, comprising: generating delayed echo samples and weighting factors of echo samples corresponding to transmitter positions and receiver positions of transducer elements of the array, attributes of the transducer elements of the array, points of the model of the object, and attributes of the model of the object, wherein the generated delayed echo samples and weighting factors of echo samples are used in the coherently combining (e.g., summing and/or multiplying) the delayed and weighted echo samples from the one or more regions of the object.

Example B44 includes the method of any of examples B36-B45, wherein the one or more beamformed output signals are repeatedly produced from the same set of received echo samples, a partially new set of received echo samples, or a fully new set of received echo samples as a function of optimizing one or more scalar outputs.

Example B45 includes the method of any of examples B36-B45, wherein the method is implemented by the system of any of examples B1-B35.

In some embodiments in accordance with the present technology (example C1), an array of different acoustic transducer devices at different locations around a target object and configured to transmit, receive, and/or transmit and receive acoustic signals at an object to effectuate a synthetic aperture of the acoustic imaging system with the object, wherein the acoustic signals include transmitted acoustic signals and received acoustic echoes returned from the object; and a computing device in communication with the array of different acoustic transducer devices and comprising a processor and a memory, the computing device including an object beamformer unit configured to (i) beamform the object by at least combining at least some of the received acoustic echoes for one or more regions of the object as a function of position, orientation, and/or geometry of the array of transducer elements with respect to a model of the object, the model of the object comprising information representative of the object, and (ii) produce one or more beamformed output signals that includes spatial information about the one or more regions of object derived from beamforming the acoustic echoes, and the computing device including a data processing unit, in data communication with the object beamformer unit, and configured to (i) optimize one or more beamformed output signals to determine one or more of a position, an orientation, a geometry, or a set of physical properties, and (ii) produce an image of the object based on a rendition of one or more of the position, the orientation, the geometry, or the set of physical properties, relative to the coordinate system of the array of transducer elements, as determined by the data processing unit.

Example C2 includes the system of any of examples C1-C35, comprising: transmitter and receiver circuitry coupled to the array of transducer elements and configured to (i) produce and/or process transmit acoustic waveforms as digital signals to be transduced and transmitted as the one or more acoustic waveforms by one or more selected transmit transducer elements of the array, and (ii) convert the acoustic echoes that are received at one or more selected receive transducer elements of the array into digital signals representative of acoustic return echo waveforms.

Example C3 includes the system of any of examples C1-C35, wherein the object beamformer unit is configured to (i) compute delays and weights based on the geometry of the array of transducer elements and the model of the object, and (ii) generate digital signals corresponding to the produced one or more beamformed output signals that are derived from beamforming the acoustic echoes according to computed delays and weights.

Example C4 includes the system of any of examples C1-C35, wherein the data processing unit is configured to optimize the one or more beamformed output signals produced by the object beamformer unit by: (i) processing the one or more beamformed output signals to produce at least one scalar output associated with the one or more beamformed output signals, (ii) processing the at least one scalar output to produce optimized parameters associated with the array of transducer elements and/or the model of the object, (iii) instructing the object beamformer unit to re-beamform the object with updated optimized parameters associated with the array of transducer elements and/or the model of the object producing an updated one or more beamformed output signals, and (iv) detecting the object by (a) comparing the at least one scalar output to a threshold value, (b) comparing a differential change in the at least one scalar output to a threshold value, and/or (c) comparing at least one of the optimized parameters and/or a differential change in the at least one of the optimized parameters to a threshold value.

Example C5 includes the system of example C4 or any of examples C1-C35, wherein the data processing unit is configured to detect the object by comparing the at least one scalar output to the threshold value and based on a convergence of one or more optimized parameters to satisfy one or more threshold values.

Example C6 includes the system of example C4 or any of examples C1-C35, wherein the optimized parameters include one or more of an optimizer output, a step size, an optimality measure, or a residual.

Example C7 includes the system of example C4 or any of examples C1-C35, wherein the at least one scalar output produced by the data processing unit includes a quantitative value of a beamformed echo derived from one or more of integrated power, peak power, peak amplitude, peak magnitude, root-mean-squared amplitude, root-mean-squared magnitude, mean-amplitude, mean-magnitude, peak-to-peak amplitude, peak auto-correlation magnitude, peak auto-correlation amplitude, spectral bandwidth, or spectral center frequency.

Example C8 includes the system of example C4 or any of examples C1-C35, wherein at least one scalar output produced by the data processing unit includes a quantitative value of a beamformed echo derived by (i) matching the received acoustic echoes returned from the object to a stored echo using one or more of mean absolute difference, mean Euclidean distance, mean edit distance, peak cross-correlation magnitude, or peak cross-correlation amplitude, peak convolution magnitude, peak convolution amplitude, peak coherence, and peak magnitude-squared coherence; wherein the stored echo is derived from one or more of a calibrated beamformed echo from the object, a measured echo from the object, a measured transmit impulse response, a measured receive impulse response, the transmit/receive impulse response, the system impulse response, the transmitted waveform, the transmitted waveform convolved with itself, a filtered transmitted waveform, an analytic transmitted waveform, a windowed transmitted waveform, a demodulated transmitted waveform, a mathematically-defined transmitted waveform, or a mathematically-defined system impulse response.

Example C9 includes the system of example C4 or any of examples C1-C35, wherein the data processing unit or the object beamformer unit is configured to generate an optimization including two or more iterations to produce two or more of one scalar output corresponding to two or more beamformed echoes of the object corresponding to two or more sets of parameters describing the array of transducer elements and/or the object such that a more optimal of two or more of one scalar output may be chosen.

Example C10 includes the system of example C9 or any of examples C1-C35, wherein the object is detected when the optimization produces an insignificant change, below a threshold value, in the two or more of one scalar output corresponding to two or more re-beamformed echoes of the object corresponding to two or more sets of parameters describing the array of transducer elements and/or the object.

Example C11 includes the system of example C9 or any of examples C1-C35, wherein the object is detected when the optimization produces an insignificant change, below a threshold value, in the two or more sets of parameters and/or a function of two or more sets of parameters describing the array of transducer elements and/or the object corresponding to two or more re-beamformed echoes of the object.

Example C12 includes the system of example C11 or any of examples C1-C35, wherein the function applied to the two or more sets of parameters includes one or more of Euclidean norm, Manhattan norm, p-norm, maximum norm, composite norm, asymmetric norm, and Mahalanobis distance.

Example C13 includes the system of example C11 or any of examples C1-C35, wherein a same function is applied to two or more sets of parameters producing two or more scalar quantities representing two or more sets of parameters.

Example C14 includes the system of any of examples C1-C35, wherein the object beamformer unit is configured to beamform the object coherently for a plurality of regions of the object by coherently object beamforming each region of the plurality of regions of the object model separately, and subsequently coherently combining signals, obtained from each region that were coherently object beamformed, in an objective function.

Example C15 includes the system of any of examples C1-C35, wherein the object beamformer unit is configured to beamform the object coherently for a plurality of regions of the object by coherently object beamforming each region of the plurality of regions of the object model separately, and subsequently incoherently combining signals, obtained from each region that were coherently object beamformed, in an objective function.

Example C16 includes the system of any of examples C1-C35, wherein the set of physical properties of the object include one or more surface properties, one or more volumetric properties, or both of one or more surface properties and one or more volumetric properties of the object.

Example C17 includes the system of example C16 or any of examples C1-C35, wherein the set of physical properties of the object include density, bulk modulus, or an acoustic property of the object.

Example C18 includes the system of any of examples C1-C35, wherein the object beamformer unit is configured to use the same set of synthetic aperture echoes to re-beamform the object.

Example C19 includes the system of any of examples C1-C35, wherein the object beamformer unit is configured to use a partially updated set of synthetic aperture echoes to re-beamform the object.

Example C20 includes the system of any of examples C1-C35, wherein the object beamformer unit is configured to use a fully updated set of synthetic aperture echoes to re-beamform the object.

Example C21 includes the system of any of examples C1-C35, wherein the object beamformer unit is configured to store the model of the object.

Example C22 includes the system of any of examples C1-C35, wherein the object beamformer unit is configured to generate the model of the object, modify the model of the object, or both generate and modify the model of the object.

Example C23 includes the system of any of examples C1-C35, wherein the object beamformer unit is configured to store the geometry of the array of transducer elements.

Example C24 includes the system of any of examples C1-C35, wherein the object beamformer unit is configured to generate information about the geometry of the array of transducer elements, modify information about the geometry of the array of transducer elements, or generate and modify information about the geometry of the array of transducer elements.

Example C25 includes the system of any of examples C1-C35, further comprising: a display unit comprising a display screen and configured to present a visual display of the image of the object on the display screen, where the image of the object is rendered in the frame of reference of the array of transducer elements or in an external frame of reference, such that the visual display of the image of the object is operable to update and visualize relative movement between the object and the array of transducer elements.

Example C26 includes the system of any of examples C1-C35, wherein the object beamformer unit is configured to (i) compute delays determined from each transmitter position to points on the model of the object and back to each receiver position; (ii) compute weights for one or more of specular scattering, acoustic field directivity, attenuation, spreading loss, and complex reflectivity according to vectors of incidence, vectors of reflection, vectors of reception, transducer normal vectors, object face normal vectors, and/or a priori information about the object relating to the complex reflectivity; and (iii) apply the computed delays and the computed weights to stored echoes prior to combining delayed and weighted echoes to produce one or more beamformed echoes.

Example C27 includes the system of any of examples C1-C35, wherein the data processing unit is configured to integrate beamformed echo power over a time window, and to optimize a transformation applied to transducer element positions and normal vectors as inputs to the beamformer in order to maximize the integrated beamformer echo power over the time window.

Example C28 includes the system of any of examples C1-C35, wherein the display unit is configured to visualize the object in the frame of reference of the array of transducer elements according to the inverse of the optimized transformation.

Example C29 includes the system of any of examples C1-C35, wherein the array of transducer elements includes one or more transmitter transducer elements and one or more receiver transducer elements that are spatially separated to the object.

Example C30 includes the system of example C29 or any of examples C1-C35, wherein the one or more transmitter transducer elements and the one or more receiver transducer elements are fully or at least partially surrounding the object.

Example C31 includes the system of any of examples C1-C35, wherein the array of transducer elements includes at least three transducer elements configured to create at least three reflection samples including monostatic reflection samples and bistatic reflection samples of the object, such that the reflection samples are significantly separated on a surface of the object.

Example C32 includes the system of any of examples C1-C35, wherein the array of transducer elements includes at least three transducer elements configured to create at least three monostatic reflection samples and at least three bistatic reflection samples of the object, such that the reflection samples are significantly separated on a surface of the object.

Example C33 includes the system of any of examples C1-C35, wherein the model of the object includes a plurality of vertices and a plurality of faces approximating the object with faces no larger than one acoustic wavelength resolution.

Example C34 includes the system of any of examples C1-C35, wherein the model of the object includes a plurality of points and a plurality of surface normal vectors corresponding to each point that approximate the object within at least one acoustic wavelength resolution.

Example C35 includes the system of any of examples C1-C35, wherein the one or more acoustic waveforms include one or more composite waveforms that comprise two or more individual coded waveforms.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random-access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A synthetic aperture acoustic imaging system, comprising:
an array of different acoustic transducer devices at different locations around a target object and configured to transmit, receive, and/or transmit and receive acoustic signals at an object to effectuate a synthetic aperture of the acoustic imaging system with the object, wherein the acoustic signals include transmitted acoustic signals and received acoustic echoes returned from the object;
a computing device in communication with the array of different acoustic transducer devices and comprising a processor and a memory, the computing device including an object beamformer unit configured to (i) beamform the object by at least combining at least some of the received acoustic echoes for one or more regions of the object as a function of position, orientation, and/or geometry of the array of transducer elements with respect to a model of the object stored in the memory of the computing device, the model of the object comprising information representative of the object, and (ii) produce one or more beamformed output signals that includes spatial information about the one or more regions of object derived from beamforming the acoustic echoes, and the computing device including a data processing unit, in data communication with the object beamformer unit, and configured to (i) optimize one or more beamformed output signals to determine one or more of a position, an orientation, a geometry, or a set of physical properties, and (ii) produce an image of the object based on a rendition of one or more of the position, the orientation, the geometry, or the set of physical properties, relative to a coordinate system of the array of transducer elements, as determined by the data processing unit; and a display unit comprising a display screen and configured to visualize the object in the frame of reference of the array of transducer elements according to the inverse of the optimized transformation.

2. The system of claim 1, comprising:

transmitter and receiver circuitry coupled to the array of transducer elements and configured to (i) produce and/or process transmit acoustic waveforms as digital signals to be transduced and transmitted as the one or more acoustic waveforms by one or more selected transmit transducer elements of the array, and (ii) convert the acoustic echoes that are received at one or more selected receive transducer elements of the array into digital signals representative of acoustic return echo waveforms.

3. The system of claim 1, wherein the object beamformer unit is configured to (i) compute delays and weights based on the geometry of the array of transducer elements and the model of the object, and (ii) generate digital signals corresponding to the produced one or more beamformed output signals that are derived from beamforming the acoustic echoes according to computed delays and weights.

4. The system of claim 1, wherein the data processing unit is configured to optimize the one or more beamformed output signals produced by the object beamformer unit by:

(i) processing the one or more beamformed output signals to produce at least one scalar output associated with the one or more beamformed output signals, (ii) processing the at least one scalar output to produce optimized parameters associated with the array of transducer elements and/or the model of the object, (iii) instructing the object beamformer unit to re-beamform the object with updated optimized parameters associated with the array of transducer elements and/or the model of the object producing an updated one or more beamformed output signals, and (iv) detecting the object by (a) comparing the at least one scalar output to a threshold value, (b) comparing a differential change in the at least one scalar output to a threshold value, and/or (c) comparing at least one of the optimized parameters and/or a differential change in the at least one of the optimized parameters to a threshold value.

5. The system of claim 4, wherein the data processing unit is configured to detect the object by comparing the at least one scalar output to the threshold value and based on a convergence of one or more optimized parameters to satisfy one or more threshold values.

6. The system of claim 4, wherein the optimized parameters include one or more of an optimizer output, a step size, an optimality measure, or a residual.

7. The system of claim 4, wherein the at least one scalar output produced by the data processing unit includes a quantitative value of a beamformed echo derived from one or more of integrated power, peak power, peak amplitude, peak magnitude, root-mean-squared amplitude, root-mean-squared magnitude, mean-amplitude, mean-magnitude, peak-to-peak amplitude, peak auto-correlation magnitude, peak auto-correlation amplitude, spectral bandwidth, or spectral center frequency.

8. The system of claim 4, wherein at least one scalar output produced by the data processing unit includes a quantitative value of a beamformed echo derived by (i) matching the received acoustic echoes returned from the object to a stored echo using one or more of mean absolute difference, mean Euclidean distance, mean edit distance, peak cross-correlation magnitude, or peak cross-correlation amplitude, peak convolution magnitude, peak convolution amplitude, peak coherence, and peak magnitude-squared coherence; wherein the stored echo is derived from one or more of a calibrated beamformed echo from the object, a measured echo from the object, a measured transmit impulse response, a measured receive impulse response, the transmit/receive impulse response, the system impulse response, the transmitted waveform, the transmitted waveform convolved with itself, a filtered transmitted waveform, an analytic transmitted waveform, a windowed transmitted waveform, a demodulated transmitted waveform, a mathematically-defined transmitted waveform, or a mathematically-defined system impulse response.

9. The system of claim 4, wherein the data processing unit or the object beamformer unit is configured to generate an optimization including two or more iterations to produce two or more of one scalar output corresponding to two or more beamformed echoes of the object corresponding to two or more sets of parameters describing the array of transducer elements and/or the object such that a more optimal of two or more of one scalar output may be chosen.

10. The system of claim 1, wherein the object beamformer unit is configured to beamform the object coherently for a plurality of regions of the object by coherently object beamforming each region of the plurality of regions of the object model separately, and subsequently coherently combining signals, obtained from each region that were coherently object beamformed, in an objective function.

11. The system of claim 1, wherein the object beamformer unit is configured to beamform the object coherently for a plurality of regions of the object by coherently object beamforming each region of the plurality of regions of the object model separately, and subsequently incoherently combining signals, obtained from each region that were coherently object beamformed, in an objective function.

12. The system of claim 1, wherein the object beamformer unit is configured to use the same set, a fully updated set, or a partially updated set of synthetic aperture echoes to re-beamform the object.

13. The system of claim 1, wherein the object beamformer unit is configured to generate the model of the object, modify the model of the object, or both generate and modify the model of the object.

14. The system of claim 1, wherein the object beamformer unit is configured to generate information about the geometry of the array of transducer elements, modify information about the geometry of the array of transducer elements, or generate and modify information about the geometry of the array of transducer elements.

15. The system of claim 1, further comprising:

a display unit comprising a display screen and configured to present a visual display of the image of the object on the display screen, where the image of the object is rendered in the frame of reference of the array of transducer elements or in an external frame of reference, such that the visual display of the image of the object is operable to update and visualize relative movement between the object and the array of transducer elements.

16. The system of claim 1, wherein the object beamformer unit is configured to (i) compute delays determined from each transmitter position to points on the model of the object and back to each receiver position; (ii) compute weights for one or more of specular scattering, acoustic field directivity, attenuation, spreading loss, and complex reflectivity according to vectors of incidence, vectors of reflection, vectors of reception, transducer normal vectors, object face normal vectors, and/or a priori information about the object relating to the complex reflectivity; and (iii) apply the computed delays and the computed weights to stored echoes prior to combining delayed and weighted echoes to produce one or more beamformed echoes.

17. The system of claim 1, wherein the data processing unit is configured to integrate beamformed echo power over a time window, and to optimize a transformation applied to transducer element positions and normal vectors as inputs to the beamformer in order to maximize the integrated beamformer echo power over the time window.

18. The system of claim 1,
wherein the array of transducer elements includes at least three transducer elements configured to create at least three reflection samples including monostatic reflection samples and bistatic reflection samples of the object, such that the reflection samples are significantly separated on a surface of the object, or
wherein the array of transducer elements includes at least three transducer elements configured to create at least three monostatic reflection samples and at least three bistatic reflection samples of the object, such that the reflection samples are significantly separated on a surface of the object.

19. The system of claim 1, wherein the model of the object includes a plurality of vertices and a plurality of faces approximating the object with faces no larger than one acoustic wavelength resolution, or wherein the model of the object includes a plurality of points and a plurality of surface normal vectors corresponding to each point that approximate the object within at least one acoustic wavelength resolution.

20. The system of claim 1, wherein the one or more acoustic waveforms include one or more composite waveforms that comprise two or more individual coded waveforms.

21. A method for synthetic aperture acoustic imaging, comprising:
transmitting and receiving acoustic signals, by transducer elements of an array of transducer elements, at and from an object by forming a synthetic aperture based on transmitting of transduced acoustic waveforms at the object and receiving returned acoustic echoes from the object;
beamforming the object using echo samples of the received returned acoustic echoes that returned from one or more regions of the object to produce one or more beamformed output signals, wherein the one or more beamformed output signals are functions of one or more inputs for the beamforming, wherein the one or more inputs for the beamforming includes information representative of the object;
optimizing the one or more beamformed output signals to determine one or more of a position, an orientation, a geometry, or a set of physical properties of the object; and
producing an image of the object based on a rendition of the one or more of the position, the orientation, the geometry, or the set of physical properties of the object,
wherein the one or more of the position, the orientation, the geometry, or the set of physical properties of the object are determined by:
generating one or more scalar outputs that are based on the one or more beamformed output signals;
optimizing the one or more scalar outputs as a function of at least some of the position, the orientation, the geometric property, or the physical property of the object;
detecting the object by determining a degree of optimization of one or more objective functions based on values of or changes in inputs and outputs of an optimization, using an optimizer, compared to detection criteria.

22. The method of claim 21, wherein the one or more scalar outputs are optimized as a function of at least some of a position, an orientation, or a geometry of the array of transducer elements.

23. The method of claim 21, wherein determining the one or more of the position, the orientation, the geometry, or the set of physical properties of the object includes:
producing at least one scalar output associated with the one or more beamformed output signals, and
processing the at least one scalar output to produce a set of optimized parameters that define the array of transducer elements and/or define a model of the object.

24. The method of claim 21, wherein the set of physical properties of the object include one or more surface properties, one or more volumetric properties, or both of one or more surface properties and one or more volumetric properties of the object.

25. The method of claim 21, wherein beamforming the object includes computing delays and weights corresponding to one or more regions of the object as a function of at least some of a position, an orientation, and a geometry of the array of transducer elements with respect to a model of the object.

26. The method of claim 25, wherein the produced one or more beamformed output signals includes spatial information about the one or more regions of the object derived from coherently summing delayed and weighted echo samples from one or more regions of the object or derived from coherently multiplying delayed and weighted echo samples from one or more regions of the object.

27. The method of claim 21, comprising:
generating delayed echo samples and weighting factors of echo samples corresponding to transmitter positions and receiver positions of transducer elements of the array, attributes of the transducer elements of the array, points of a model of the object, and attributes of the model of the object,
wherein the generated delayed echo samples and weighting factors of echo samples are used in the coherently combining the delayed and weighted echo samples from the one or more regions of the object.

28. The method of claim 21, wherein the one or more beamformed output signals are repeatedly produced from the same set of received echo samples, a partially new set of received echo samples, or a fully new set of received echo samples as a function of optimizing one or more scalar outputs.

29. A synthetic aperture acoustic imaging system, comprising:
- an array of different acoustic transducer devices at different locations around a target object and configured to transmit, receive, and/or transmit and receive acoustic signals at an object to effectuate a synthetic aperture of the acoustic imaging system with the object, wherein the acoustic signals include transmitted acoustic signals and received acoustic echoes returned from the object; and
- a computing device in communication with the array of different acoustic transducer devices and comprising a processor and a memory, the computing device including an object beamformer unit configured to (i) beamform the object by at least combining at least some of the received acoustic echoes for one or more regions of the object as a function of position, orientation, and/or geometry of the array of transducer elements with respect to a model of the object stored in the memory of the computing device, the model of the object comprising information representative of the object, and (ii) produce one or more beamformed output signals that includes spatial information about the one or more regions of object derived from beamforming the acoustic echoes, and the computing device including a data processing unit, in data communication with the object beamformer unit, and configured to (i) optimize one or more beamformed output signals to determine one or more of a position, an orientation, a geometry, or a set of physical properties, and (ii) produce an image of the object based on a rendition of one or more of the position, the orientation, the geometry, or the set of physical properties, relative to a coordinate system of the array of transducer elements, as determined by the data processing unit,
- wherein the object beamformer unit is configured to beamform the object coherently for a plurality of regions of the object by coherently object beamforming each region of the plurality of regions of the object model separately, and subsequently incoherently combining signals, obtained from each region that were coherently object beamformed, in an objective function.

30. A synthetic aperture acoustic imaging system, comprising:
- an array of different acoustic transducer devices at different locations around a target object and configured to transmit, receive, and/or transmit and receive acoustic signals at an object to effectuate a synthetic aperture of the acoustic imaging system with the object, wherein the acoustic signals include transmitted acoustic signals and received acoustic echoes returned from the object;
- a memory device configured to store a model of the object;
- a computing device in communication with the array of different acoustic transducer devices and the memory device and comprising a processor and a memory, the computing device including an object beamformer unit configured to (i) beamform the object by at least combining at least some of the received acoustic echoes for one or more regions of the object as a function of position, orientation, and/or geometry of the array of transducer elements with respect to the model of the object, the model of the object comprising information representative of the object, and (ii) produce one or more beamformed output signals that includes spatial information about the one or more regions of object derived from beamforming the acoustic echoes, and the computing device including a data processing unit, in data communication with the object beamformer unit, and configured to (i) optimize one or more beamformed output signals to determine one or more of a position, an orientation, a geometry, or a set of physical properties, and (ii) produce an image of the object based on a rendition of one or more of the position, the orientation, the geometry, or the set of physical properties, relative to a coordinate system of the array of transducer elements, as determined by the data processing unit; and
- a display unit comprising a display screen and configured to visualize the object in the frame of reference of the array of transducer elements according to the inverse of the optimized transformation.

* * * * *

UNITED STATES PATENT AND TRADEMARK OFFICE
CERTIFICATE OF CORRECTION

PATENT NO. : 11,520,043 B2
APPLICATION NO. : 17/581495
DATED : December 6, 2022
INVENTOR(S) : Dustin E. Kruse It is certified that error appears in the above-identified patent and that said Letters Patent is hereby corrected as shown below:

In the Specification

In Column 21, Line 52, delete "Plucker" and insert -- Plücker --.

In Column 23, Line 50, delete "putch" and insert -- pitch --.

In Column 28, Line 15, delete "($M_A$,IP))" and insert -- ($M_A$,IP) --.

In Column 31, Line 13, delete "$\hat{n}_r \cdot \hat{R}|$." and insert -- $|\hat{n}_r \cdot \hat{R}|$. --.

In Column 34, Line 42, delete "$M_O{}^{m}$" and insert -- $M_O{}^m$, --.

In Column 34, Line 49, delete "$M_O{}^{m}$" and insert -- $M_O{}^m$, --.

In Column 41, Line 56, delete "Mahalanohis" and insert -- Mahalanobis --.

Signed and Sealed this
Fifth Day of March, 2024

*Katherine Kelly Vidal*
Katherine Kelly Vidal
*Director of the United States Patent and Trademark Office*